(12) United States Patent
Teng et al.

(10) Patent No.: US 10,850,096 B2
(45) Date of Patent: Dec. 1, 2020

(54) METHOD OF RELIEVING OR ALLEVIATING PAIN SUFFERED BY ABDOMINAL CANCER PATIENTS

(71) Applicants: Gaojun Teng, Nanjing (CN); Yonghua Dong, Shanghai (CN); Huaqing Yin, Shanghai (CN); Jiulin Guo, Shanghai (CN)

(72) Inventors: Gaojun Teng, Nanjing (CN); Yonghua Dong, Shanghai (CN); Huaqing Yin, Shanghai (CN); Jiulin Guo, Shanghai (CN)

(73) Assignee: Shanghai Golden Leaf Medtech Co., Ltd., Shanghai (CN)

( * ) Notice: Subject to any disclaimer, the term of this patent is extended or adjusted under 35 U.S.C. 154(b) by 152 days.

(21) Appl. No.: 16/236,639

(22) Filed: Dec. 31, 2018

(65) Prior Publication Data
US 2019/0201689 A1 Jul. 4, 2019

Related U.S. Application Data

(60) Provisional application No. 62/612,527, filed on Dec. 31, 2017.

(51) Int. Cl.
| | | |
|---|---|---|
| *A61N 1/04* | (2006.01) | |
| *A61N 1/36* | (2006.01) | |
| *A61B 18/14* | (2006.01) | |
| *A61N 1/40* | (2006.01) | |
| *A61B 18/00* | (2006.01) | |
| *A61N 1/06* | (2006.01) | |

(52) U.S. Cl.
CPC ...... *A61N 1/36002* (2017.08); *A61B 18/1492* (2013.01); *A61N 1/0456* (2013.01); *A61B 2018/00267* (2013.01); *A61B 2018/00404* (2013.01); *A61N 1/06* (2013.01); *A61N 1/3603* (2017.08); *A61N 1/36017* (2013.01); *A61N 1/36021* (2013.01); *A61N 1/40* (2013.01)

(58) Field of Classification Search
CPC ...... A61B 18/1492; A61B 2018/00029; A61B 2018/0016; A61B 2018/00166; A61B 2018/00267; A61B 2018/00404; A61B 2018/00434; A61B 2018/00488; A61B 2018/00494; A61B 2018/00529; A61B 2018/00559; A61B 2018/00577; A61B 2018/00791; A61B 2018/124; A61B 2090/064; A61B 2562/0233; A61B 2562/0247; A61N 1/0456; A61N 1/06; A61N 1/36002; A61N 1/36017; A61N 1/36021; A61N 1/3603; A61N 1/40
See application file for complete search history.

(56) References Cited

U.S. PATENT DOCUMENTS

2016/0120597 A1* 5/2016 Azamian ............ A61K 31/05
606/41

* cited by examiner

*Primary Examiner* — George Manuel
(74) *Attorney, Agent, or Firm* — Guosheng Wang; United States Research and Patent Firm

(57) ABSTRACT

The present invention provides a method of relieving or alleviating abdominal cancer pain or improving pain VAS score in a cancer patient Multiple electrodes are placed within a segment of the abdominal aorta of the patient and against blood vessel wall of the abdominal aorta. Radiofrequency energy is released through at least one of the multiple electrodes to nearby tissues, so as to increase the temperature of the nearby tissues and induce a thermal alteration of the nearby tissues.

20 Claims, 33 Drawing Sheets

QQL-100 Scores Before and After Procedure

| Score | Before | 2 wk after | 4 wk after | 8 wk after | P Value |
|---|---|---|---|---|---|
| Physical | 41.43 ± 2.57 | 49.86 ± 2.61 | 50.86 ± 3.98 | 51.00 ± 4.69 | .004 |
| Psychologic | 29.29 ± 4.42 | 39.43 ± 4.61 | 39.86 ± 4.74 | 39.83 ± 5.64 | .004 |
| Level of Independence | 26.71 ± 2.36 | 36.00 ± 3.65 | 36.00 ± 3.00 | 35.50 ± 2.59 | <.001 |
| Social Relationships | 26.43 ± 3.21 | 27.57 ± 3.15 | 27.29 ± 3.04 | 27.33 ± 3.27 | >.999 |
| Environment | 93.57 ± 3.74 | 96.00 ± 4.47 | 94.86 ± 4.53 | 94.50 ± 4.42 | >.999 |
| Spirituality | 9.14 ± 1.35 | 9.86 ± 1.07 | 9.71 ± 1.70 | 9.50 ± 2.07 | >.999 |

QOL = quality of life.

Figure 19

METHOD OF RELIEVING OR ALLEVIATING PAIN SUFFERED BY ABDOMINAL CANCER PATIENTS

CROSS-REFERENCE TO RELATED APPLICATIONS

This application claims the benefit of U.S. Provisional Patent Application No. 62/612,527 filed on Dec. 31, 2017, which is incorporated herein by reference in its entirety.

FIELD OF THE INVENTION

The present invention generally relates to a method of relieving or alleviating pain suffered by a cancer patient. Although the invention will be illustrated, explained and exemplified for pains associated with abdominal cancer such as pancreatic cancer, cervical carcinoma, cholangiocarcinoma, and esophageal cancer, it should be appreciated that the present invention can also be applied to other fields of pain management.

BACKGROUND OF THE INVENTION

Despite that modern treatments have increased life expectancy for cancer patients, these patients are exposed to pain for longer period of time. Pain is a common and debilitating problem for patients with malignancies: 67% of patients with cancer have pain or take narcotics for prolonged periods of time. Cancer pain management is a formidable problem for physicians and may result in a substantial burden to the public health care system. Known pain management strategies have remained virtually unchanged for years. In 2014, the American Cancer Society forecast that annual deaths due to cancer of the pancreas, liver, bile ducts, stomach, bowel, uterine cervix, bladder and prostate would total 176,000. A portion of these patients will develop visceral and neuropathic pain, of which 20% will become refractory to opiates and to all their possible combinations with steroids, non-steroidal anti-inflammatory drugs and neuroleptics. Between 5% and 7% of patients with intractable pain experience a severe deterioration in their quality of life, leading to a negative impact on social and family life and an increased burden on health services.

The World Health Organization (WHO) proposed a 3-step analgesic ladder as a guideline for the management of cancer pain. The 3 steps making up the ladder are nonopioid drugs (such as aspirin), weak opioid drugs (such as codeine), and strong opioid drugs (such as morphine) Opioid analgesics are often required to control cancer pain. Adverse events (AEs) from opioids are debilitating and worsen as larger doses are administered. Management of cancer pain often needs chronic use of high-dose analgesics, which are generally associated with several adverse effects and somewhat addictive. Common side-effects are nausea, vomiting, constipation, sedation, and even respiratory depression. An alternative to opioid therapy is celiac plexus neurolysis (CPN). CPN refers to permanent destruction of the celiac plexus with the use of ethanol or phenol and has been performed to relieve pain of epigastric lesions for almost 100 years. CPN was initially performed intraoperatively and then guided by fluoroscopy or computerized tomography (CT). Potential severe complications of CPN include neurologic injuries, pneumothorax, arterial injury, local hematoma, pleuritis, transient hematuria, pericarditis, intervertebral disk injury, and retroperitoneal abscess, because the needle may traverse upper visceral tissue or organs.

Endoscopic ultrasound-guided celiac plexus neurolysis (EUS-CPN) is safer and more convenient, since it can provide real-time precise imaging. EUS-CPN was effective in alleviating pain in 73%-80% of patients with pancreatic cancer and in 51%-59% of patients with chronic pancreatitis. However, several major adverse events of EUS-CPN have been reported, such as retroperitoneal bleeding and abscess, necrosis and perforation of stomach, and paraplegia.

Bruno Damascelli has published an article titled "ENDOVASCULAR DENERVATION OF THE COELIAC OR HYPOGASTRIC ARTERIES TO MANAGE REFRACTORY ABDOMINAL CANCER PAIN" in Interventional News, 24 Oct. 2016. However, there remains a need for a simpler and more effective solution for cancer pain management.

SUMMARY OF THE INVENTION

Advantageously, the present invention meets such a need by providing a method of relieving or alleviating abdominal cancer pain or improving pain. Visual Analog Score (VAS) score in a cancer patient. The method includes at the steps of:

(1) placing multiple electrodes within a segment of the abdominal aorta of the patient and against blood vessel wall of the abdominal aorta by percutaneous transluminal intravascular access, wherein said segment is defined as between the origin of celiac artery and the origin of superior mesenteric artery;

(2) adhering a surface electrode on an external surface such as skin of the patient; and (3) releasing radiofrequency energy through at least one of the multiple electrodes to nearby tissues, so as to increase the temperature of the nearby tissues and induce a thermal alteration of the nearby tissues.

The above features and advantages and other features and advantages of the present invention are readily apparent from the following detailed description of the best modes for carrying out the invention when taken in connection with the accompanying drawings.

BRIEF DESCRIPTION OF THE SEVERAL VIEWS OF THE DRAWINGS

The present invention is illustrated by way of example, and not by way of limitation, in the figures of the accompanying drawings and in which like reference numerals refer to similar elements. All the figures are schematic and generally only show parts which are necessary in order to elucidate the invention. For simplicity and clarity of illustration, elements shown in the figures and discussed below have not necessarily been drawn to scale. Well-known structures and devices are shown in simplified form, omitted, or merely suggested, in order to avoid unnecessarily obscuring the present invention.

FIG. 19 illustrates the improvement of cancer patient's Quality of Life in accordance with an exemplary embodiment of the present invention.

DETAILED DESCRIPTION OF THE PREFERRED EMBODIMENT

Figure 1A:
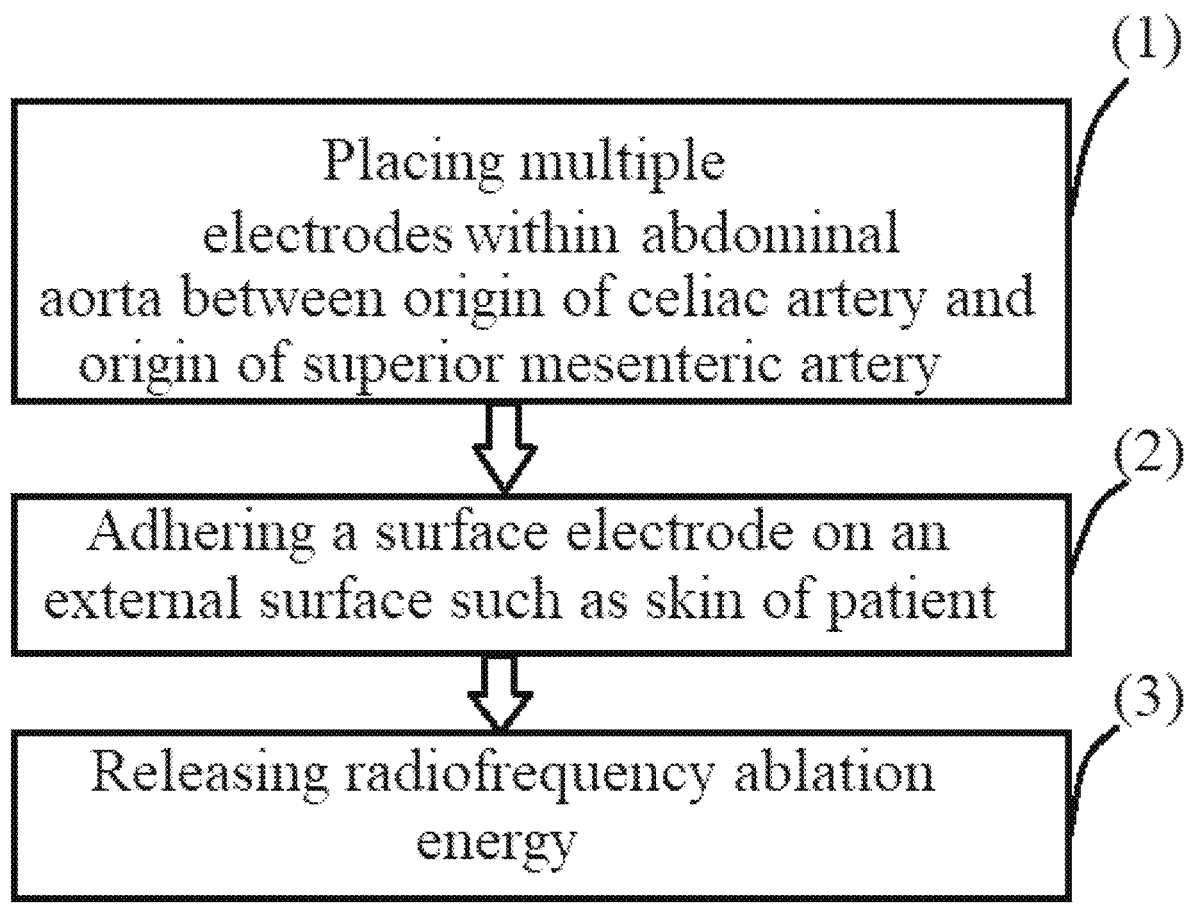
FIG. 1A is a flow chart of the method according in an exemplary embodiment of the present invention.

In the following description, for the purposes of explanation, numerous specific details are set forth in order to provide a thorough understanding of the present invention. It is apparent, however, to one skilled in the art that the present invention may be practiced without these specific details or with an equivalent arrangement.

Where a numerical range is disclosed herein, unless otherwise specified, such range is continuous, inclusive of both the minimum and maximum values of the range as well as every value between such minimum and maximum values. Still further, where a range refers to integers, only the integers from the minimum value to and including the maximum value of such range are included. In addition, where multiple ranges are provided to describe a feature or characteristic, such ranges can be combined.

In the present invention, pain is defined as an unpleasant sensory and emotional experience associated with actual or potential tissue damage, or described in terms of such damage. Pain may be a symptom of an underlying condition, and it is a complex process influenced by both physiological and psychological factors. Pain can make a patient feel tired, depressed, angry, irritable, lonely, and stressed; and cause problems with the patient's daily activities, interest in work and hobbies, sleep, eating, relationships with friends and family, and enjoyment of life. Acute pain is severe and is due to damage caused by an injury and tends to only last a short time. Acute pain is most often a sign that the body has been injured in some way. This pain generally goes away as the injury heals. For example, having an operation can cause acute pain. The pain goes when the wound heals. In the meantime, painkillers will usually keep it under control.

The present invention focuses more on chronic pain. In contrast to acute pain, chronic pain lasts for a longer time. Chronic pain is also called persistent pain. Chronic pain may be caused by changes to the nerves. Chronic pain may originate in the body, or in the brain or spinal cord. People with chronic pain tend to have higher rates of depression, anxiety, and sleep disturbances. Chronic pain may contribute to decreased physical activity due to fear of exacerbating pain, often resulting in weight gain. In some embodiments of the invention, the pain to be managed may include incident pain and breakthrough pain. Incident pain can come on quickly, for example, when patients have a dressing changed or move around. Breakthrough pain is a flare of pain that happens even though patients are taking pain medicine regularly for chronic pain. It's called breakthrough pain because it "breaks through" the pain relief the patients get from the regular pain medicine. Breakthrough pain is not controlled by the regular doses of pain medicines. It varies in intensity and usually cannot be predicted. Breakthrough pain often has the same cause as chronic pain. Chronic cancer pain is defined as cancer or its treatment related visceral, musculoskeletal, or bony pain.

Cancer pain can be caused by the disease itself or by treatments. Many people with cancer experience pain while undergoing treatment; and about 1 out of 3 people treated for cancer will feel pain. Almost all people in the advanced stages of cancer experience pain. Most cancer pain is caused by the tumor pressing on bones, nerves or other organs in the body. As a tumor grows, it may put pressure on nerves, bones or other organs, causing pain. When a tumor spreads to the spine, it can press on the spinal cord, a phenomenon called spinal cord compression. Cancer pains may be caused by cancer treatment, or by tests used to diagnose cancer and the effectiveness of cancer treatment. Cancer pains may also result from fracturing of bones, infection or inflammation associated with the disease. Cancer pain may not just arise from the physical effect of the cancer on a region of the body, but also may be caused by the chemicals that may be secreted from cancerous cells and/or tissues.

Figure 1B:
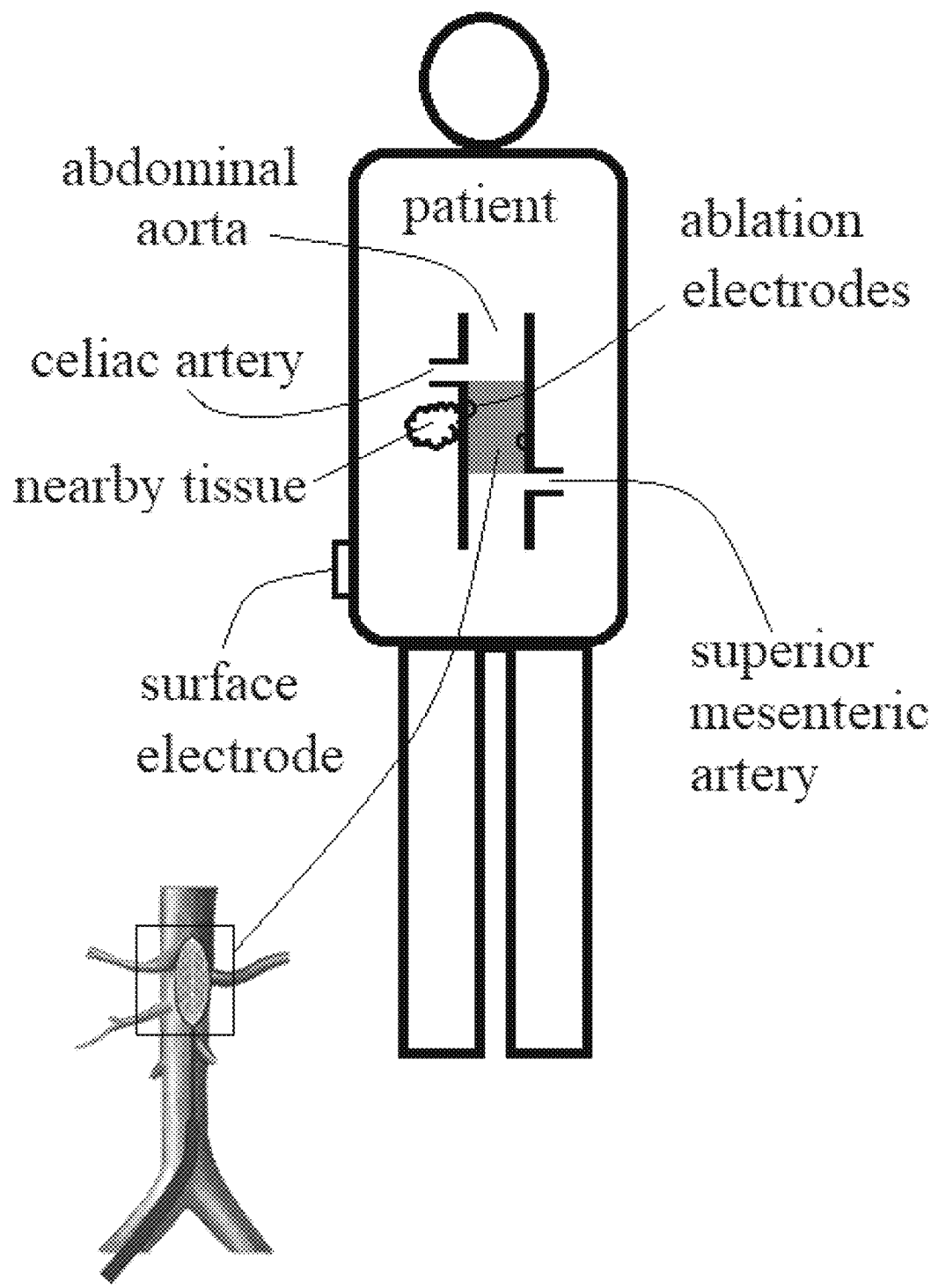
FIG. 1B illustrates the target segment in the abdominal aorta of a patient in an exemplary embodiment of the present invention.

As shown in FIGS. 1A and 1B, the present invention provides a method of relieving or alleviating abdominal cancer pain or improving pain VAS score in a cancer patient. Step (1) is placing multiple radiofrequency ablation electrodes (internal electrodes) within a segment of the abdominal aorta of the patient and against blood vessel wall of the abdominal aorta by percutaneous transluminal intravascular access. The abdominal aorta gives rise to lumbar and musculophrenic arteries, renal and middle suprarenal arteries, and visceral arteries (the celiac trunk, the superior mesenteric artery and the inferior mesenteric artery). It ends in a bifurcation into the left and right common iliac arteries. At the point of the bifurcation, there also springs a smaller branch, the median sacral artery.

The above "segment" within which the multiple electrodes are placed is defined as between the origin of celiac artery and the origin of superior mesenteric artery. The origin of celiac artery is the location where the patient's celiac artery and abdominal aorta intersect, or the location where the patient's celiac artery braches off the abdominal aorta. The origin of superior mesenteric artery is the location where the patient's superior mesenteric artery and abdominal aorta intersect, or the location where the patient's superior mesenteric artery braches off the abdominal aorta. There may be 1-12 internal electrodes such as 6 radiofrequency (RF) electrodes with the segment.

Various embodiments of the present invention use the femoral artery for the endovascular method. Endovascular diagnostic and therapeutic procedures are generally performed through the femoral artery. Some of the reasons for this generalized approach include its location, easy approach for puncture and hemostasis, low rate of complications, technical ease, wide applicability and relative patient comfort. Femoral puncture also allows access to virtually all of the arterial territories and affords favorable ergonomics for the operator in most instances.

In step (2), a surface electrode (or external electrode) is adhered on an external surface such as skin of the patient. The method may further include a step of adjusting or changing the adhesion position of the surface electrode on the back or butt of the patient (not on the belly of the patient) to vary the impedance between the surface electrode and a given electrode within the abdominal aorta until the impedance falls within the range of 180-220 such as 200 Ohms, before step (2).

In Step (3), the radiofrequency energy may be released at a level of no more than 9 W (joule per second) to prevent spasm of the patient. The inventors have unexpectedly discovered that an energy level of higher than 9 W has a risk of spasm. The radiofrequency energy may be released through an alternating current of 460-470 KHz such as 465 KHz between the surface electrode and a given electrode within the abdominal aorta.

In preferred embodiments, the cancer is selected from pancreatic cancer, cervical carcinoma, cholangiocarcinoma, and esophageal cancer. Advantageously, the average QOL-100 score increases >25 points for patients after the method is completed, as compared to that before the method is completed. The average visual analog score (VAS) of the patient is reduced by ≥4 points after the method is completed, as compared to that before the method is completed, indicating a significant pain palliation. As a result, less amount of analgesic is needed by the patient. The method of the invention thus further comprises administrating a first daily amount of analgesic to the patient before step (1), and administrating a second daily amount of analgesic to the patient after step (3), wherein the second daily amount is less than 50% of the first daily amount.

In Step (3), the radiofrequency energy may be released with a temperature threshold setting of 60° C. to ensure that collagen does not denature, tissue does not shrink, and cell wall does not break, in the nearby tissue. In general, when tissue temperature rises above about 50° C., protein is permanently damaged. If heated over about 65° C., collagen denatures and tissue shrinks. If heated over about 65° C. and up to 100° C., cell walls break and oil separates from water. Above about 100° C., tissue desiccates.

The thermal heating effects according to the present invention can include both thermal ablation and non-ablative thermal alteration or damage (e.g., via sustained heating and/or resistive heating). Desired thermal heating effects may include raising the temperature of the target segment above a desired threshold to achieve non-ablative thermal alteration, and/or above a higher temperature to achieve ablative thermal alteration. For example, the target temperature can be above body temperature (e.g., approximately 37° C.) but less than about 45° C. for non-ablative thermal alteration, or the target temperature can be about 45-60° C. or higher for the ablative thermal alteration. The time period for non-ablative thermal alteration (<45° C.) is defined as Tna, the time period for ablative thermal alteration (≥45° C.) is defined as Ta, and the ratio between the two is defined as Rna/a.

In step (3), the radiofrequency energy may be released for a continuous period of 60-120 seconds for each of the multiple electrodes one by one, which protocol is defined as one session. Step (3) may include two, three, four, or more such sessions that are separately carried out. The thermal alteration comprises non-ablative thermal alteration, ablative thermal alteration, or any combination thereof; and wherein the thermal alteration produces a lesion with a depth of 5-8 mm or 5.9-6.9 mm such as about 6.4 mm in the nearby tissues. In various embodiments, as described above, the time period for non-ablative thermal alteration (<45° C.) is defined as Tna, the time period for ablative thermal alteration (≥45° C.) is defined as Ta, and the ratio between the two is defined as Rna/a; and Rna/a is generally in the range of from 5:115 to 17:43 (seconds). For example, for a case of cervical cancer or cervical carcinoma, Rna/a values are in the range of from 5:115 to 17:43 such as Rna/a values of 10:50, 8:52, 5:55, 5:55, 12:48, and 17:43 (seconds) for a first session; and Rna/a values of 5:55, 12:108, 20:45, 7:113, 5:115, and 6:114 (seconds) for a second session. For a case of esophageal cancer with retroperitoneum lymph nodes invasion, Rna/a values are in the range of from 3:57 to 10:50 such as Rna/a values of 10:50, 5:55, and 8:52 (seconds) for a first session; Rna/a values of 9:51, 9:51, 8:52, 7:53, and 4:56 (seconds) for a second session; Rna/a values of 3:57, 5:55, 3:57, 3:57, 4:56, and 3:57 (seconds) for a third session; and Rna/a values of 7:53, 5:55, 3:57, 3:57, 9:51, and 3:57 (seconds) for a fourth session. For a case of pancreatic cancer, Rna/a values are in the range of from 6:114 to 28:92 such as Rna/a values of 10:110, 10:110, 6:114, 19:10,1 21:99, and 20:100 (seconds) for a first session, and Rna/a values of 28:92, 25:95, 15:105, 20:100, and 20:100 (seconds) for a second session. For another case of pancreatic cancer, Rna/a values are in the range of from 5:115 to 18:102 such as Rna/a values of 15:105, 17:103, 5:115, 10:110, 10:110, and 18:102 (seconds) for a first session, and Rna/a values of 5:55, 10:110, 10:110, 15:105, 10:110, and 12:108 (seconds) for a second session. For still another case of pancreatic cancer, Rna/a values are in the range of from 8:112 to 25:95 such as Rna/a values of 18:102, 25:95, 10:110, 10:110, and 13:107 (seconds) for a first session, and Rna/a values of 10:110, 10:110, 8:112, 10:110, 10:110, and 9:111 (seconds) for a second session.

According to some embodiments of the invention, an external control unit can be coupled to a catheter to provide RF energy and temperature monitoring. An electrode activation circuitry may be configured to control activation and deactivation of the multiple electrodes in accordance with a predetermined energy delivery protocol and in response to signals received from temperature measuring circuitry.

According to some embodiments, temperature at or near the electrode and/or electrode-tissue can be measured using an optical fiber that extends along the catheter shaft and terminates at or near the electrode assembly. In some configurations, temperature measurements can be made by an optical fiber that has evanescent loss that varies with temperature, or by analyzing the Raman scattering of the optical fiber.

Temperature sensors provide for continuous monitoring of tissue temperatures, and RF generator power is automatically adjusted so that the target temperatures are achieved and maintained. An impedance sensor arrangement may be used to measure and monitor electrical impedance during the process, and the power and timing of the RF generator may be moderated based on the impedance measurements or a combination of impedance and temperature measurements.

Temperature-measurement devices are for example, thermocouples, thermistors, and other temperature sensors Following types of thermocouples may be used in the present invention: nickel alloy, platinum/rhodium alloy, tungsten/rhenium alloy, gold/iron alloy, noble metal alloy, platinum/molybdenum alloy, iridium/rhodium alloy, pure noble metal, Type K, Type T, Type E, Type J, Type M, Type N, Type B, Type R, Type S, Type C, Type D, Type G, and/or Type P.

According to some embodiments, impedance can be measured and monitored for each electrode, in a unipolar configuration, or between electrode assemblies, in a bipolar configuration. Changes in tissue impedance due to heating and ablation can be monitored by an external control unit, alone or along with temperature monitoring, to enable automatic or semi-automatic control of an ablation procedure.

Without being bound to any particular theory, it is believed that the process of the present invention causes controllable injury to nerves in the neighborhood of the target segment. The nerves include those within the walls of one or more blood vessels such as abdominal aorta, celiac artery, superior mesenteric artery, and other nearby blood vessels such as renal artery. The nerves also include those unassociated with any walls of blood vessels. The nerves may even include those within the spine of the patient. The "controllable injury" according to the present invention includes a spectrum of nerve injuries: (1) transient and reversible nerve injury, (2) more severe than (1) but remain reversible nerve injury if the process of the invention is terminated in a timely manner; and (3) severe and irreversible nerve injury, resulting in permanent cessation of nerve activity.

As used herein, the terms "distal" and "proximal" define a position or direction with respect to the treating clinician or clinician's control device (e.g., a handle assembly). "Distal" or "distally" refers to a position distant from or in a direction away from the clinician or clinician's control device. "Proximal" or "proximally" refers a position near or in a direction toward the clinician or clinician's control device.

The present invention provides a method for altering/ablating extravascular target tissue from within a blood vessel, particularly within the patient's abdominal aorta. With the treatment according to the present invention, the extent and relative permanency of nerve injury may be tailored to achieve a desired reduction in sympathetic nerve activity (including a partial or complete block) and to achieve a desired degree of permanency (including temporary or irreversible injury).

In preferred embodiments, the multiple electrodes consist of six electrodes configured to create interrupted spiral but full circumferential lesions on internal wall of said segment of the abdominal aorta of the patient. The multiple electrodes used in the present method may be a part of any suitable catheter apparatus, for example, the catheter device as described in Chinese Patent Application 201410035836.5 published as CN 103767787A, the content of which is incorporated herein in its entirety.

Figure 1C:
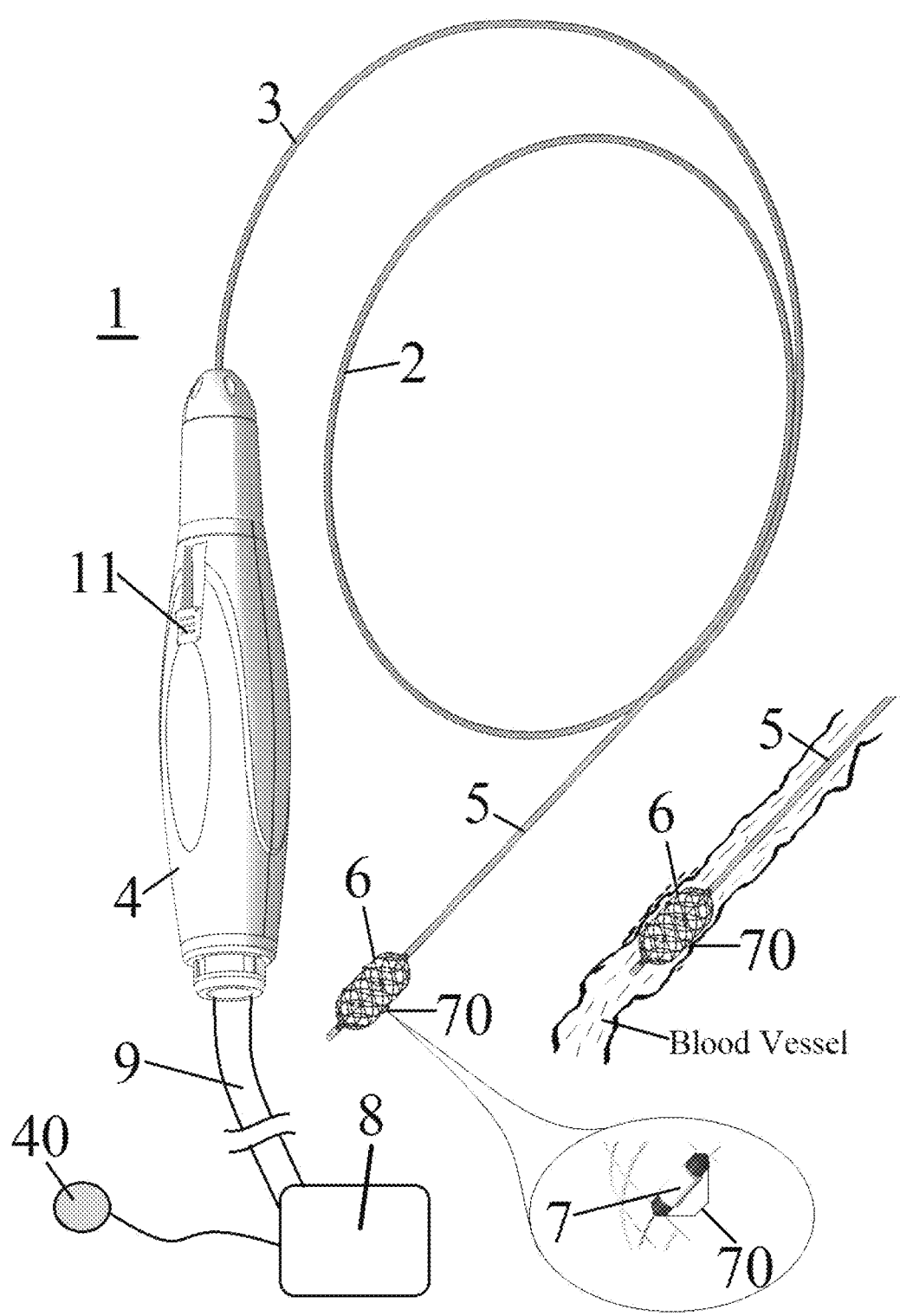
FIG. 1C schematically shows a catheter system used in an exemplary embodiment of the present invention.

In various exemplary embodiments, the multiple electrodes used in the present method are six electrodes in a catheter apparatus as shown in FIG. 1C. The system includes a catheter apparatus 1 that can be operably coupled to an energy source or energy generator 8. The catheter apparatus 1 includes an elongated shaft 2 having a proximal portion 3, a handle assembly 4 at a proximal region of the proximal portion 3, and a distal portion 5 extending distally relative to the proximal portion 3. The catheter apparatus 1 further includes an expandable carrier 6 carrying at least one therapeutic assembly 70 including a therapeutic member 7 for intravascular treatment. The carrier 6 is located at, or proximate to, the distal portion 5 of the elongated shaft 2.

Figure 2:
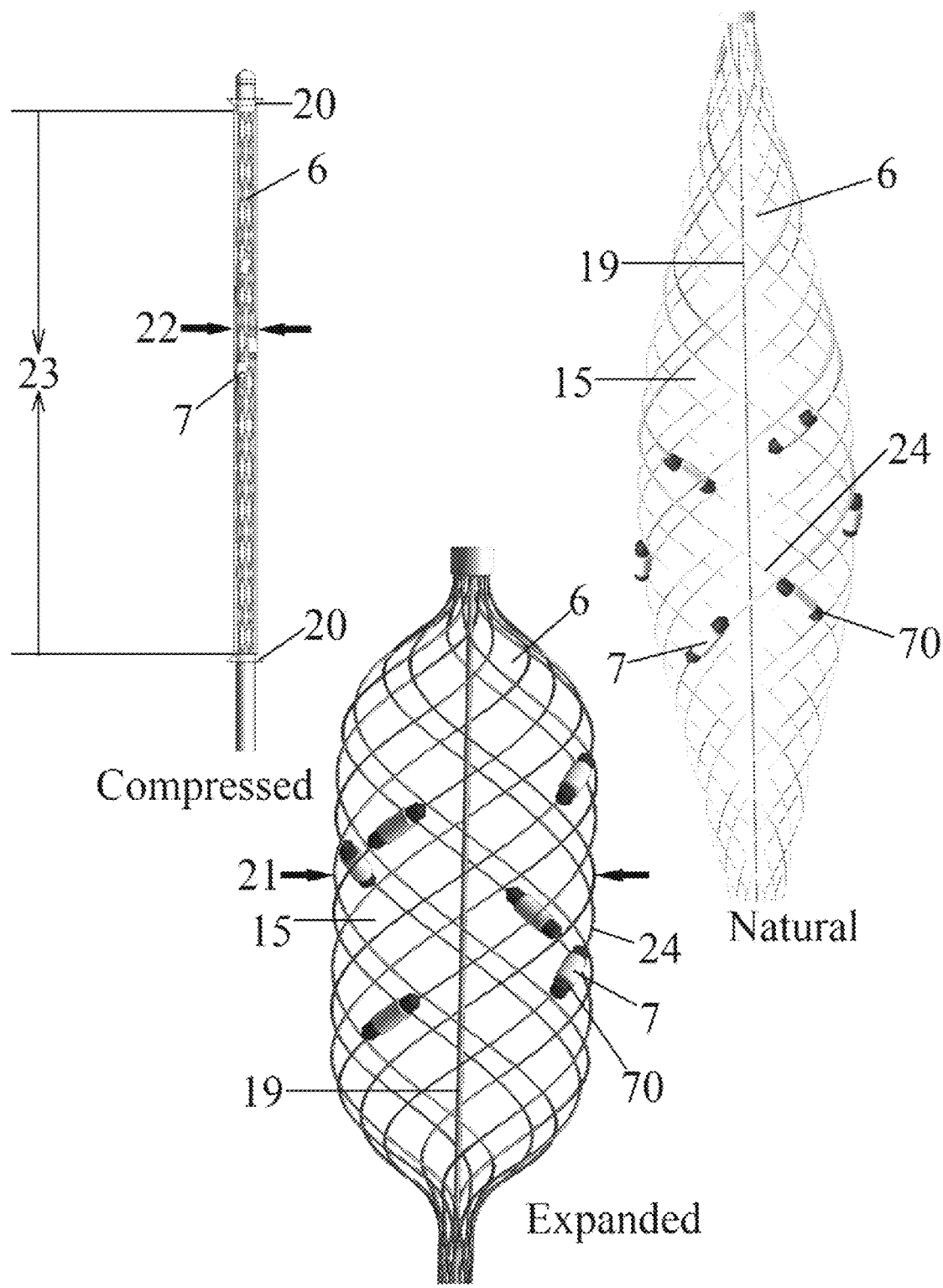
FIG. 2 shows different configurations of the carrier used in an exemplary embodiment.

As shown in FIG. 2, the carrier 6 is configured to be delivered to a blood vessel in a compressed (or low-profile, or delivery, or compacted) configuration. The carrier 6 in compressed configuration can be stored within a protective tube 20. Upon delivery to the target site within the blood vessel, the carrier 6 may be deployed into an expanded (or treatment, or deployed) configuration, bringing the therapeutic member 7 in contact with the walls of the vessel. In various embodiments, therapeutic member 7 is configured to deliver energy at the treatment site and provide therapeutically-effective electrically- and/or thermally-induced medical effect. In some embodiments, the carrier 6 may be placed in the deployed configuration or arrangement via remote actuation, e.g., via an actuator 11, such as a knob, pin, or lever carried by the handle 4, as shown in FIG. 1C. In other embodiments, however, the carrier 6 may be movable between the delivery and deployed configurations using other suitable mechanisms or techniques (e.g., self-expanding). For example, the carrier 6 may be deployed into a natural configuration without any external force imposed upon it, i.e. carrier 6 is neither compressed nor expanded, also bringing the therapeutic member 7 in contact with the walls of the vessel. In some embodiments, a delivery sheath (not shown) is used for deploying the carrier 6. The carrier 6 can self-expand and lengthen when the delivery sheath is retracted.

The carrier 6 is capable of expanding to a maximum diameter 21 that is larger than a collapsed diameter, as shown in FIG. 2. Further, the carrier 6 may be sized so that the maximum diameter 21 is larger than the lumen diameter of the blood vessel. In some embodiments, when inserted into a patient, the carrier 6 expands radially to span the vessel lumen. In other examples, the largest transverse dimension of the carrier 6 is approximately or slightly less than the diameter of the blood vessel lumen, so as to give room to other parts projecting outwardly from the carrier 6. A slight amount of vessel distension may be caused without undue injury and the carrier 6 may expand such that its largest transverse dimension is slightly more than the natural lumen diameter of the blood vessel, or such that the therapeutic member 7 is slightly pressed into the wall of the blood vessel. Sometimes, the carrier 6 that causes slight and non-injurious distension of an artery wall may advantageously provide stable contact force between the therapeutic member 7 and the artery wall and/or hold the therapeutic member 7 in place even as the artery moves with respiratory motion and pulsing blood flow. In some embodiments, the blood vessel lumen diameter can restrict the expansion of the carrier 6 and provide a limit to the maximum diameter 21. This restriction can cause the carrier 6 to form more of a cylindrical tapered shape than a prolate spheroid shape. Because the lumen diameter varies from patient to patient, the carrier 6 may be capable of assuming a range of diameters between the compressed diameter 22 and the maximum diameter 21, as shown in FIG. 2.

The carrier 6 may be characterized by its length 23 along the axis of the elongated shaft 2 or control wire 19. As the carrier 6 expands, its diameter 21 increases and its length 23 decreases. That is, when the carrier 6 expands, its distal end moves axially towards its proximal end. Accordingly, the expanded length 23 is shorter than the unexpanded or natural, or collapsed or compressed, length. In some embodiments, only the proximal end or only the distal end of the carrier 6 is fixedly coupled to the elongated shaft 2. In such a configuration, the distance between the proximal end and the distal end of the carrier 6 changes as the carrier 6 moves between the expanded and collapsed configurations.

The dimensions of the carrier 6 are influenced by its physical characteristics and its configuration (e.g., expanded vs unexpanded), which in turn may be selected with blood vessel geometry in mind. The expanded configuration length 23 of the carrier 6 is less than the corresponding or counterpart length 23 in the compressed configuration. In some embodiments, the expanded configuration length 23 may be less than about 50%, 55%, 60%, 65%, 70%, 75%, 80%, 85%, or 90% of the corresponding or counterpart compressed length 23. Further, in some embodiments, the expanded configuration diameter 21 may be at least 1.2×, 1.25×, 1.5, 1.75×, 2×, 2.25×, 2.5×, 2.75×3×, 3.25×, 3.5×, 3.75×, 4×, 4.25×, 4.5×, 4.75×, 5×, 10×, 15×, 20×, 30× or 40× of the compressed diameter 22.

The axial length 23 of the carrier 6 may be selected to be no longer than a patient's target blood vessel. A blood vessel may constrict, dilate or move in response to blood flow changes or changes in a patient's breathing, etc. The carrier 6 may be selected to be used in conjunction with a particular blood vessel lumen diameter, taking into account that this lumen diameter may change (e.g., up to 20%) during the time that the carrier 6 is in place. As such, the largest diameter 21 of the carrier 6 may be sufficiently oversized relative to the blood vessel to allow for additional expansion during use In one embodiment, the largest diameter 21 may be at least 1.2×, 1.5×, or 2× an estimated lumen diameter of the targeted blood vessel. In addition, stable contact with the blood vessel is facilitated by the contact force of the carrier 6 against the blood vessel wall. This contact force is influenced by the materials and construction of the carrier 6. The carrier 6 may be fabricated with super-elastic material such as nickel titanium alloy (nitinol) or composite nitinol with polymer coating for insulation.

Referring to FIG. 1C and 2, the carrier 6 may carry two or more therapeutic members 7 for intravascular treatment. The therapeutic member 7 may be for example an electrode or a heating element, which is configured to deliver energy such as electrical energy, radiofrequency (RF) electrical energy, pulsed electrical energy, and thermal energy to a target blood vessel after being advanced via a catheter along a percutaneous transluminal path. For example, an energy generator 8 may supply a continuous or pulsed RF electric field to the therapeutic member 7. Although a continuous delivery of RF energy is desirable, the application of RF energy in pulses may allow the application of relatively higher instantaneous power (e.g., higher power), longer or shorter total duration times, and/or better controlled intravascular therapy. Pulsed energy may also allow for the use of a smaller therapeutic member 7.

For example, the purposeful application of energy to tissue by therapeutic member(s) 7 may induce one or more desired thermal heating effects on localized regions of the blood vessel and adjacent regions thereof. The thermal heating effects can include both thermal ablation and non-ablative thermal alteration or damage (e.g., via sustained heating and/or resistive heating). Desired thermal heating effects may include raising the temperature of target tissue above a desired threshold to achieve non-ablative thermal alteration, or above a higher temperature to achieve ablative thermal alteration. For example, the target temperature can be above body temperature (e.g., approximately 37° C.) but less than about 45° C. for non-ablative thermal alteration, or the target temperature can be about 45° C. or higher (such as 60° C.) for the ablative thermal alteration.

When therapeutic members 7 are employed, they may function, for example deliver power, independently (i.e., may be used in a monopolar fashion), either simultaneously, selectively, or sequentially, and/or may deliver power between any desired combination of the members 7 (i.e., may be used in a bipolar fashion). Furthermore, the doctor optionally may be permitted to choose which therapeutic member(s) 7 are used to function medically, such as power delivery in order to form highly customized lesion(s) within the blood vessel, as desired. For example, an RF electric field causes lesion formation via resistive heating of tissue exposed to the electric field. As will be described in more details, the therapeutic member 7 is mounted or integrated into the carrier 6. As the carrier 6 is expanded, the therapeutic member 7 is placed in contact with the wall of a blood vessel. The carrier 6 ensures the contact force of the therapeutic member 7 does not exceed a maximum force, thus advantageously providing a more consistent contact force that may allow for more consistent lesion formation.

Referring back to FIG. 1C, the energy source or energy generator 8 (e.g., a RF energy generator) may be configured to generate a selected form and magnitude of energy for delivery to the target treatment site via therapeutic member 7. The energy generator 8 can be electrically coupled to the catheter apparatus 1 via a cable 9. A control mechanism (not shown), such as foot pedal, may be connected (e.g., pneumatically connected or electrically connected) to the energy generator 8 to allow the doctor to initiate, terminate and, optionally, adjust various operational characteristics of the energy generator, for example, power delivery. The energy generator 8 can be configured to deliver the treatment energy via an automated control algorithm and/or under the control of the doctor. In addition, the energy generator 8 may include one or more evaluation or feedback algorithms to provide feedback to the doctor before, during, and/or after the intravascular treatment. The generator 8 may be part of a device or monitor that may include processing circuitry, such as a microprocessor. The processing circuitry may be configured to execute stored instructions relating to the control algorithm. The monitor may be configured to communicate with the catheter apparatus 1 to control power to the therapeutic member 7 and/or to obtain signals from the therapeutic member 7 or any associated sensors within or outside the therapeutic assembly 70. The monitor may be configured to provide indications of power levels or sensor data, such as audio, visual or other indications, or may be configured to communicate the information to another device.

In some embodiments, the catheter apparatus 1 may be configured to provide delivery of a monopolar electric field via the therapeutic member 7 (e.g. an electrode). In such embodiments, a skin electrode or surface electrode 40 (as shown in FIG. 1C) may be electrically connected to the energy generator 8 and attached to the exterior of the patient, and may function as a neutral or dispersive electrode during the intravascular treatment.

Figure 3:
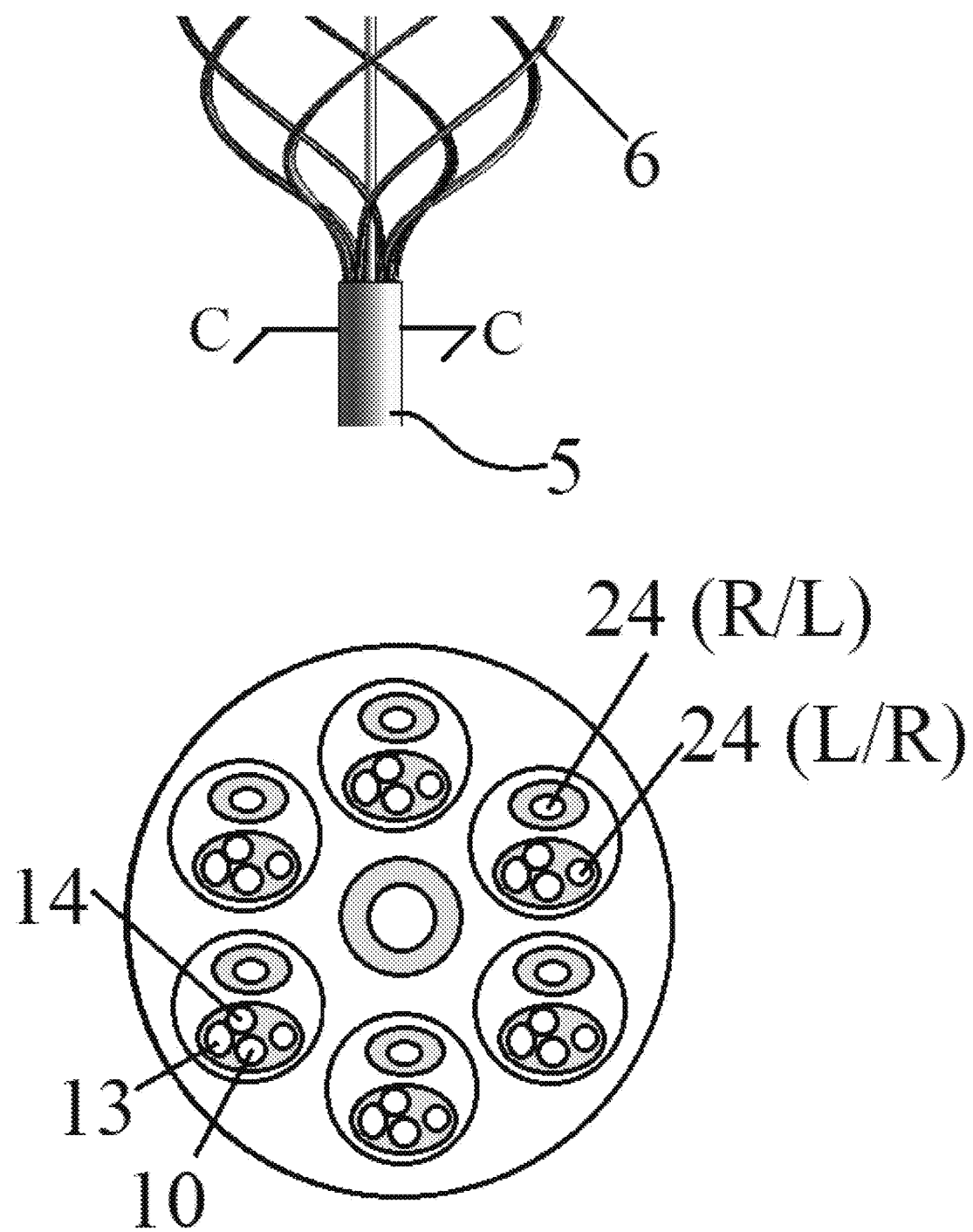
FIG. 3 is a cross-sectional view along C-C of the elongated shaft near the carrier used in an exemplary embodiment.

As shown in FIG. 3, at least one supply wire 10 (such as RF wire 10) passes along the elongated shaft 2 or through a lumen in the elongated shaft 2 to the therapeutic member 7 and transmits the treatment energy from the energy source/generator 8 to the therapeutic member 7.

Figure 4:
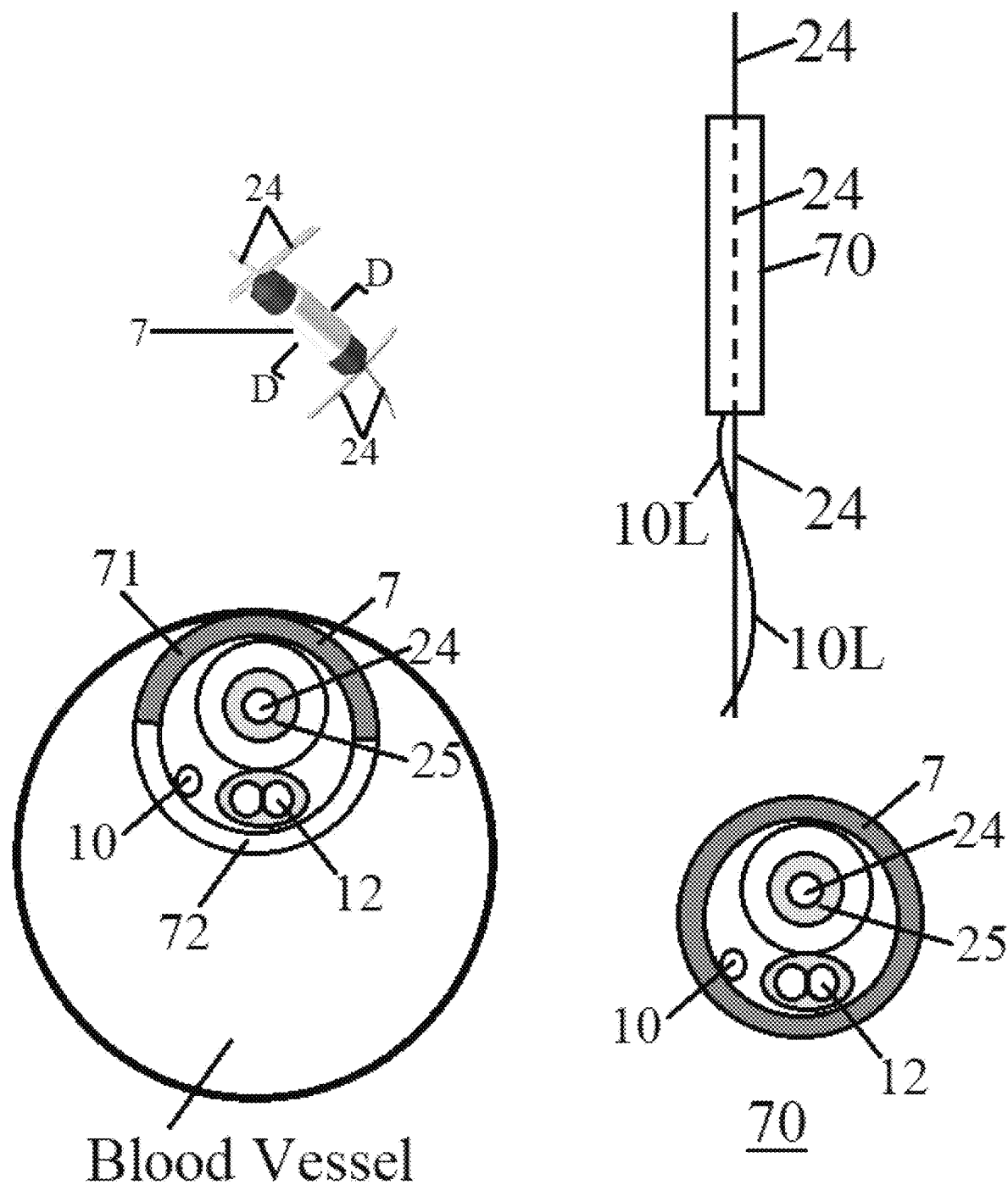
FIG. 4 is a cross-sectional view along D-D of a therapeutic assembly and its position and orientation in a blood vessel.

With reference to FIG. 4, one or more sensors measuring temperature (e.g., thermocouple 12, thermistor, etc.), impedance, pressure, optical, flow, chemical or other parameters, may be located proximate to the therapeutic member 7, e.g. within the therapeutic assembly 70 (i.e. as a part of the therapeutic assembly 70), or not within the therapeutic assembly 70 (i.e. not a part of the therapeutic assembly 70). For example, a total of two supply wires such as thermocouple wires 13 and 14 as shown in FIG. 3 may be included, in which both wires 13 and 14 could transmit the signal from the sensor such as the thermocouple 12, and one wire 13 or 14 could serve dual purpose and also convey RF energy to the therapeutic member 7 (e.g. a RF electrode) without a separate RF wire 10. Alternatively, both wires 13 and 14 could transmit energy to the therapeutic member 7 (e.g. a RF electrode) without a separate RF wire 10.

In various embodiments, energy delivery may be controlled and monitored via data collected with the sensor(s), such as temperature sensors (e.g., thermocouples, thermistors, etc.), impedance sensors, pressure sensors, optical sensors, flow sensors, chemical sensors, etc., which may be incorporated into or on the therapeutic member 7, e.g. within the therapeutic assembly 70, the carrier 6, and/or in/on adjacent areas on the distal portion 5. A sensor may be incorporated into the therapeutic assembly 70 with the therapeutic member 7 in a manner that specifies whether the sensor(s) are in contact with tissue at the treatment site and/or are facing blood flow. It is important to specify temperature sensor placement relative to tissue and blood flow, since a temperature gradient across the electrode from the side facing blood flow to the side in contact with the vessel wall may be up to about 15° C. (for platinum-iridium electrodes). For gold electrodes, this temperature gradient can be around, for example, 1-2° C. In some embodiments, the temperature gradient can vary based, at least in part, on the electrode configuration/material. Significant gradients across the electrode in other sensed data (e.g., flow, pressure, impedance, etc.) can also take place.

The sensor(s) may, for example, be incorporated on or near the side of the therapeutic member 7 that contacts the vessel wall at the treatment site during power and energy delivery or may be incorporated otherwise, such as on the opposing side of the therapeutic member 7 that faces blood flow during energy delivery, and/or may be incorporated within any suitable regions of the therapeutic member 7 (e.g., distal, proximal, quadrants, etc.). In some embodiments, multiple sensors may be provided at multiple positions along the therapeutic member 7, the therapeutic assembly 70, or carrier 6, and/or relative to blood flow. For example, a plurality of circumferentially and/or longitudinally spaced sensors may be provided. In one embodiment, a first sensor may face the vessel wall during treatment, and a second sensor may face the blood flow.

Additionally or alternatively, various microsensors may be used to acquire data corresponding to the therapeutic member 7, the vessel wall and/or the blood flowing across the therapeutic member 7. For example, arrays of micro thermocouples and/or impedance sensors may be implemented to acquire data along the therapeutic member 7 or other parts of the carrier 6. Sensor data may be acquired or monitored prior to, simultaneous with, or after the delivery of energy or in between pulses of energy. The monitored data may be used in a feedback loop to better control therapy, e.g., to determine whether to continue or stop treatment, and it may facilitate controlled delivery of therapy with an increased or reduced power, or a longer or shorter duration.

When catheter apparatus 1 is being used, the distal portion 5 of the elongated shaft 2 as well as the carrier 6 may be moved through an intravascular path by following a path defined by a guide catheter, a guide wire, or a sheath, such as from a percutaneous access site in the femoral, brachial, radial, or auxiliary artery, to a targeted site within the blood vessel. A section of the proximal portion 3 of the shaft 2 is exposed externally of the patient. By manipulating the proximal portion 3 of the shaft 2 from outside the intravascular path (e.g., via the handle assembly 4), the doctor may advance the shaft 2 through the sometimes tortuous intravascular path and remotely manipulate or actuate the distal portion 5 of the shaft 2. Image guidance, e.g., computed tomography (CT), fluoroscopy, intravascular ultrasound (IVUS), optical coherence tomography (OCT), any other suitable guidance modality, or combinations thereof, may be used to aid the doctor's manipulation. In some embodiments, image guidance components (e.g., IVUS, OCT) may even be incorporated into the catheter apparatus 1 itself. After the carrier 6 is adequately positioned in the blood vessel, it can be expanded or otherwise deployed using the handle 4 or other suitable means until the therapeutic member 7 such as RF electrodes are in stable contact with the inner wall of the blood vessel.

Referring back to FIG. 2, the compressed, collapsed or delivery configuration of the carrier 6 facilitates insertion and/or removal of the catheter apparatus 1 and, in certain embodiments, repositioning of the catheter apparatus 1 within the blood vessel. In the collapsed configuration, the carrier 6 is sized and shaped to fit within the blood vessel and has a diameter that is less than a blood vessel lumen diameter. The carrier 6 is expected to provide stable contact of the therapeutic member 7 with the inner wall of a vessel without occluding the blood flow within the vessel. As the carrier 6 is fabricated or woven from wires, blood can flow through the carrier 6 via interstices 15, the structure of which will be described in more details.

Figure 5:
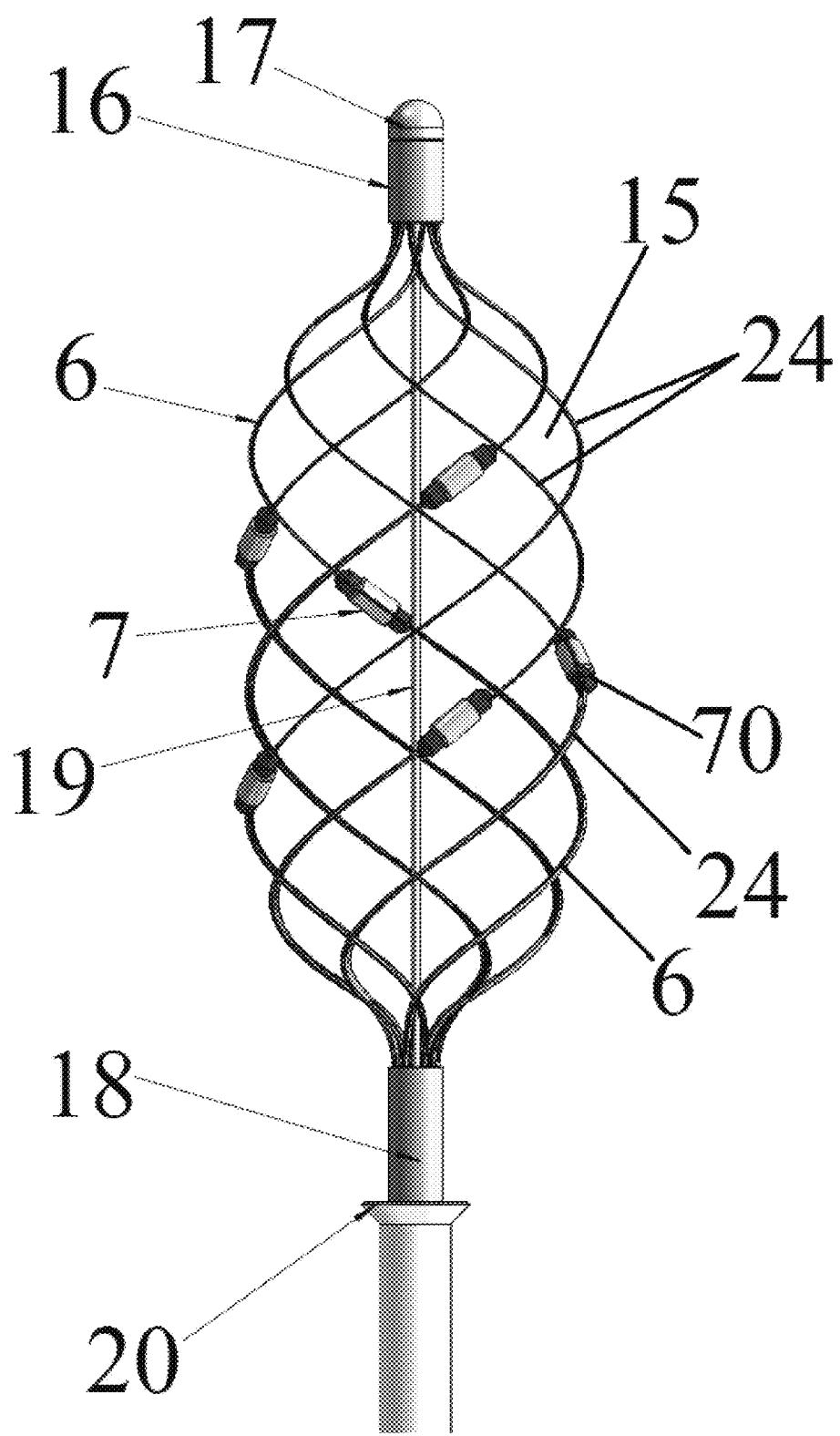
FIG. 5 depicts the, specific structure of a carrier used, in an exemplary embodiment.

Referring now to FIG. 5, the distal end of the carrier 6 may be coupled to an end piece 16 (e.g., a collar, shaft, or cap) having a rounded distal portion 17 to facilitate atraumatic insertion of the carrier 6 into a blood vessel. Alternatively, a rounded part that is radiopaque (or visible to X-ray imaging such as CT) may replace the rounded distal portion 17 to facilitate atraumatic insertion of the carrier 6 and to track the location of the carrier 6. The proximal end of the carrier 6 may be connected to, or coupled to, the elongated shaft 2 using a multi-lumen coupling 18. Coupling 18, for example, may be an integral end of the elongated shaft 2 (e.g., may not be a separate piece) or may be a separate piece that is associated with the distal region of the elongated shaft 2. The coupling 18 may be formed from the same type of material as the elongated shaft 2, or may be formed from a different material. In one embodiment, the coupling 18 may be formed from a collar, such as a radiopaque band, that surrounds and secures the carrier 6 to an exterior surface of the elongated shaft 2.

The elongated shaft 2, the coupling 18, the carrier 6, and the end piece 16 may include passages sized and shaped to accommodate a control wire or pull/push wire 19 that is fixed to the distal end of the carrier 6 or the end piece 16 and passes through the elongated shaft 2 to the proximal portion 3 of the elongated shaft 2. The control wire 19 facilitates the expansion and/or contraction of the carrier 6 when it is pulled or pushed to shorten or lengthen the carrier 6. For example, pulling (i.e., an increase in tension) the control wire 19 proximally relative to the shaft 2 may trigger expansion of the carrier 6 by drawing end piece 16 closer to coupling 18. Conversely, pushing (i.e., an increase in compression) the control wire 19 distally relative to shaft 2 may lengthen the carrier 6 to a compressed configuration by axially spreading apart end piece 16 and coupling 18. It will be understood that either the shaft 2 or the control wire 19 may be held in fixed position with respect to the patient while the other element is translated to create the relative movements described above. In some embodiments the carrier 6 has elastic or super-elastic shape memory properties such that when force is removed, the carrier 6 elastically returns to a relaxed state or a natural state as shown in FIG. 2. Force may be applied by the control wire 19 to deform the carrier 6 into one state, and when force is removed, the mesh carrier 6 returns to its relaxed state. For example, a relaxed or "natural" state of the carrier 6 may be a half-way expanded configuration as shown in FIG. 2, and the control wire 19 may be pushed to lengthen the carrier 6 and reduce its diameter, placing it in a collapsed or "compressed" configuration as shown in FIG. 2. Alternatively, a relaxed state of the carrier 6 may be a collapsed or compressed configuration and the control wire 19 may be pulled (tension applied) to shorten the carrier 6 and increase its diameter, placing it in an expanded configuration. In some embodiments, the control wire 19 may be a solid or stranded wire or cable made from a metal or polymer. In other embodiments, the control wire 19 may be a hollow tube that can be passed over a guide wire to facilitate insertion through an intravascular path to a targeted site in the blood vessel.

As shown in FIG. 5, the carrier 6 includes structural elements, e.g., wires 24 (or strands, filaments or fibers) arranged to define interstices 15 (or interstitial spaces) therebetween. Because the change in diameter and axial length of the carrier 6 may involve realignment of wires 24 and variations of the geometry of the interstices 15, the makeup of the wires 24 and the geometry of the interstices 15 may at least in part define how much the diameter and length of the carrier 6 change as a result of its configuration changes.

The wires 24 may be formed from biocompatible metals, polymers, or composites. For example, suitable metals can include stainless steel, spring steel, cobalt chromium, gold, platinum, platinum-iridium, stainless steel, or combinations thereof. In one particular embodiment, the carrier 6 may be composed of nitinol with gold plating to enhance radiopacity and/or conductivity. Suitable polymer materials can include, for example, polyethylene terephthalate (PET), polyamide, polyimide, polyethylene block amide copolymer, polypropylene, or polyether ether ketone (PEEK) polymers. In some embodiments, the carrier 6 may be a combination of electrically conductive and nonconductive materials.

In some embodiments, the carrier 6 may be formed at least in part from radiopaque materials that are capable of being imaged fluoroscopically to allow a doctor to determine if the carrier 6 is appropriately placed and/or deployed in the blood vessel. Radiopaque materials may include barium sulfate, bismuth trioxide, bismuth subcarbonate $(BiO)_2CO_3$, powdered tungsten, powdered tantalum, or various formulations of certain metals, including gold and platinum, and these materials may be directly incorporated into the wires 24 or may form a partial or complete coating of the carrier 6.

The carrier 6 may be designed to apply a desired outward radial force to a blood vessel wall when inserted and expanded to contact the inner surface of the wall. The radial force may be selected to avoid injury from stretching or distending, the vessel when the carrier 6 is expanded against the wall within the patient. Radial forces that may avoid injuring the blood vessel yet provide adequate stabilization force may be determined by calculating the radial force exerted on a vessel wall by typical blood pressure. For example, a suitable radial force may be less than about 300 mN/mm (e.g. less than 200 mN/mm). Fibers 24 formed from stiffer materials (e.g. metals) may be thinner relative to fibers 24 formed highly flexible polymers to achieve similar flexibilities and radial force profiles. The outward pressure of the carrier 6 may be assessed in vivo by an associated pressure transducer.

The carrier 6 with more open structures (e.g., bigger interstices 15, or lower material per square inch ratios) may have less radial stiffness and strength than more closed structures (smaller interstices 15, or high material density structures). The thickness of fibers 24 also affects outward pressure, radial strength and stiffness. Certain secondary processes, including heat treating and annealing, may harden or soften the fiber material to affect strength and stiffness. In particular, for shape-memory alloys such as nitinol, these secondary processes may be varied to give the same starting material different final properties. For example, the elastic range or softness may be increased to impart improved flexibility. The secondary processing of shape memory alloys influences the transition temperature, i.e., the temperature at which the structure exhibits a desired radial strength and stiffness. This temperature may be set at normal body temperature (e.g. 37° C.).

The carrier 6 may be braided, knit, or woven to form a conformable structure (e.g., a tubular, barrel-shaped, parachute-shaped, or spherical structure) through which fluids may pass. In embodiments, the carrier 6 may include 4-48 fibers. It should be understood'that fiber 24 may be formed from a single filament (monofilament) or by a plurality of filaments twisted or otherwise grouped together to form a multifilar fiber. In addition, the carrier 6 may be characterized by its braid pitch, which may be between 1-10 picks (i.e., windings) along its axial length. In preferred embodiments, the carrier 6 may be helically braided with right-handed helix wires and left-handed helix wires) into a generally ovoid, tubular, barrel, or other shaped structure.

In some embodiments, the carrier 6 may be generally symmetrical and coaxial with respect to the elongated shaft 2 or control wire 19. However, it is also contemplated that the carrier 6 may conform to any irregularities in the blood vessel (e.g. a shape of fortune cookie), which may be assessed by imaging or other techniques. For example, particular sizes and types of carrier 6 may be used in conjunction with a patient's particular anatomic features, For some patients, it may be desirable to configure the therapeutic member(s) 7 in such a manner that they can create either a single lesion or a pattern of multiple focal lesions that are spaced apart circumferentially and/or axially along the longitudinal axis of the blood vessel. A single focal lesion with desired longitudinal and/or circumferential dimensions, one or more full circumferential lesions, multiple circumferentially spaced focal lesions at a common longitudinal position, spiral-shaped lesions, interrupted spiral lesions, generally linear lesions, and/or multiple longitudinally spaced focal lesions along a line parallel to the axis of the blood vessel alternatively or additionally may be created. In other embodiments, the therapeutic member(s) 7 may be used to create lesions having a variety of other geometric shapes or patterns.

Depending on the size, shape, and number of the therapeutic member(s) 7, the lesions created may be circumferentially spaced around the blood vessel, either in a single transverse plane or the lesions may also be spaced apart longitudinally. In some embodiments, it is desirable for each lesion to cover at least 10% of the vessel circumference. It is also desirable that each lesion be sufficiently deep to penetrate into and beyond the adventitia. However, lesions that are too deep run the risk of interfering with non-target tissue and tissue structures, and therefore a controlled depth of treatment is also desirable.

In general embodiments, the therapeutic member(s) 7 may be circumferentially repositioned relative to the blood vessel during treatment. This angular repositioning may be achieved, for example, by compressing the carrier 6 and rotating the elongated shaft 2 via handle assembly 4. In addition to the angular or circumferential repositioning of the therapeutic member(s) 7, it/they optionally may also be repositioned along the lengthwise or longitudinal dimension of the blood vessel. This longitudinal repositioning may be achieved, for example, by translating the elongated shaft 2 via the handle assembly 4, and may occur before, after, or concurrently with angular repositioning of the therapeutic member(s) 7. Repositioning the therapeutic member(s) 7 in both the longitudinal and angular dimensions places it/them in contact with the interior wall of the blood vessel at a second treatment site. RF Energy may then be delivered via the therapeutic member 7 to form a second focal lesion at this second treatment site. For embodiments in which multiple therapeutic members 7 are associated with the carrier 6, the initial treatment may result in two or more lesions, and repositioning may allow additional lesions to be created. One or more additional focal lesions optionally may be formed via additional repositioning of the carrier. In preferred embodiments, the carrier 6 carries a sufficient number of therapeutic member 7 (e g. RF electrodes), and it does not have to be selectively repositioned within the blood vessel to provide a number of locations for e.g. RF energy delivery.

In certain embodiments, the lesions created via repositioning of the carrier 6 are circumferentially and longitudinally offset from the initial lesion(s) about the angular and lengthwise dimensions of the blood vessel, respectively. The composite lesion pattern created along the blood vessel by the initial energy application and all subsequent energy applications after any repositioning of the therapeutic member(s) 7 may effectively result in a discontinuous lesion (i.e., it is formed from multiple, longitudinally and angularly spaced treatment sites).

Sometimes, it may be desirable to configure the therapeutic member(s) 7 in such a manner to create a composite lesion pattern, as viewed from a proximal or distal end of the vessel, to extend at least approximately all the way around the circumference of the blood vessel under treatment. In other words, each formed lesion covers an arc of the circumference; and each of the lesions, as viewed from an end of the vessel, abut or overlap adjacent lesions to create a virtually circumferential lesion. The formed lesions defining an actual circumferential lesion lie in a single plane perpendicular to a longitudinal axis of the blood vessel. A virtually circumferential lesion is defined by multiple lesions that may not all lie in a single perpendicular plane, although more than one lesion of the pattern can be so formed. At least one of the formed lesions comprising the virtually circumferential lesion is axially spaced apart from other lesions.

For example, a cylindrical carrier 6 having therapeutic members 7 affixed to wires 24 in a helical pattern such that therapeutic members 7 are circumferentially and axially offset from one another. The circumferential offset arcs, or corresponding radial angles, may be selected so that when energy is applied to the blood vessel via therapeutic members 7, a roughly helical lesion pattern is formed therein. Depending on the number and positioning of the therapeutic members 7 selectively mounted on wires 24, a helical lesion pattern with any desired number of turns (e.g. 1, 2, 3 or more) may be formed using only a single RF energy application. In other embodiments, the therapeutic members 7 may have a variety of different arrangements relative to each other (e.g., linear, interrupted helix, continuous helix).

In a non-limiting example, the therapeutic members 7 are configured in such a manner to create a virtually circumferential lesion comprising six lesions created in a single helical pattern along the blood vessel, and each lesion spans an arc extending along at least one sixth (or 60 degree) of the vessel circumference such that the resulting pattern of lesions completely encompasses the vessel circumference, when viewed from an end of the vessel. In other examples, however, a virtually circumferential lesion can comprise a different number of lesions.

The axial distances between axially adjacent therapeutic members 7 may be selected so that the edges of the lesions formed by each individual therapeutic member 7 on the blood vessel wall 55 are either overlapping or non-overlapping. The axial distance may be about 2 mm to about 1 cm.

In a particular embodiment, the axial distance may be in the range of about 2 mm to about 5 mm. In another representative embodiment, the axially adjacent therapeutic members 7 may be spaced apart about 10-50 mm.

Therapeutic member(s) 7 may be coupled to leads 10L, which may be e.g. a part of RF wire 10, or electrically connected to RF wire 10. The leads 10L may be separate from the carrier 6, or may be loosely or tightly coupled to, adhered to, wrapped around, or integrated into to the carrier 6 (e.g. around/on/with/to a wire 24) to prevent twisting or kinking of the leads. In particular embodiments, to facilitate the stable contact of the therapeutic member(s) 7 to the blood vessel, the therapeutic assembly 70 may be coupled to carrier 6 by weaving lead(s) into the wires 24 of the mesh or threading leads through interstices in the mesh of carrier 6. At least a part of the therapeutic member(s) 7 is positioned on an exterior surface of carrier 6. The positioning of the therapeutic member(s) 7 on the exterior surface may be associated with a desired lesion pattern. Alternatively, as shown in FIGS. 2 and 5, the therapeutic assembly 70 may be directly coupled to the wire 24. The therapeutic assembly 70 is coupled to wire 24, for example via adhesion or threading a wire 24 through an internal bore 25, as shown in FIG. 4.

The therapeutic member 7 may be in the form of an electrically conductive tube. As shown in FIG. 4, the tube electrode 7 may be wound about (or wrapped around) wire 24. In other words, a wire 24 inserts into and passes through the tube electrode 7. For example, six tube electrodes 7 may form a loose-pitch or tight-pitch "dotted", interrupted or discontinuous helix. Regions of the tube electrode 7 that do not contact the blood vessel wall may contribute to cooling of the electrode. Alternatively, as shown in FIG. 4, only portion 71 of the tube electrode 7 may be electrically conductive with the blood vessel wall tissue. That is, the tube electrode 7 can include insulated portion 72 and uninsulated portion 71 in which the insulation is removed. For example, the flow of blood over the portion 72 (which is not contacting vessel wall) provides conductive and convective cooling of a RF electrode 7, thereby carrying excess thermal energy away from the interface between the vessel wall and electrode 7. Electrode cooling can be alternatively or additionally achieved by injecting or infusing cooling fluids such as saline (e.g., room temperature saline or chilled saline) over the electrode and into the blood stream. It may also be desirable to provide enhanced cooling by inducing additional native blood flow across the carrier 6. For example, techniques may be implemented by the doctor to increase perfusion through the target blood vessel or to the carrier 6. These techniques include positioning partial occlusion elements (e.g., balloons) within upstream vascular bodies such as the aorta, or within a portion of the target blood vessel to improve flow across the carrier 6. Because cooling of the electrode 7 is mediated by blood flow, improved cooling may be achieved by redirecting a faster blood flow into the target blood vessel or into the carrier 6 so that the blood flowing around the electrode 7 is relatively faster. Sometimes, without a proper cooling, resistive heating of the tissue may be too aggressive and not enough excess thermal energy is being carried away, resulting in excessive heat generation and increased potential for stenotic injury, thrombus formation and undesirable lesion size.

The therapeutic member 7 may be sized and configured to contact an internal wall of the blood vessel during the treatment. For example, the therapeutic member 7 may take the form of an electrode sized and configured to apply an electrical field of RF energy from the energy generator 8 to a vessel wall. As described above, the electrode 7 may be operated in a monopolar or unipolar mode. In this arrangement, a return path for the applied RF electric field is established, e.g., by an external dispersive electrode or skin electrode 40 (as shown in FIG. 1), also called an indifferent electrode or neutral electrode. The monopolar application of RF electric field energy serves to ohmically or resistively heat tissue in the vicinity of the electrode 7. The application of the RF electrical field thermally injures tissue. For example, a treatment objective may be to thermally induce neuromodulation (e.g., necrosis, thermal alteration or ablation) in the targeted neural fibers. The thermal injury forms a lesion in the vessel wall. Alternatively, a RF electrical field may be delivered with an oscillating intensity that does not thermally injure the tissue whereby neuromodulation in the targeted nerves is accomplished by electrical modification of the nerve signals.

The term "active surface area" of the electrode 7 is defined as the energy transmitting area of the electrode 7 that may be placed in intimate contact against tissue. Too much contact between the electrode and the vessel wall may create unduly high temperatures at or around the interface between the tissue and the electrode, thereby creating excessive heat generation at this interface. This excessive heat may create a lesion that is circumferentially too large. In some instances, too much contact can also lead to small, shallow lesions. Too little contact between the electrode 7 and the vessel wall may result in superficial heating of the vessel wall, thereby creating a lesion that is too small (e.g., <10% of vessel circumference) and/or too shallow.

Figure 6:
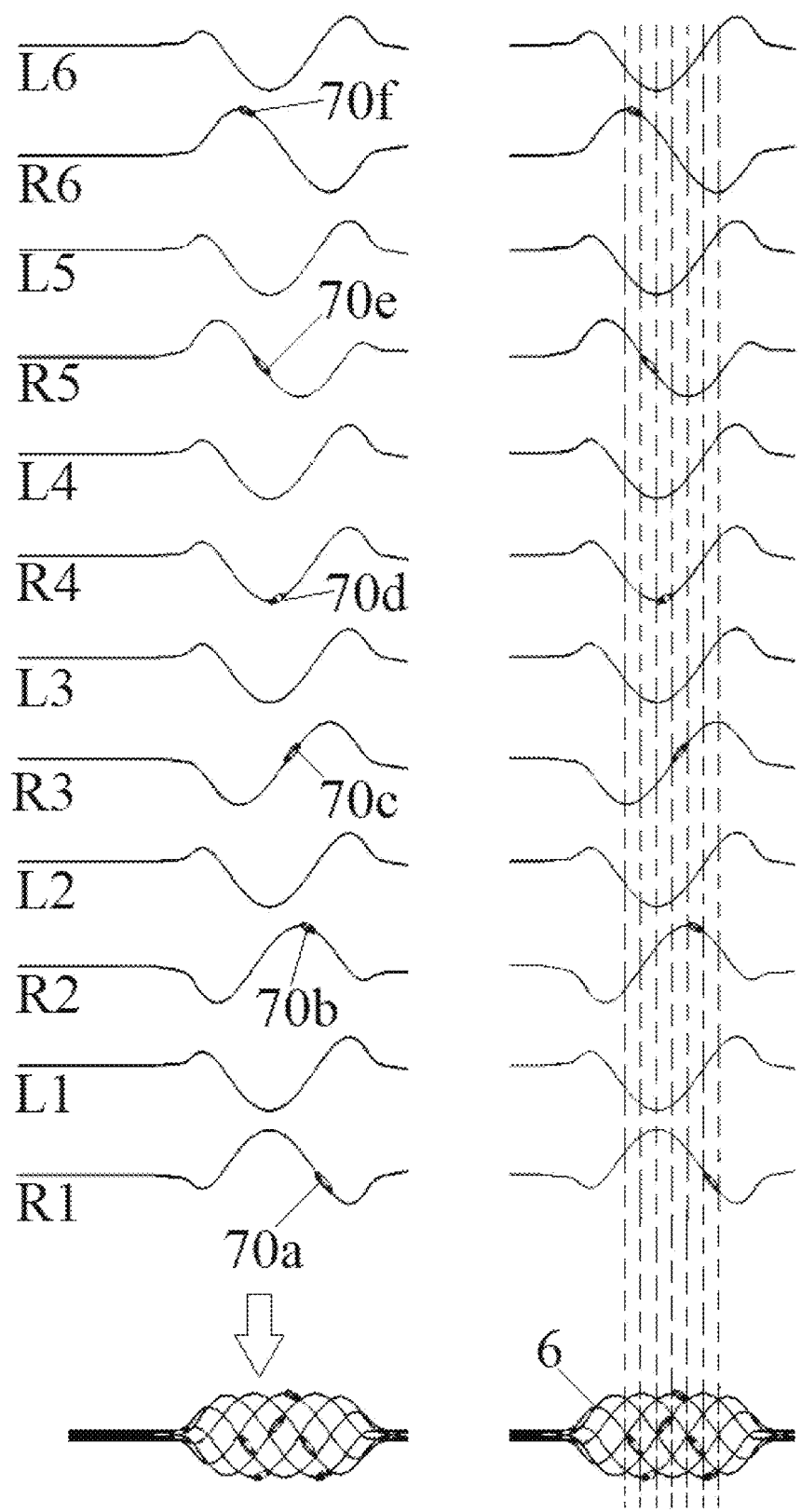
FIG. 6 schematically shows a carrier including right-handed wire helixes and left-handed wire helixes used in an exemplary embodiment.

As described above, the carrier 6 may be helically braided with right-handed helix wires and left-handed helix wires) into a generally ovoid, tubular, barrel, or other shaped structure. In preferred embodiments as shown in FIG. 6, the carrier 6 comprises m (m≥2) right-handed wire helixes such as 6 R-helixes R1~R6 and n (n≥2) left-handed wire helixes such as 6 L-helixes L1~L6. With the line of sight along the helix's axis, if a clockwise screwing motion moves the helix away from the observer, then it is called a right-handed helix, if towards the observer, then it is a left-handed helix. Handedness or chirality (symbolized as R- and L-) is a property of the helix, not of the perspective. A right-handed helix cannot be turned to look like a left-handed one unless it is viewed in a mirror, and vice versa. In some embodiments, the carrier 6 comprises m right-handed wire helixes and n left-handed wire helixes that are plainly or bi-axially woven into a tubular structure, 2≤m≤30 and 2≤n≤30, such as 3≤m≤20 and 3≤n≤20; 4≤m≤15 and 4≤n≤15; 5≤m≤10 and 5≤n≤10. For example, helixes R1~R6 and L1~L6 are plainly or bi-axially woven into carrier 6 with a tubular structure, as shown in FIG. 6.

Figure 7:
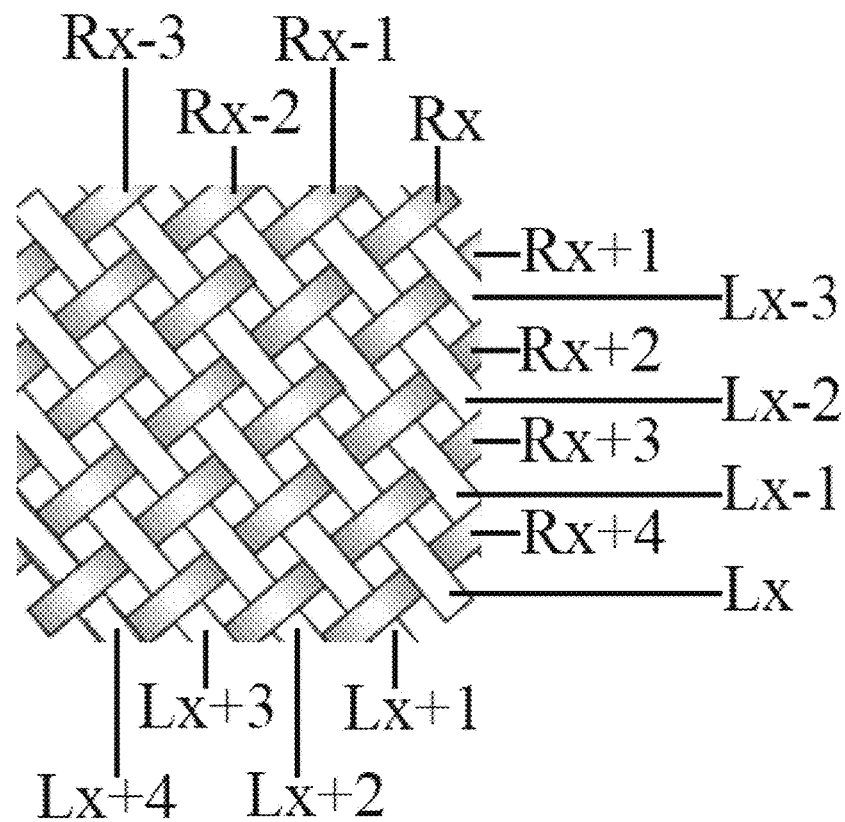
FIG. 7 shows how wires are plainly or bi-axially woven in accordance with an exemplary embodiment of the present invention.
Figure 7:
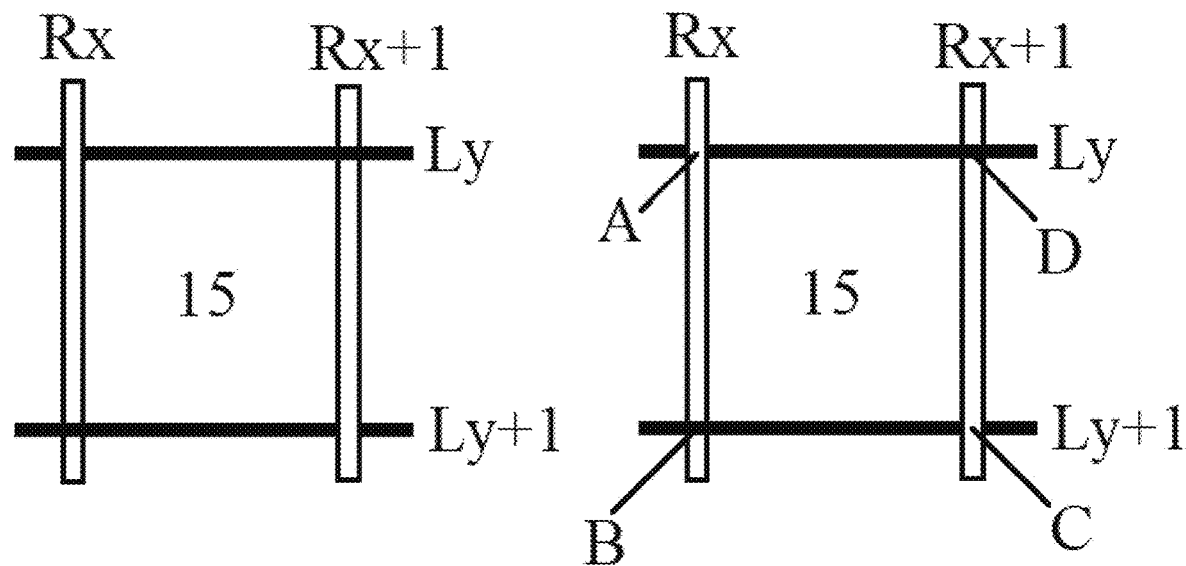

The term "plainly or bi-axially" is defined and explained with reference to FIG. 7. Any right-handed helix wire R (e.g. Rx) is woven into (or between) at least two immediately adjacent left-handed helix wires Ls (e.g. Ly and Ly+1), in such a manner that one L wire (e.g. Ly) is beneath wire R (e.g. Rx), while another L wire which is immediately next to Ly (e.g. Ly+1) is above Rx. In other words, Ly and Ly+1 are located on the opposite sides of wire Rx. A right-handed helix wire Rx+1, that is immediately next to (or adjacent to) wire Rx, is also woven into (or between) two wires Ly and Ly+1, but in an opposite manner to produce an opposite configuration that wire Ly is above wire Rx+1, while wire Ly+1 is beneath Rx+1. By the same token, any left-handed helix wire Ly is woven into at least two immediately adjacent right-handed helix wires Rx and Rx+1, in such a manner that wire Rx is above wire Ly, while wire Rx+1 is below Ly. In other words, Rx and Rx+1 are located on the opposite sides of wire Ly. A left-handed helix wire Ly+1, that is immediately next to (or adjacent to) wire Ly, is woven into two wires Rx and Rx+1, in an opposite manner to produce an opposite configuration that wire Rx is beneath wire Ly+1, while wire Rx+1 is above Ly+1.

In such a pattern, the four wires (Rx, Rx+1, Ly, and Ly+1) will have four intersectional points (or cross-over points) A, B, C and D that are not fixed, and are movable relative to their two corresponding crossed-over wires. For example, point A is moveable relative to wire Rx and/or Ly as wire Rx slides over Ly and/or Ly slides over Rx. Points B, C and D are also moveable for similar reasons and in similar fashions. As a result, the carrier 6 comprises at least one interstice 15 that is defined by four wire helix segments AB, BC, CD and DA selected from two immediately adjacent right-handed wire helixes (Rx and Rx+1) and two immediately adjacent left-handed wire helixes (Ly and Ly+1) that are plainly or bi-axially woven into each other.

Figure 8:
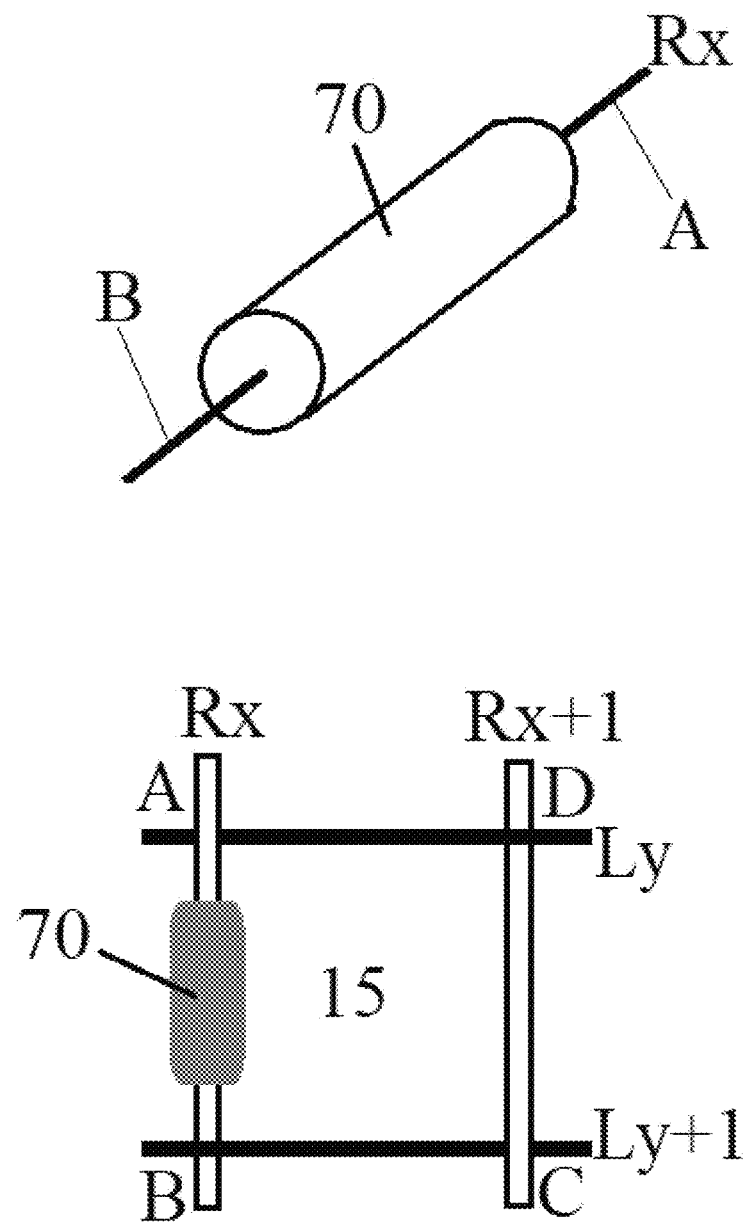
FIG. 8 shows a therapeutic assembly wrapping around a wire helix segment in accordance with an exemplary embodiment.
Figure 9A:
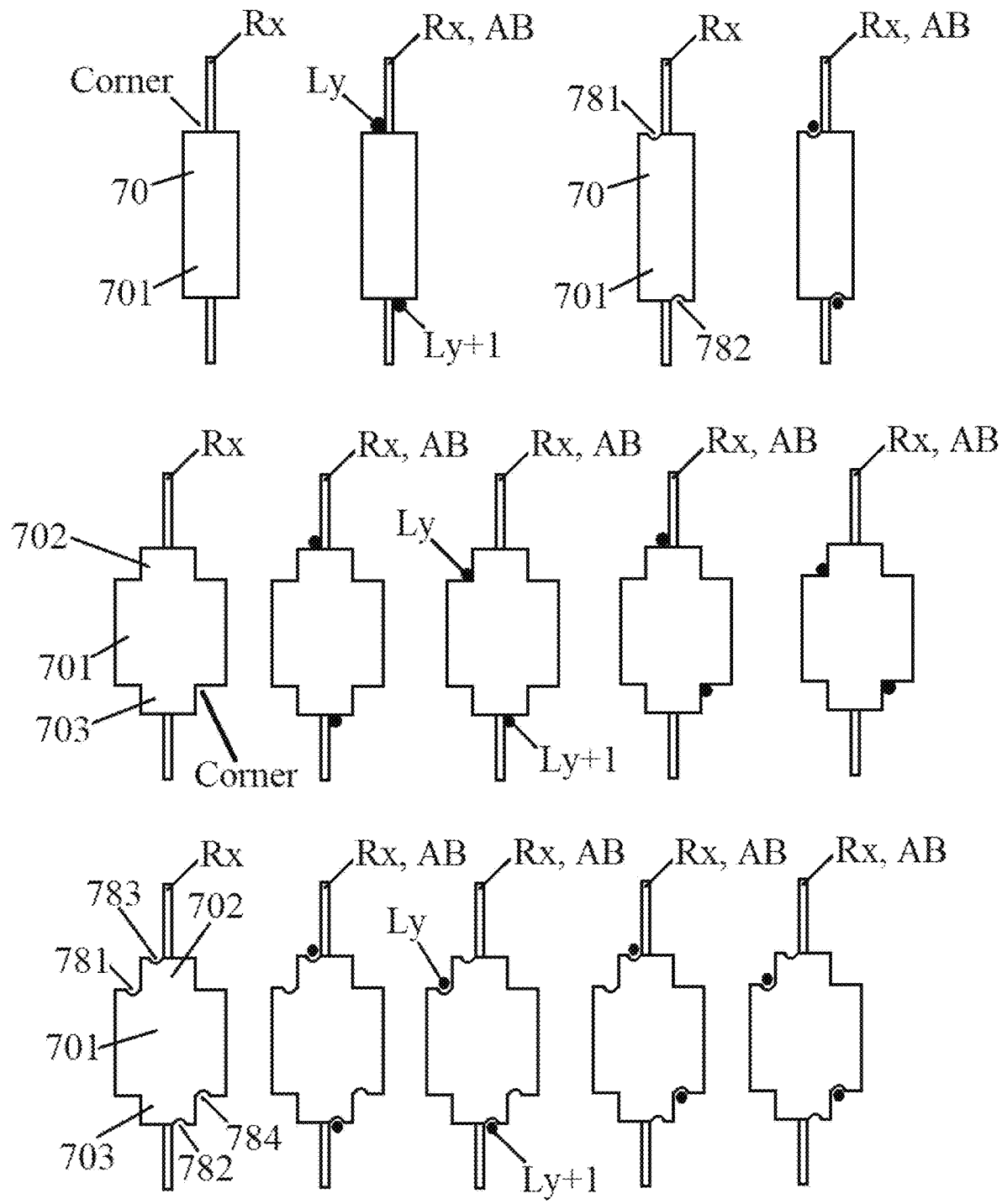
FIG. 9A shows various structures of the therapeutic assembly used in an exemplary embodiment.

As shown in FIG. 8, at least one therapeutic assembly 70 is configured to wrap around at least one of said four wire helix segments AB, BC, CD and DA (e.g. segment AB) to stabilize said at least one interstice 15. The lengths of helix segments AB, BC, CD and DA vary when the carrier 6's shape is being changed. In some embodiments, only one therapeutic assembly 70 wraps around only one of said four wire helix segments AB, BC, CD and DA (e.g. only segment AB) to stabilize the interstice 15, and does not wrap around any one of the other three helix segments (e.g. segments BC, CD and DA). In a preferred embodiment, therapeutic assembly 70 has a rotational axis (e.g. when it has cylinder shape), and wire helix segment AB penetrates through therapeutic assembly 70 approximately along the rotational axis. By "approximately", it means that the distance between the wire helix segment AB and the rotational axis is always less than 50% of the distance between an edge (or a side surface) of therapeutic assembly 70 and the rotational axis, along any plane perpendicular to the rotational axis. In particularly preferred embodiments, m=n=6, and the carrier 6 carries six therapeutic assemblies 70a-70f as shown in FIG. 6, each of which includes an electrode 7 as the therapeutic member 7, providing six electrodes in total. The six electrodes may be configured to create interrupted spiral but full circumferential lesions on internal wall of a target blood vessel, As shown in FIG. 9A, the therapeutic assembly 70 may include a main body 701 such as a single cylinder-shaped body 701, without any terminal bodies. Alternatively, assembly 70 may further include two terminal bodies 702 and 703, both of which may be cylinder-shaped, and the main body 701 may be positioned between the two terminal bodies 702 and 703. In other embodiments, terminal bodies 702 and 703 may have a cone shape, tapering down from the main body 701. The cross-sectional area of the main body 701 along a plane perpendicular to the elongation direction of the wire segment AB being wrapped around is larger than cross-sectional areas of both terminal bodies 702 and 703 along a plane perpendicular to the elongation direction of the wire segment AB being wrapped around, which are larger than a cross-sectional area of the wire segment AB itself along a plane perpendicular to the elongation direction of the wire segment AB. The dimension and shape of terminal body 702 may be the same as, or different from, those of terminal body 703.

As shown in FIG. 9A, all the corner areas formed between the main body 701 (when there is no terminal body) and wire Rx, between the main body 701 and terminal body 702 (if present), between the main body 701 and terminal body 703 (if present), between terminal body 702 (if present) and wire Rx, and between terminal body 703 (if present) and wire Rx may be used to accommodate wires Ly and Ly+1, as long as the plainly or bi-axially woven pattern of R- and L-wires is maintained.

At least one of (preferably all) the two terminal bodies 702/703 if any and the main body 710 may include one or more grooves for snugly accommodating or guiding one or more wire helixes that slide(s) over the wire segment around which the therapeutic assembly wraps. For example, body 701/702/703 can be grooved with grooves 781, 782, 783 and 784 near the corner areas for snugly accommodating sliding wires Ly and Ly+1 in a more stable manner, as shown in FIG. 9A. Wires Ly and Ly+1 can slide over wire Rx using the grooves as guides.

Figure 9B:
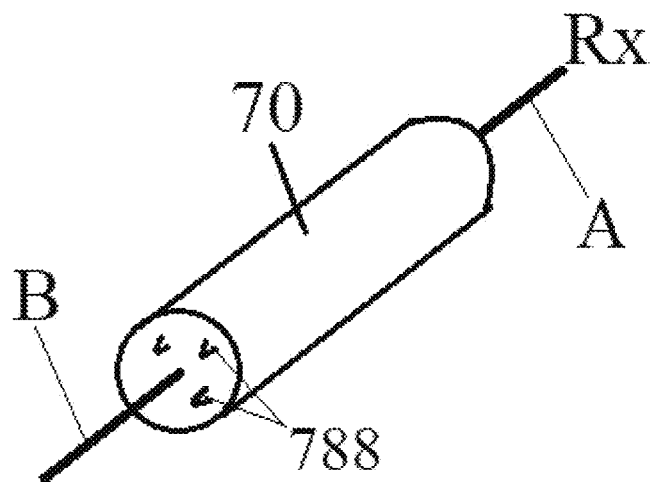
FIG. 9B shows other structures of the therapeutic assembly used in an exemplary embodiment.
Figure 9B:
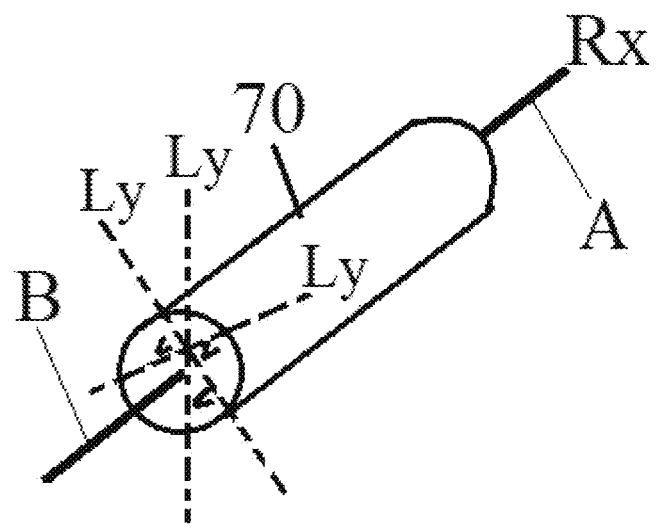

As shown in FIG. 9B, at least one of (preferably all) the two terminal bodies 702/703 if any and the main body 710 may include one, two or more protrusions 788. The gap(s) between segment AB and protrusion(s) 788, and the gap(s) between said protrusion(s) 788 themselves, configured for accommodating or guiding one or more wire helixes Ly or Ly±1 that slide(s) along different directions (represented as the dotted lines Ly) over the wire segment AB around which the therapeutic assembly 70 wraps. When there are three or more protrusions 788, it is preferred that no three protrusions 788 are located along a straight line. As such, we will have as many "Ly guiding directions" as possible.

Figure 10:
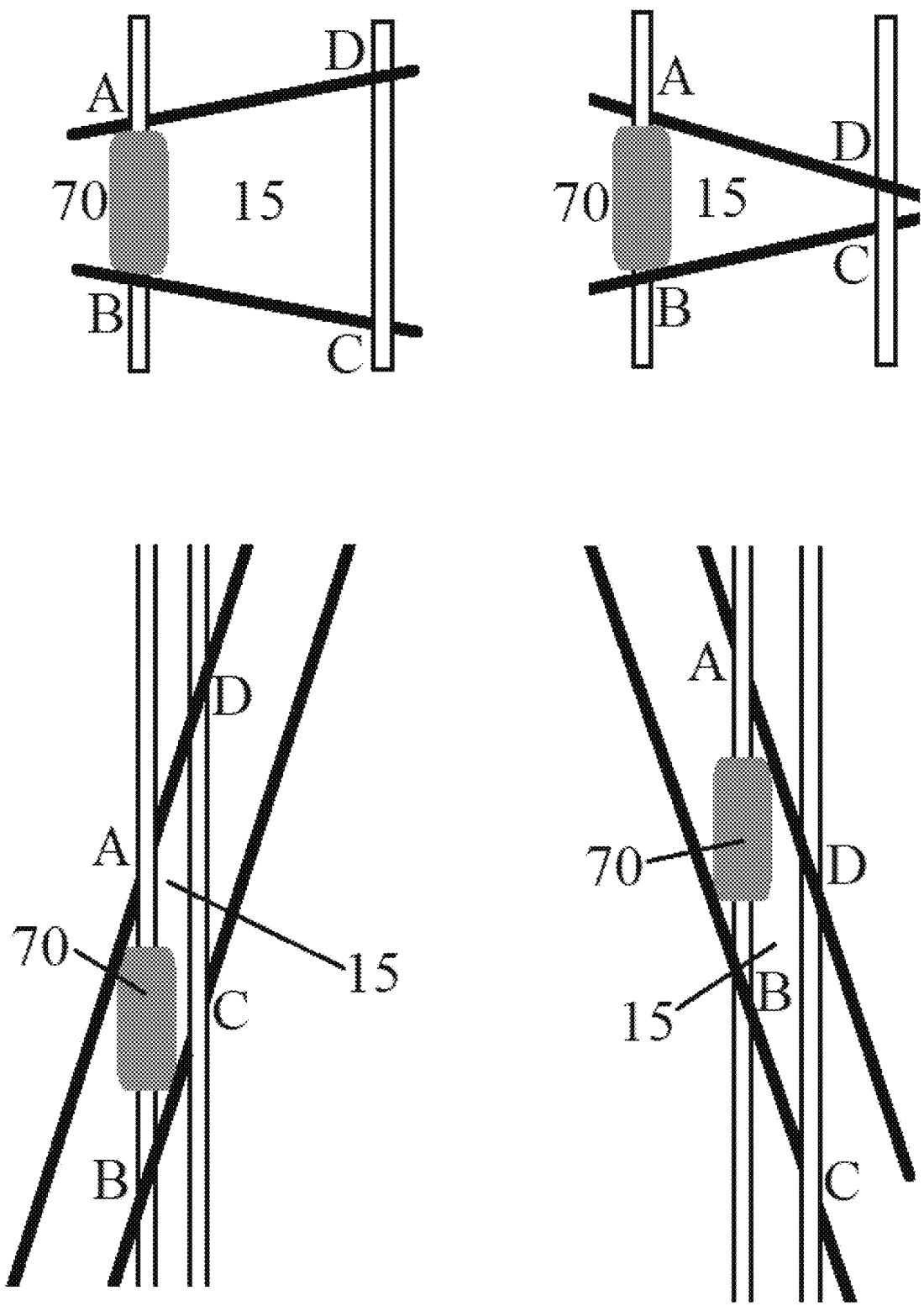
FIG. 10 shows various geometries of the interstice stabilized by a therapeutic assembly in accordance with an exemplary embodiment.

As a result, length of the wire segment AB being wrapped around may now be controlled, depending on where wires Ly and Ly+1 sit, to be equal to, or longer than, the main body 701's length along the elongation direction of the wire segment AB, with or without terminal bodies. It may also be controlled to be equal to, or longer than, the main body 701's length combined with the length of only one of the two terminal bodies (702 or 703) along the elongation direction of the wire segment AB. Alternatively, the length of the wire segment AB being wrapped around may be controlled to be equal to, or longer than, the main body 701's length combined with total length of both two terminal bodies (702 and 703) along the elongation direction of the wire segment AB. As such, various minimal lengths of the wire segment AB may be maintained to be greater than a certain positive value when the carrier 6 is being expanded, compressed, or moved along a curved blood vessel, as shown in FIG. 10. With such minimal lengths of the wire segment AB, wires Ly and Ly+1 are prevented from entangling with each other, and the regular shape of the carrier 6 may be quickly recovered after the carrier is seriously bent or distorted.

Figure 11:
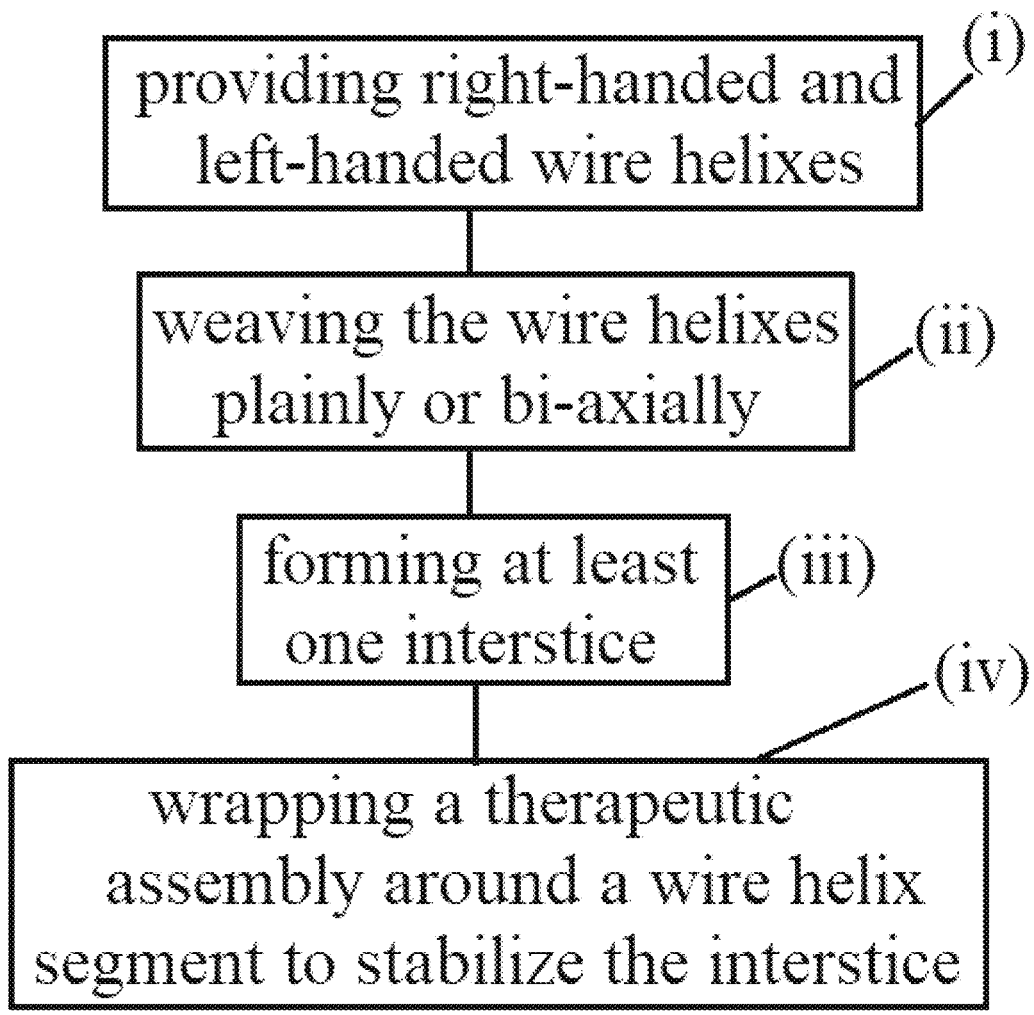
FIG. 11 is a flow chart of a general method of manufacturing a catheter apparatus used in an exemplary embodiment.

The present invention further provides a method of manufacturing the catheter apparatus as described above. As shown in FIG. 11, the method may include: (i) providing m right-handed wire helixes and n left-handed wire helixes, m≥2, and n≥2; (ii) weaving the wire helixes plainly or bi-axially into a tubular structure as the carrier; (iii) forming at least one interstice that is defined by four wire helix segments from two immediately adjacent right-handed wire helixes and two immediately adjacent left-handed wire helixes that are plainly or bi-axially woven into each other; and (iv) wrapping at least one therapeutic assembly around at least one of said four wire helix segments to stabilize the interstice.

Figure 12:
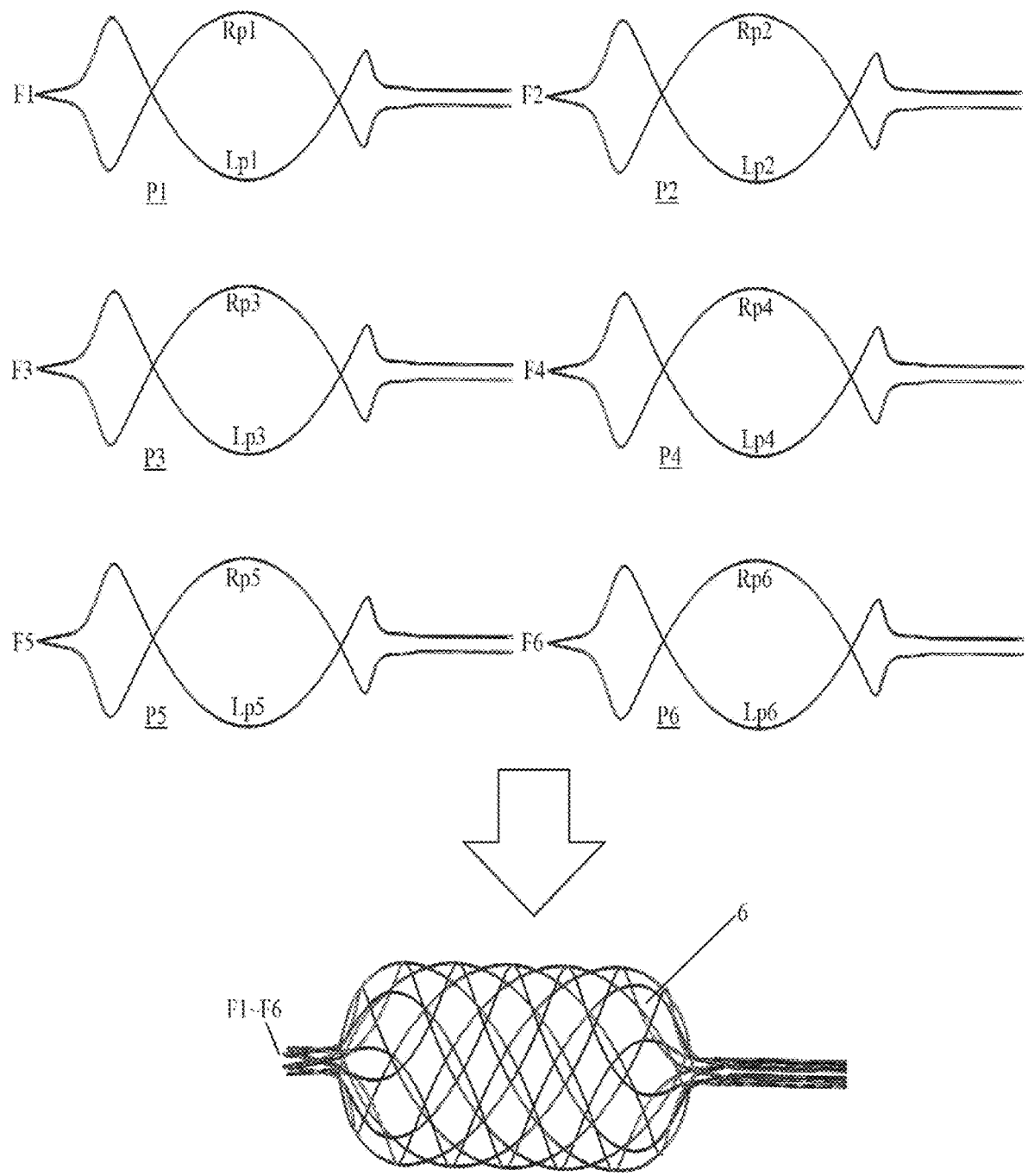
FIG. 12 demonstrates a method of manufacturing a catheter apparatus used in an exemplary embodiment.

In particularly preferred embodiments as shown in FIG. 12, at least one of the m right-handed wire helixes (e.g. one of the 6 R-helixes. R1~R6, as shown in FIG. 6) and at least one of then left-handed wire helixes (e.g. one of the 6 L-helixes L1~L6, as shown in FIG. 6) are made from one single wire, e.g. one of RL-Paired wires P1~P6. The single wire (e.g. P1) includes a first portion of right-handed wire helix Rp, e.g. one of Rp1~Rp6 that are equivalent to R1~R6; and a second portion of left-handed wire helix Lp, e.g. one of Lp1~Lp6 that are equivalent to L1~L6, by folding or bending a point (F1~F6) of the single wire (P1~P6) between the first portion and the second portion with an angle of approximately 160~180 degree.

As such, step (i) may include the steps of (ia) providing one single wire having a first portion of right-handed wire helix and a second portion of left-handed wire helix; and (ib) folding or bending the single wire at a point between the first portion and the second portion to provide a right-handed wire helix and a left-handed wire helix.

Figure 13:
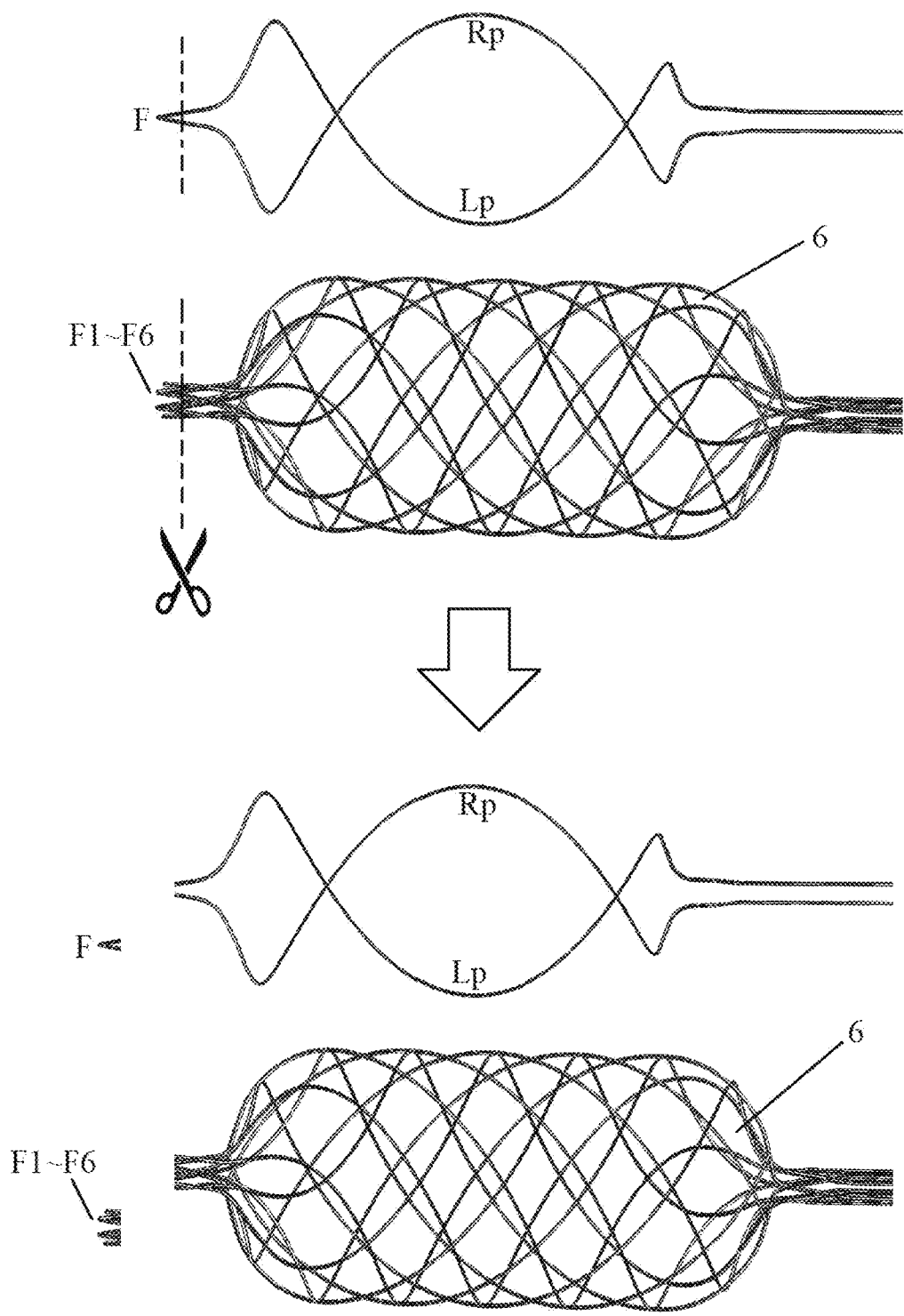
FIG. 13 demonstrates another method of manufacturing a catheter apparatus used in an exemplary embodiment.

In other particularly preferred embodiments as shown in FIG. 13, the method further includes a step of cutting the bent single wire at or near the bending point (F1~F6) to make a separate right-handed wire helix and a separate left-handed wire helix.

Figure 14:
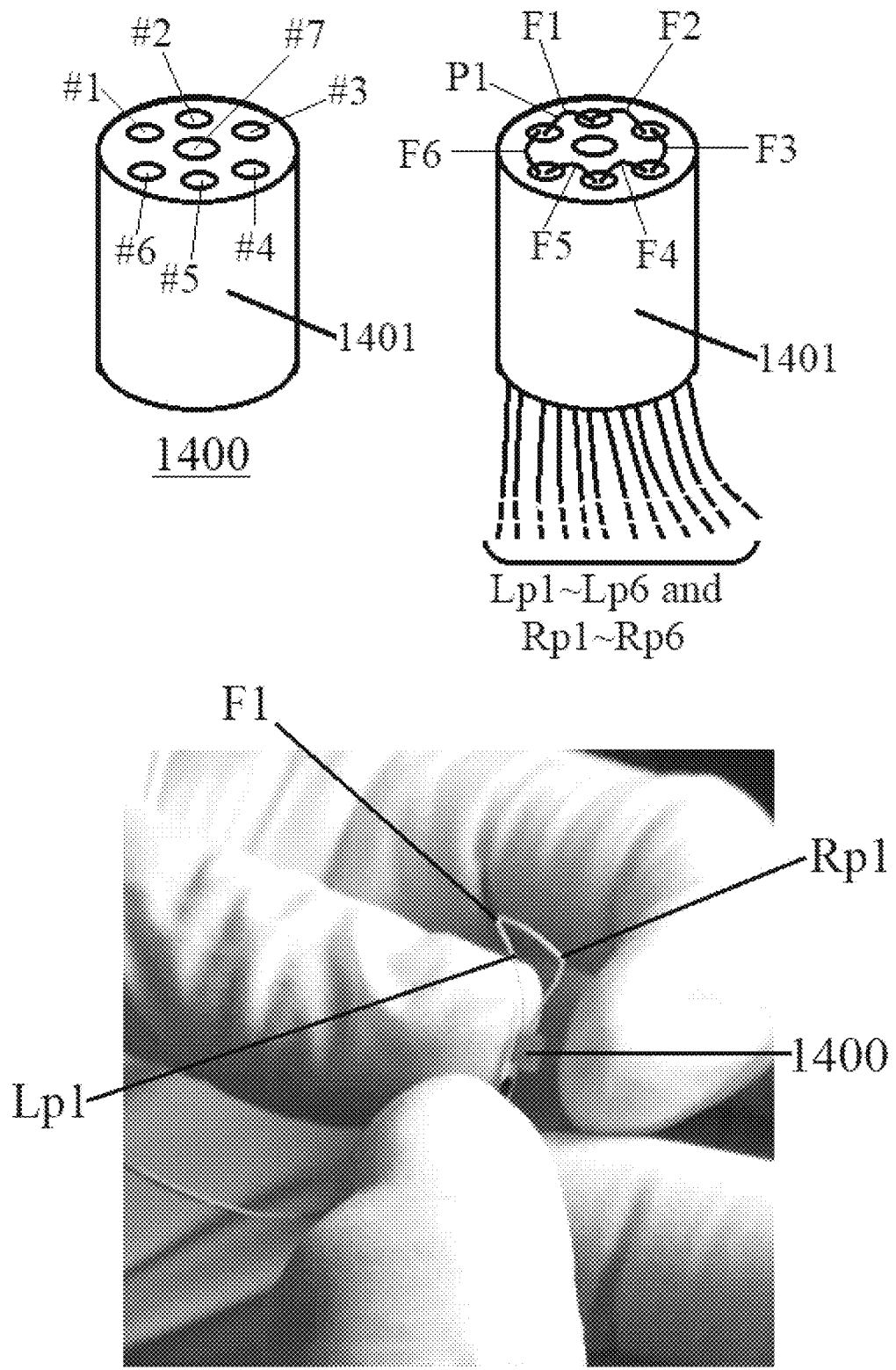
FIG. 14 illustrates the using of a multi-lumen bundler in organizing wires for weaving a carrier used in an exemplary embodiment.

In another embodiment, RL-Paired wires P1, P2, P3, P4, P5 and P6 are bundled together at their ends of the bending points using a multi-lumen bundler. Referring to FIG. 14, the multi-lumen bundler 1400 has a cylinder body 1401. A number of lumens #1~#6 pass axially through the cylinder body 1401 along the longitudinal axis of the cylinder body 1401, and may be arranged in a circular configuration. For a single RL-Paired wire, the first portion of right-handed wire helix Rp may be inserted into a lumen and pass through the lumen, and the second portion of left-handed wire helix. Lp may be inserted into another lumen and pass through the lumen. The first portion of right-handed wire helix and the second portion of left-handed wire helix from a same wire may be inserted into and pass through two different lumens. The folding point or bending point of the RL-Paired wire is placed between the two mouths of the two lumens. In exemplary embodiment as shown in FIG. 14, for a single RL-Paired wire P1, the first portion of right-handed wire helix Rp1 may be inserted into lumen #1 and may pass through the lumen #1, and the second portion of left-handed wire helix Lp1 may be inserted into lumen #2 and pass through the lumen #2. The folding point or bending point F1 of the RL-Paired wire P1 is placed between the two mouths of two lumens #1 and #2, preferably F1 is located at the middle point between the two mouths of the two lumens #1 and #2. For RL-Paired wire P2, the first portion of right-handed wire helix Rp2 may be inserted into lumen #2 and may pass through the lumen #2, and the second portion of left-handed wire helix Lp2 may be inserted into lumen #3 and pass through the lumen #3. The folding point or bending point F2 of the RL-Paired wire P2 is placed between the two mouths of two lumens #2 and #3, preferably F2 is located at the middle point between the two mouths of the two lumens #2 and #3. For P3, Rp3 may be inserted into and pass through lumen #3, and Lp3 may be inserted into and pass through lumen #3. Folding point F3 is placed between the two mouths of two lumens #3 and #4, preferably at the middle point there between. For P4, Rp4 and Lp4 may be inserted into and pass through lumens #4 and #5, respectively, and F4 is placed between the two mouths of two lumens #4 and #5, preferably at the middle point there between. In a similar fashion, Rp5 and Lp5 may be inserted into and pass through lumens #5 and #6, respectively, and F5 is placed between the two mouths of two lumens #5 and #6, preferably at the middle point there between. Rp6 and Lp6 may be inserted into and pass through lumens #6 and #1, respectively, and F6 is placed between the two mouths of two lumens #6 and #1, preferably at the middle point there between. The number of wire-accepting lumens may be no less than the number of wires. The number of wire-accepting lumens may be equal to the number of wires. For example, an optional central lumen #7 in parallel with lumens #1~#6 may be included in bundler 1400, not for accepting any RL-Paired wire, but for e.g. control wire or pull/push wire 19 to pass through, if needed. After RL-Paired wires P1~P6 are properly placed in lumens #1~#6 as described above, a liquid adhesive material may be filled into or dropped into lumens #1~#6. After the liquid adhesive material is solidified, RL-Paired wires P1~P6 will be permanently glued and fixed to multi-lumen bundler 1400.

Figure 15:
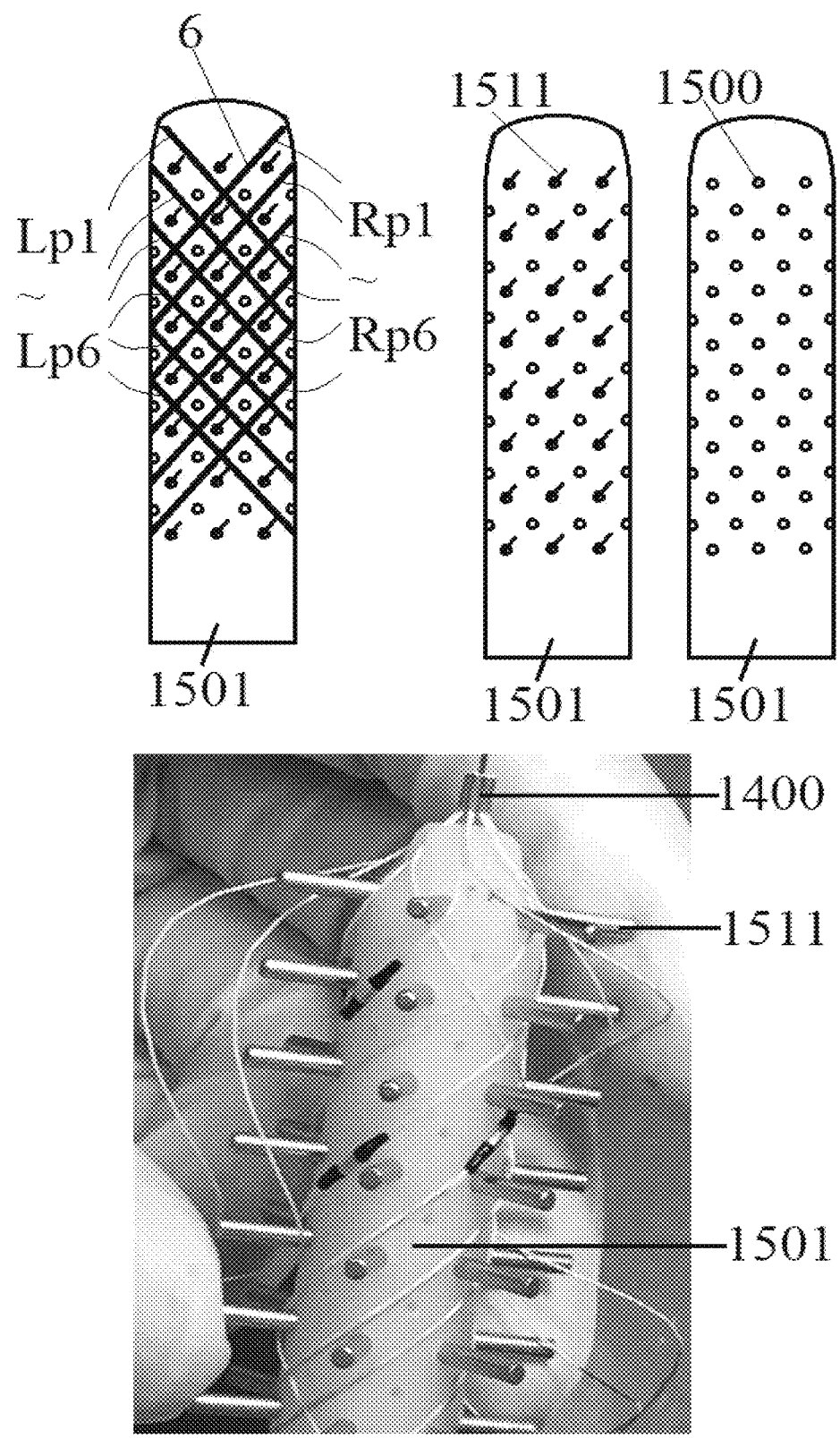
FIG. 15 illustrates the using of a bobbin and a multi-lumen bundler in weaving wire helixes plainly or bi-axially into a tubular structure in accordance with an exemplary embodiment.

When step (ii), i.e. weaving the wire helixes plainly or bi-axially into a tubular structure as the carrier, is implemented, a bobbin may be used as a scaffold. As shown in FIG. 15, a bobbin 1501 has an array of holes 1500 on it, for pins 1511 to insert in. Between any two pins 1500, or two rows of pins 1500, a wire such as one of P1~P6 may be wound. The pins 1500 may function as flanges for bobbin 1501. Multi-lumen bundler 1400 may optionally be used with bobbin 1501. When it is used, multi-lumen bundler 1400 with loose RL-Paired wires P1~P6 is placed on top tip of the bobbin 1501, and functions as the start point of the weaving process. After the weaving process is completed, pins 1511 are removed from bobbin 1501, leaving behind a tubular structure as the carrier of the invention.

EXAMPLES

The protocol in the following Examples was approved by an Ethics Committee/Institutional Review Board for Clinical Research. Patients meeting the following criteria were enrolled in the study: (i) patients suffering from pain caused by abdominal cancer; (ii) visual analog score (VAS) of the patients was >6; and (iii) patients had ages of 25-75 years and had ≥1 month of expected survival time. The exclusion criteria were as follows: (i) pregnant or intending to become pregnant within 1 year; (ii) postural hypotension; (iii) aortic pathologies such as aneurysm or dissection; (iv) type 1 diabetes mellitus; (v) acute or severe systemic infection; (vi) cerebral apoplexy or transient ischemic attack in the past 2 weeks; and (vii) acute coronary syndrome in the past 2 weeks. Every patient signed written informed consent for the procedures performed and for their inclusion in the study.

Abbreviations in the Examples include AE: adverse event; CPN: celiac plexus neurolysis; EDN: endovascular denervation; EUS-CPN: endoscopic ultrasound-guided celiac plexus neurolysis; QOL: quality of life; RDN: renal denervation; SMA: superior mesenteric artery; VAS: visual analog score; and WHO: World Health Organization.

Seven cancer patients (2 males and 5 females) were enrolled. The diagnoses of the patients included pancreatic cancer for 3 patients, cervical carcinoma for 2 patients, cholangiocarcinoma for 1 patient, and esophageal cancer with retroperitoneum lymph nodes invasion for 1 patient. Denervation was carried out at the abdominal aorta close to the origin of celiac artery and superior mesenteric artery as defined above with the use of a 6-electrode radiofrequency ablation catheter as described above with settings of time 60 or 120 seconds and temperature of 60° C. The effects of endovascular denervation (EDN) on abdominal cancer pain relief were evaluated. The primary end point was improvement in pain scores. The secondary end points include improvement of life quality, less intake of narcotics, and the safety of EDN.

As shown in the baseline characteristics of the patients as summarized in Table 1, all the patients were suffering from severe cancer pain as evidenced by the VAS scores of >7.

TABLE 1

Baseline Characteristics of the Patients

| Patient | Sex | Age | Basic Diagnosis | VAS Score | QOL Score |
|---|---|---|---|---|---|
| #1 | F | 30 | Cervical carcinoma | 8.5 | 228 |
| #2 | M | 49 | Pancreatic cancer | 8 | 210 |
| #3 | M | 53 | Pancreatic cancer | 7.5 | 245 |
| #4 | F | 74 | Pancreatic cancer | 8 | 230 |
| #5 | F | 49 | Cervical carcinoma | 7 | 230 |
| #6 | F | 65 | Cholangiocarcinoma | 8 | 230 |
| #7 | F | 75 | Esophageal cancer | 8 | 213 |

Every time, only one of 6 internal electrodes was activated. The 6 internal electrodes took turn to work. A thermal couple was placed inside each of the internal electrodes to measure the "electrode temperature". If the electrode temperature could not rise to the preset temperature anyway and the power reached the maximum level 9 W, a judgement was made that the electrode did not intimately contact the blood vessel internal wall. The procedure then started over, and the catheter was adjusted so that the electrode can contact intimately to the blood vessel internal wall. Sometimes, the position of the catheter was adjusted, and the ablation was repeated once more to guarantee a good therapeutic result. For example, in patient #7 as will be described, the ablation has been repeated for four times. In the first time and the second time, some internal electrodes did not intimately contact the blood vessel internal wall and, for other internal electrodes, the electrode temperature could not rise to the target temperature and the power reached the maximum level 9 W. Therefore, the catheter position was adjusted, and the basket supporting the internal electrodes (i.e. carrier 6) was expanded bigger.

Figure 16:
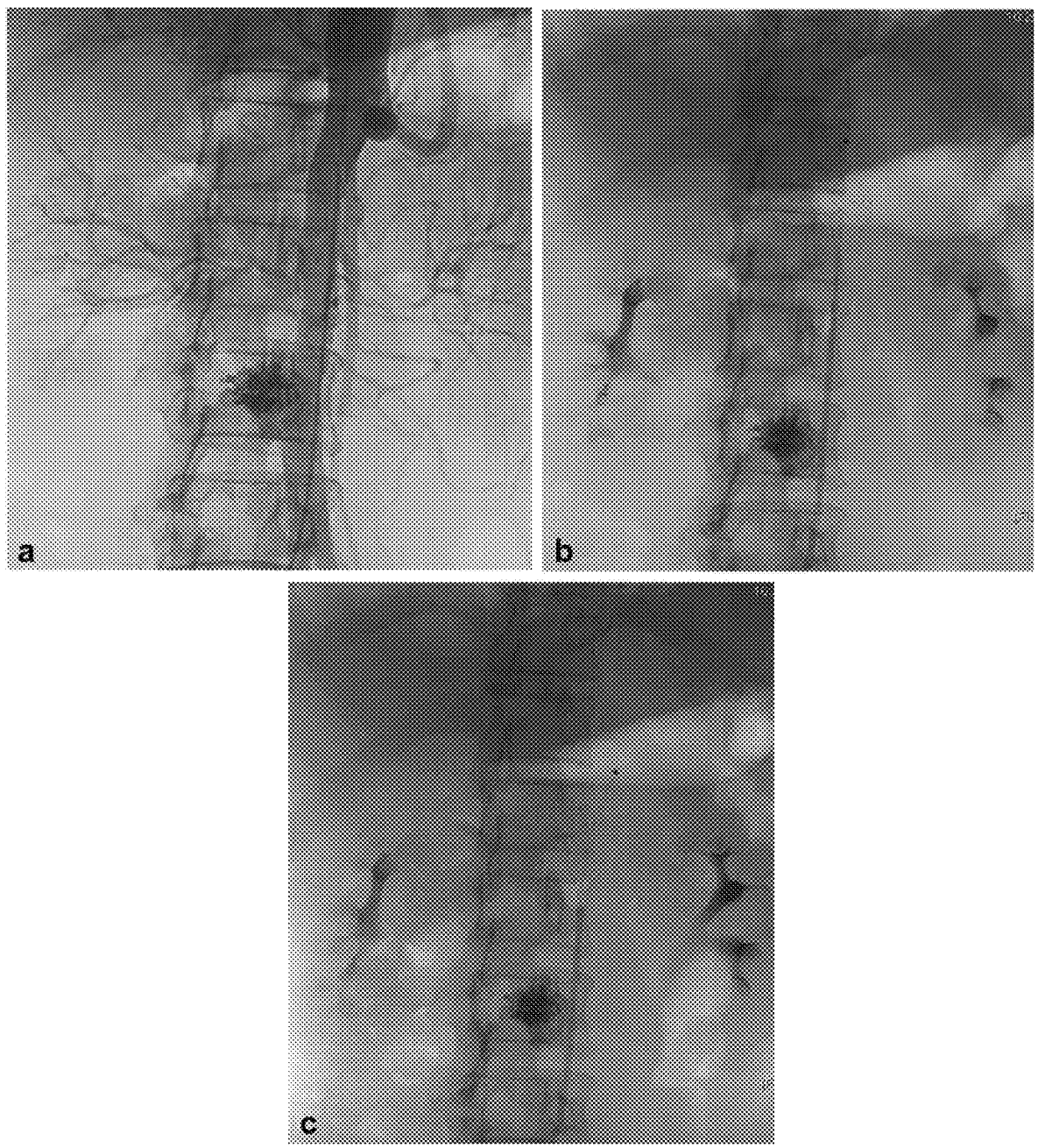
FIG. 16 shows representative digital subtraction angiography of the abdominal aorta in accordance with an exemplary embodiment of the present invention.

A surface electrode was placed on the back of the patient and connected to the denervation device. Abdominal aortography was performed to identify the level of celiac artery and superior mesenteric artery (SMA) by means of transfemoral access with the use of an 8-F sheath and 5-F pigtail catheter. Then the EDN 6-electrode catheter (Golden Leaf, Shanghai) was inserted to the proximal celiac artery and abdominal aorta close to the SMA through the sheath. Figure EE01 shows the multiple-electrode endovascular denervation (EDN) catheter. This multi-electrode EDN catheter has 6 electrodes helically on a net structure, and the ablation electrodes can expand according to celiac artery and superior mesenteric artery diameters and stick to the artery wall by drawing and rotating the catheter basket. The catheter was connected to the denervation device. The patients were under moderate sedation with combinations of intravenous midazolam and/or oxycodone when EDN started. Denervation was carried out with ablation parameters set at time 60 or 120 seconds and temperature 60° C. The celiac artery and the abdominal aorta close to the origin of the SMA were treated with 6 points of ablation, separately. After completion of the ablation, angiography of abdominal aorta was performed via the pigtail catheter. FIG. 16 shows representative digital subtraction angiography of the abdominal aorta, in which panel a shows the angiography before the endovascular denervation; panel b shows that the 6-electrode catheter was inserted to the origin of celiac artery in the abdominal aorta; and panel c shows that the 6-electrode catheter was inserted to the origin of superior mesenteric artery in the abdominal aorta. The puncture site was closed with the use of Proglide vascular closure devices (Abbott Vascular, Abbott Park, Ill.).

The primary end point was pain relief as measured by means of VAS. The secondary end points were quality of life (QOL) assessment, intake of narcotics, and the safety of EDN. Pain scores were assessed with the use of a standardized 11-point continuous VAS, with "0" equaling no pain, "5" moderate pain, and "10" the worst pain ever, on the day before EDN and 1, 2, 4, 8, and 12 weeks after the procedure. VAS score reduction by ≥3 points after the treatment was considered to be significant pain relief. To minimize subjective variations in the assessment of VAS scores, a same physician performed the scoring of all patients. The WHO QOL-100, containing 25 facets of QOL in 6 domains, is considered to be a reliable and valid measure in chronic pain management programs. In the study, QOL-100 assessments were completed before EDN and 2, 4, and 8 weeks after the procedure. The intake of narcotics also was recorded on the day before EDN and 1, 2, 4, 8, and 12 weeks after the operation. Narcotics use after the procedure was compared with before EDN. Adverse events (AEs) were graded according to the Common Terminology Criteria for Adverse Events (CTCAE v4.0) of the National Cancer Institute (Bethesda, Md.). If there were any abnormalities found after the operation, follow-up CT or CT angiography was performed.

Quantitative data were presented as mean±standard deviation. Differences in observational variables between the baseline and the set time point of 1, 2, 4, 8, and 12 weeks after the procedure were assessed by means of the paired t test. All statistical analyses were performed with the use of the SPSS statistics software (v18.0; IBM Corp, Somers, N.Y.). A level of $P \leq 0.05$ was defined as statistically significant.

Figure 17:
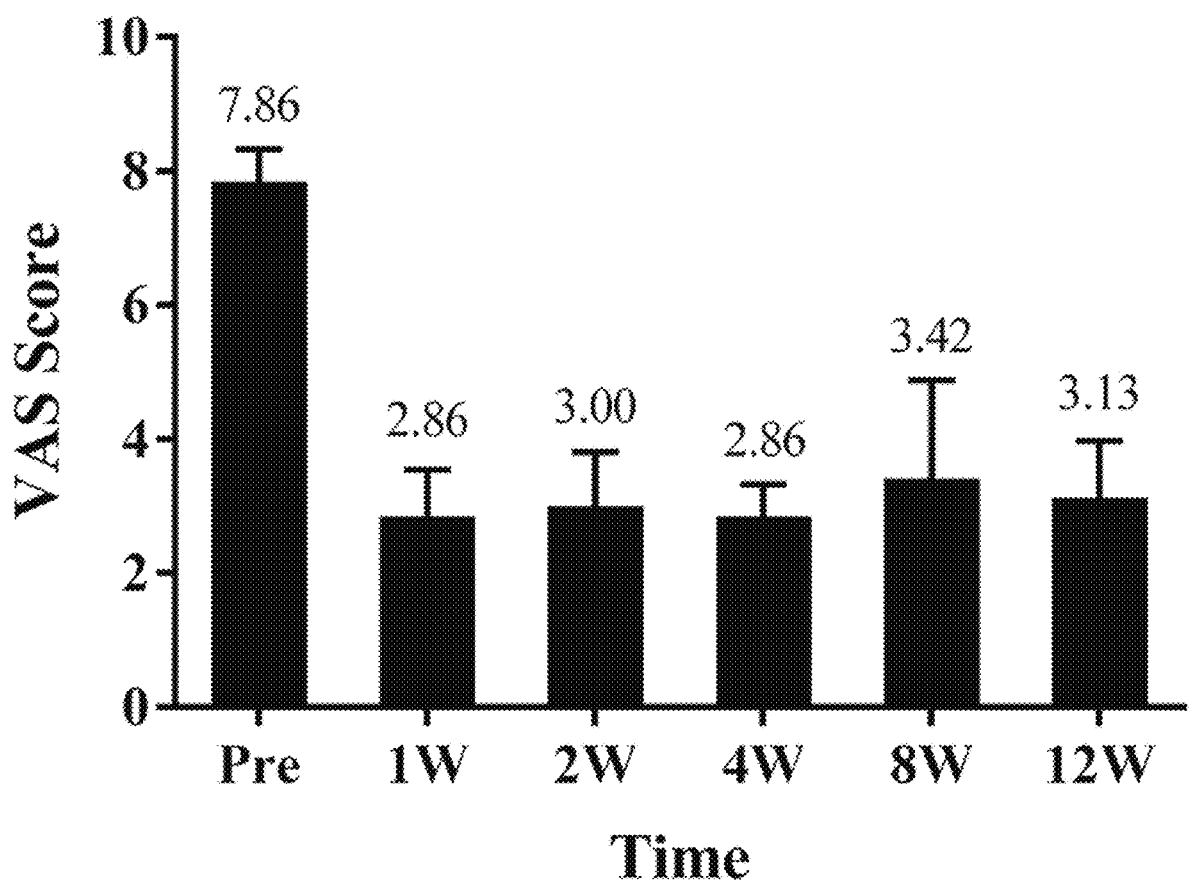
FIG. 17 shows that cancer pain VAS scores are decreased significantly after the procedure in accordance with an exemplary embodiment of the present invention.

Regarding pain palliation/relief response after EDN, all of the patients experienced pain relief after EDN. As shown in FIG. 17, pain scores decreased significantly at 1, 2, 4, 8, and 12 weeks after the procedure compared with baseline. Average VAS score reduced by ≥3 points in all 7 patients (100%), which were therefore considered to have had a significantly positive response, with great pain palliation ($P<0.001$).

Figure 18:
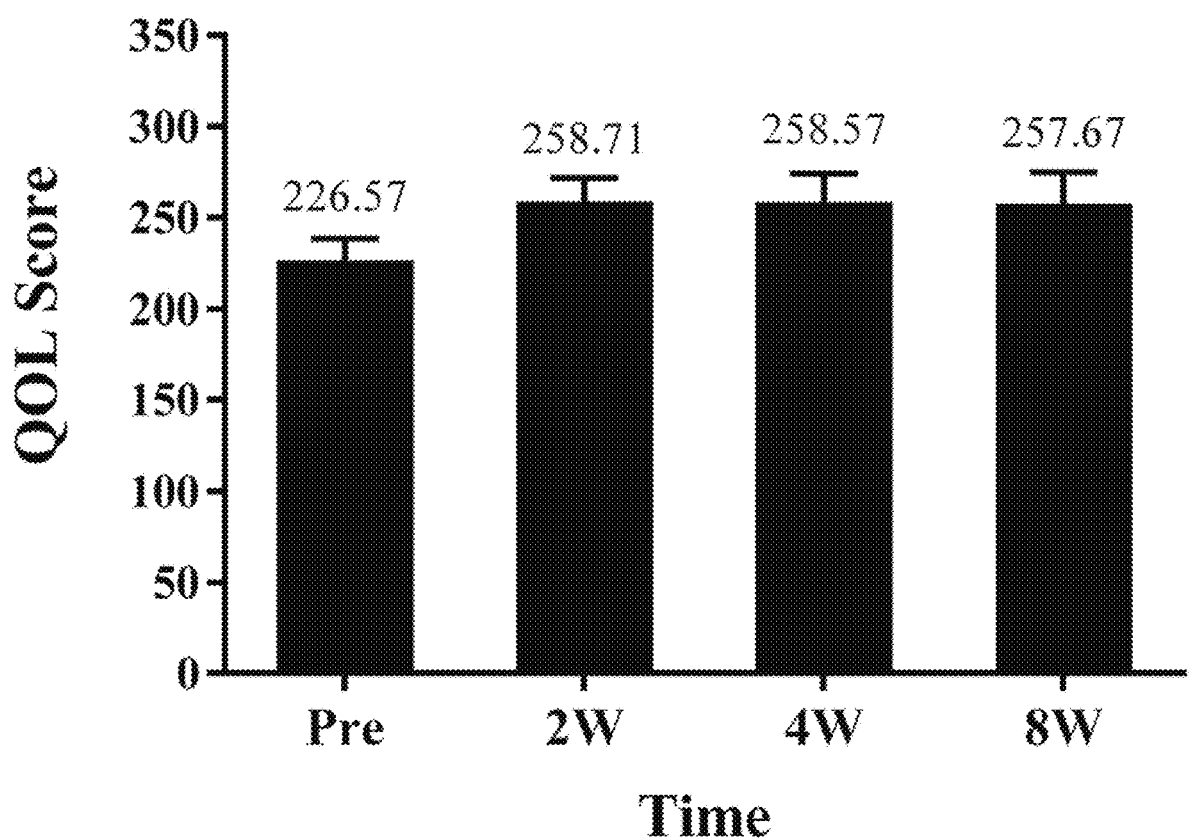
FIG. 18 illustrates the improvement of cancer patient's Quality of Life in accordance with an exemplary embodiment of the present invention.

FIG. 18 and FIG. 19 illustrate the improvement of Quality of Life. WHO QOL-100 scores assessed before the EDN and 2, 4, and 8 weeks after the procedure. Physical, psychologic, and level of independence scores were significantly improved after the procedure. Social relationships, environment, and spirituality did not change after EDN. The average QOL-100 scores increased >25 points compared with before the operation ($P<0.005$). Most patients reported better and longer sleep and much more enjoyment of leisure activities.

Regarding decrease in intake of narcotics, a significant reduction in narcotic use occurred in all patients after the procedure. The patients experienced significantly less pain and their analgesic consumption was reduced. Two of the 7 cases, who had taken dezocine muscle injection at 10 mg and 5 mg daily before the EDN treatment, stopped using any narcotics within 12 weeks after. One patient, who had taken 30 mg morphine and 10 mg acetaminophen daily to control pain before EDN, decreased to 10 mg acetaminophen within 4 weeks, and adjusted to 20 mg morphine at 8 weeks after EDN.

With respect to safety of EDN, the technical success of this study was 100%. No severe treatment-related AEs or major complications, such as aneurysm or dissection (grade III or above according to CTCAE v4.0) were observed. Two patients had minor abdominal distension and constipation after EDN, which resolved within 3 days.

Renal denervation (RDN) causes substantial and sustained blood-pressure reduction, which could result from both ablation of renal sympathetic nerves passing to the kidney and destruction of afferent renal nerves. The lesion depth was 6.4 mm in the treated renal arteries after the procedure of radiofrequency-delivering RDN, which suggested that most of the renal sympathetic nerves could be ablated by radiofrequency-RDN. A neuroleptic or analgesic agent injected into the celiac plexus disrupts the transmission of pain signals from afferent nerves to the spinal cord. Therefore, it is believed, without being bound by any particular theory, that a multiple-electrode catheter placed in the abdominal aorta around the origin of celiac artery and the SMA, may cause celiac plexus block to some degree and control pain of abdominal cancer. As radiofrequency ablation RDN can generate structure changes in neural fibers, it is believed, without being bound by any particular theory, that radiofrequency ablation may affect the celiac plexus both anatomically and functionally.

In the present study, 7 patients received EDN treatment with the use of a radiofrequency denervation system with a novel multi-electrode mesh catheter, as described above. All of the patients experienced pain relief after EDN. Pain scores decreased significantly at 1, 2, 4, 8, and 12 weeks after the procedure as compared to the baseline. The results were similar to CPN guided by CT or percutaneous EUS guided by CT using either a bilateral posterior or an anterior approach, with the efficacy of pain relief in 10%-24% when used alone and in 80%-90% combined with other treatment options.

In summary, all of the patients experienced pain relief. The pain scores as measured by means of visual analog scores at 1, 2, 4, 8, and 12 weeks after the procedure were significantly lower than before the operation (P<0.001). A >4 score reduction was observed in all patients. A significant reduction in narcotics use within 3 months after the operation was also observed. The quality of life scores of the patients have been improved significantly (P<0.005) with better sleep. No severe treatment-related adverse events or major complications were observed. Therefore, EDN is a safe and effective means to alleviate pain caused by cancer and may serve as a solution for cancer pain relief and palliative care. EDN is a promising and safe method for the palliation of pain caused by abdominal cancers.

In the following, representative examples will be employed to illustrate the method of the present invention.

Figure 20:
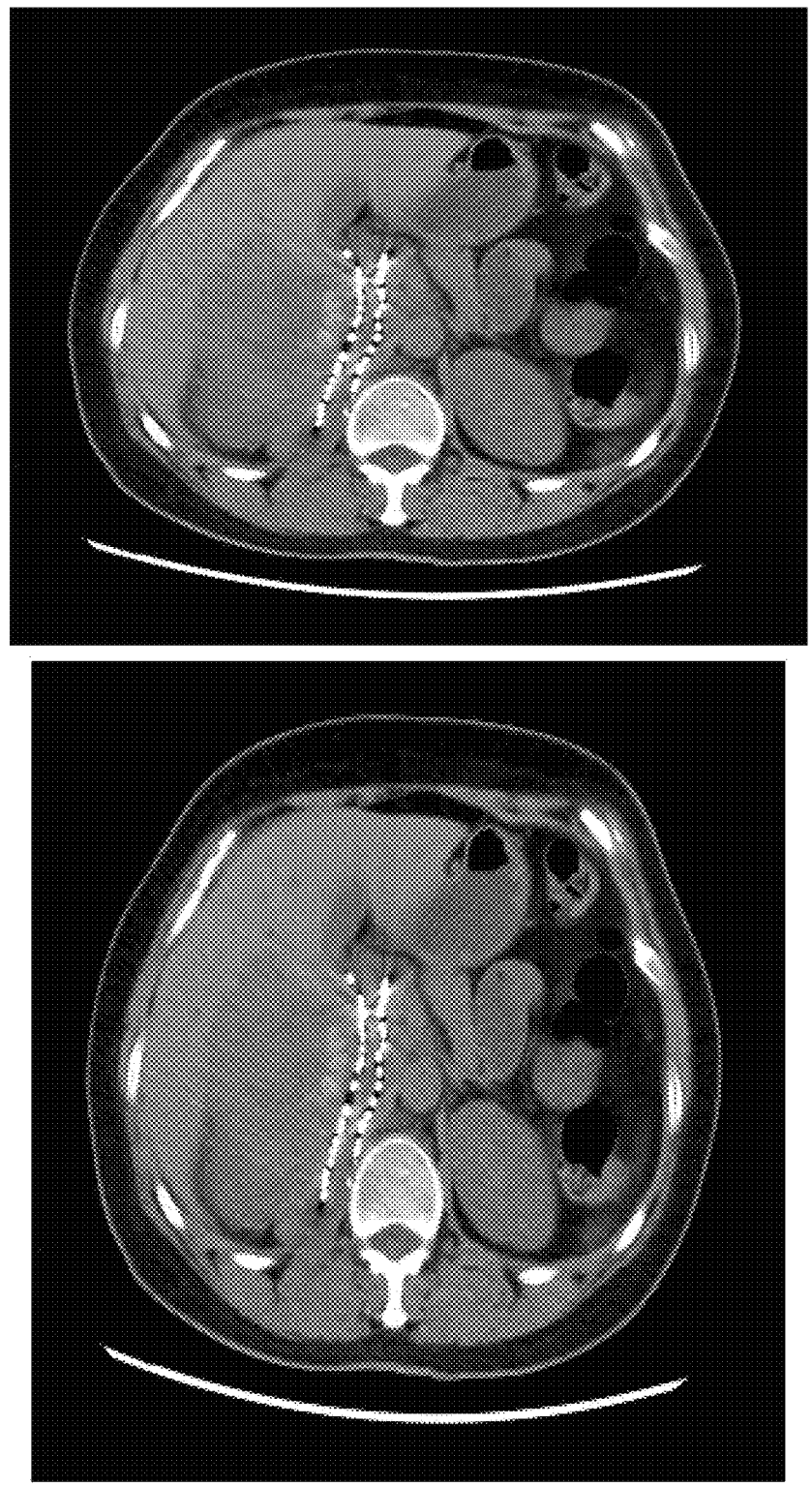
FIG. 20 shows CT images of a patient of cervical carcinoma before the procedure in accordance with an exemplary embodiment of the present invention.
Figure 21:
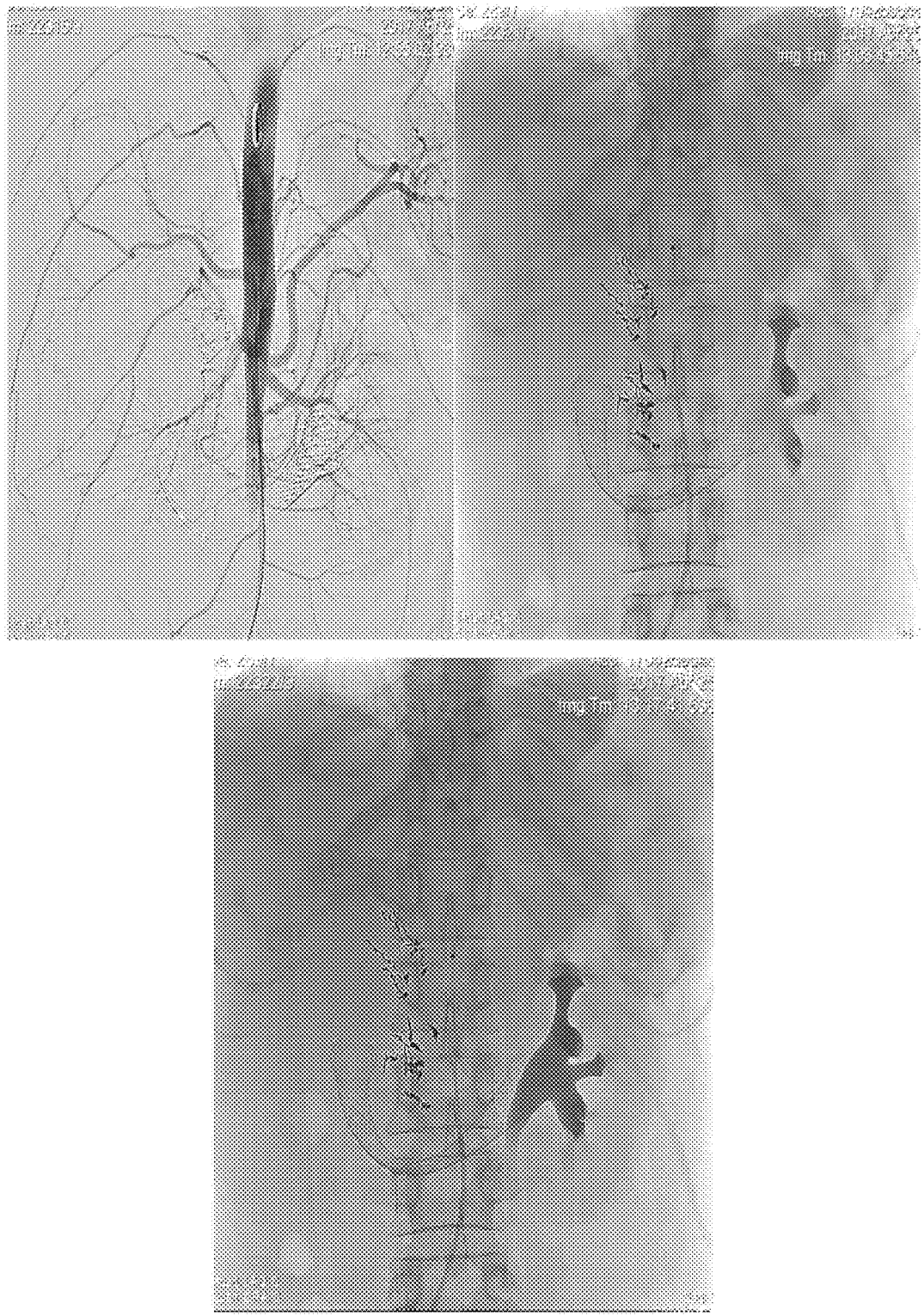
FIG. 21 shows CT images of a patient of cervical carcinoma during the procedure in accordance with an exemplary embodiment of the present invention.
Figure 22:
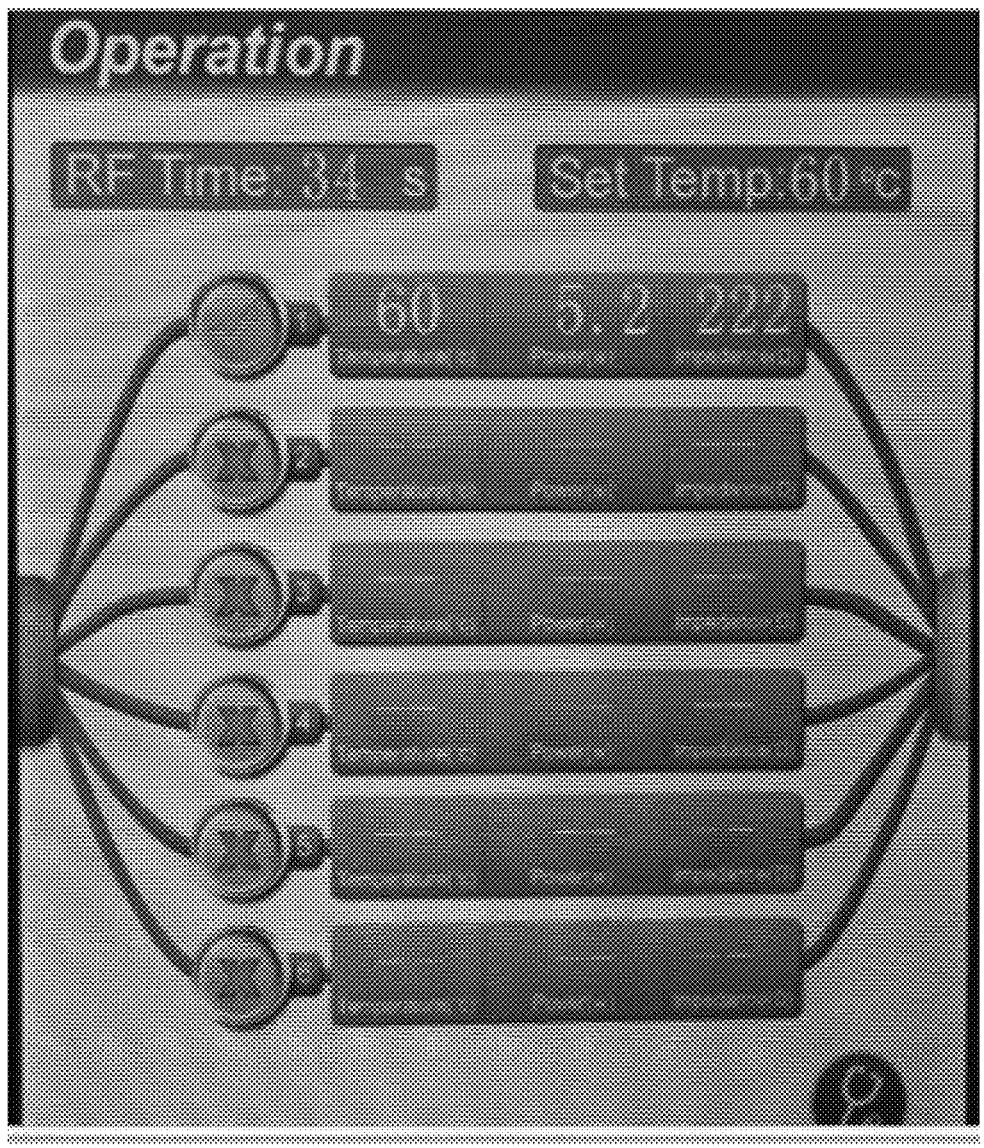
FIG. 22 displays the controlling of parameters of a procedure in accordance with an exemplary embodiment of the present invention.
Figure 23:
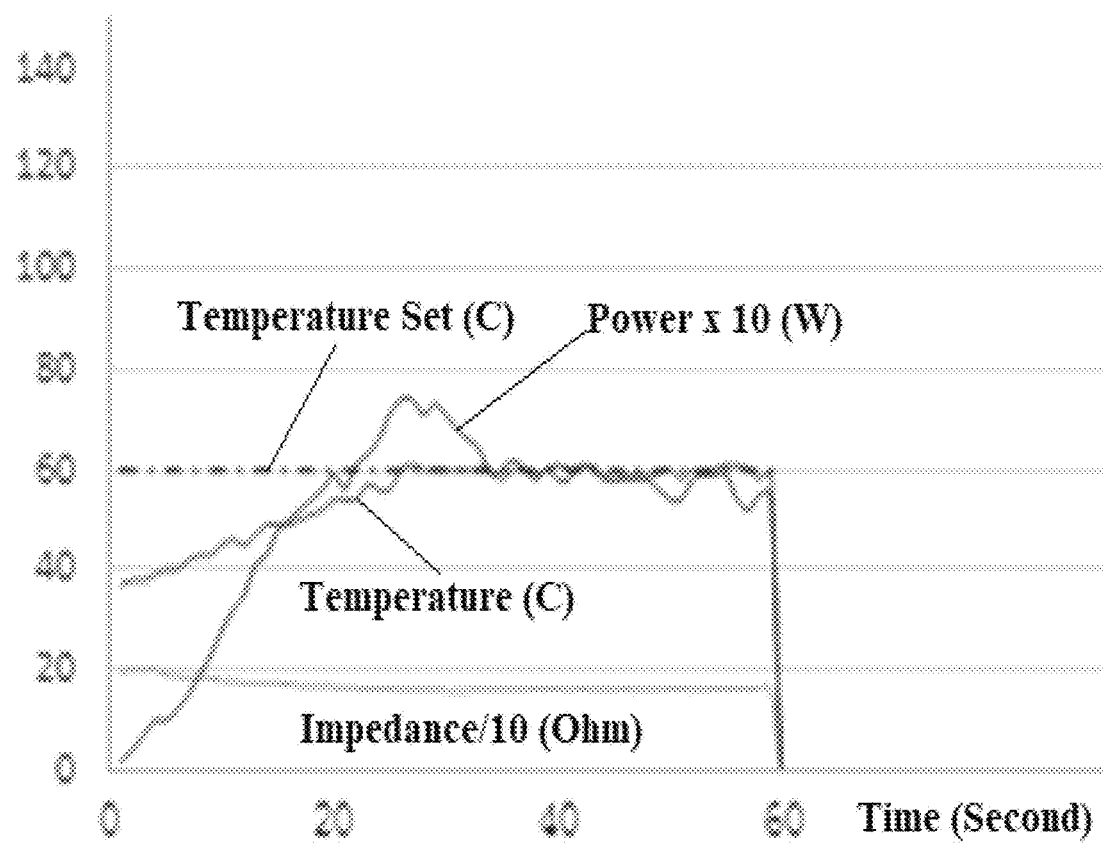
FIG. 23 is a plot showing a representative protocol of a procedure including power, temperature, and impedance as a function of time in accordance with an exemplary embodiment of the present invention.

Patient #1 (female, age 30, cervical carcinoma): FIG. 20 shows CT images of the patient before the procedure, and FIG. 21 shows CT images of the patient during the procedure. After 6 ablation electrodes #1~#6 (from top to down) were placed within the target segment of the abdominal aorta of the patient and against blood vessel wall of the abdominal aorta and a surface electrode was adhered on the skin of the patient's back, the procedure was initiated. For each of the electrodes #1~#6, the ablation target temperature was set as 60° C., the ablation period was set as 60 seconds, the ablation power was adjusted (increased as needed, or decreased if too high) during the ablation period with a ceiling of 9 W, the ablation frequency was set as 465 KHz. The impedance between the surface electrode and electrodes #1~#6 varied from electrode to electrode and from one real time to another real time, but typically within the range of 170-230 Ohms. As shown in FIG. 22, electrode #1 was turned on and electrodes #2-6 were turned off, with a set of parameters (temperature 60° C., RF period 60 seconds). At a given real-time time such as when RF time was 34 seconds (t=34 seconds), the real-time impedance between the surface electrode and electrode #1 was 222 Ohms, the real-time temperature was 60° C. (as desired), and the real-time power was 5.2 W (as desired, because it was below ceiling of 9 W). As shown in FIG. 23, the power with electrode #1 has been increased from 0 at t=0 to 7.7 W at t=28 sec, and the temperature has been increased from body temperature (BT) 37 C at t=0 to 60 C at t=28 sec. The power has been decreased from 7.7 W at t=28 sec down to 5.2 W at t=60 sec, and the temperature has been maintained around 60 C from t=28 sec to 60 sec. The impedance between the surface electrode and electrode #1 has been decreased from 200 Ohms at t=0 to 160 Ohms at t=60 sec. Such a protocol will be simply described as: Power increases from 0 to 7.7 W (t=0-28) and decreases from 7.7 W to 5.2 W (t=28-60); Temperature increases from BT to 60 C (t=0-28) and stays 60 C for 32 seconds (t=28-60); and Impedance decreases from 200 to 160 Ohms (t=0-60). Other treatment protocols will be described in a similar fashion.

For patient #1, the entire treatment protocol includes two sessions, as summarized in Table 2. Patient #5 (female, 49, cervical carcinoma) can be treated with similar protocol. The time period for non-ablative thermal alteration (<45° C.) is defined as Tna, the time period for ablative thermal alteration (≥4.5° C.) is defined as Ta, and the ratio between the two is defined as Rna/a.

TABLE 2

Treatment Protocol for Cervical Carcinoma

| Session | Electrode | Protocol |
|---|---|---|
| First Session | #1 | Rna/a = 10:50 (seconds): Power increases from 0 to 7.7 W (t = 0-28) and decreases from 7.7 W to 5.2 W (t = 28-60); Temperature increases from BT to 60 C. (t = 0-28) and stays 60 C. for 32 seconds (t = 28-60); Impedance decreases from 200 to 160 Ohms (t = 0-60). |
| | #2 | Rna/a = 8:52 (seconds): Power increases from 0 to 4.2 W (t = 0-33) and stays at 4.2 W (t = 33-60); Temperature increases from BT to 60 C. (t = 0-33) and stays 60 C. for 27 seconds (t = 33-60); Impedance decreases from 200 to 160 Ohms (t = 0-60). |
| | #3 | Rna/a = 5:55 (seconds): Power increases from 0 to 2.8 W (t = 0-18) and stays at 2.8 W (t = 18-60); Temperature increases from BT to 60 C. (t = 0-18) and stays 60 C. for 42 seconds (t = 18-60); Impedance decreases from 200 to 180 Ohms (t = 0-60). |
| | #4 | Rna/a = 5:55 (seconds): Power increases from 0 to 4.1 W (t = 0-25) and decreases from 4.1 W to 3.7 W (t = 25-60); Temperature increases from BT to 60 C. (t = 0-25) and stays 60 C. for 32 seconds (t = 25-60); Impedance decreases from 200 to 180 Ohms (t = 0-60). |

TABLE 2-continued

Treatment Protocol for Cervical Carcinoma

| Session | Electrode | Protocol |
| --- | --- | --- |
| | #5 | Rna/a = 12:48 (seconds): Power increases from 0 to 9 W (t = 0-30) and stays at 9 W (t = 30-60); Temperature increases from BT to 58 C. (t = 0-30) and stays 58 C. for 30 seconds (t = 30-60); Impedance decreases from 200 to 190 Ohms (t = 0-60). |
| | #6 | Rna/a = 17:43 (seconds): Power increases from 0 to 8.7 W (t = 0-30) and stays at 8.7 W (t = 30-60); Temperature increases from BT to 50 C. (t = 0-30) and stays 50 C. for 30 seconds (t = 30-60); Impedance decreases from 190 to 185 Ohms (t = 0-60). |
| Second Session | #1 | Rna/a = 5:55 (seconds): Power increases from 0 to 2.9 W (t = 0-18) and stays at 2.9 W (t = 18-60); Temperature increases from BT to 60 C. (t = 0-18) and stays 60 C. for 42 seconds (t = 18-60); Impedance decreases from 200 to 180 Ohms (t = 0-60). |
| | #2 | Rna/a = 12:108 (seconds): Power increases from 0 to 9 W (t = 0-30) and decreases from 9 W to 5 W (t = 30-120); Temperature increases from BT to 60 C. (t = 0-63) and stays 60 C. for 57 seconds (t = 63-120); Impedance decreases from 200 to 190 Ohms (t = 0-40), increases from 190 to 200 Ohms (t = 40-65), and maintains at 200 Ohms (t = 65-120). |
| | #3 | Rna/a = 20:45 (seconds): Power increases from 0 to 9 W (t = 0-20) and stays at 9 W (t = 20-65); Temperature increases from BT to 54 C. (t = 0-20) and stays 54 C. for 45 seconds (t = 20-65); Impedance decreases from 200 to 190 Ohms (t = 0-65). |
| | #4 | Rna/a = 7:113 (seconds): Power increases from 0 to 4 W (t = 0-20) and stays at 4 W (t = 20-120); Temperature increases from BT to 60 C. (t = 0-20) and stays 60 C. for 100 seconds (t = 20-120); Impedance decreases from 200 to 180 Ohms (t = 0-120). |
| | #5 | Rna/a = 5:115 (seconds): Power increases from 0 to 2.4 W (t = 0-20) and stays at 2.4 W (t = 20-120); Temperature increases from BT to 60 C. (t = 0-20) and stays 60 C. for 100 seconds (t = 20-120); Impedance decreases from 200 to 170 Ohms (t = 0-120). |
| | #6 | Rna/a = 6:114 (seconds): Power increases from 0 to 3 W (t = 0-20) and stays at 3 W (t = 20-120); Temperature increases from BT to 60 C. (t = 0-20) and stays 60 C. for 100 seconds (t = 20-120); Impedance decreases from 170 to 140 Ohms. (t = 0-120). |

Figure 24:
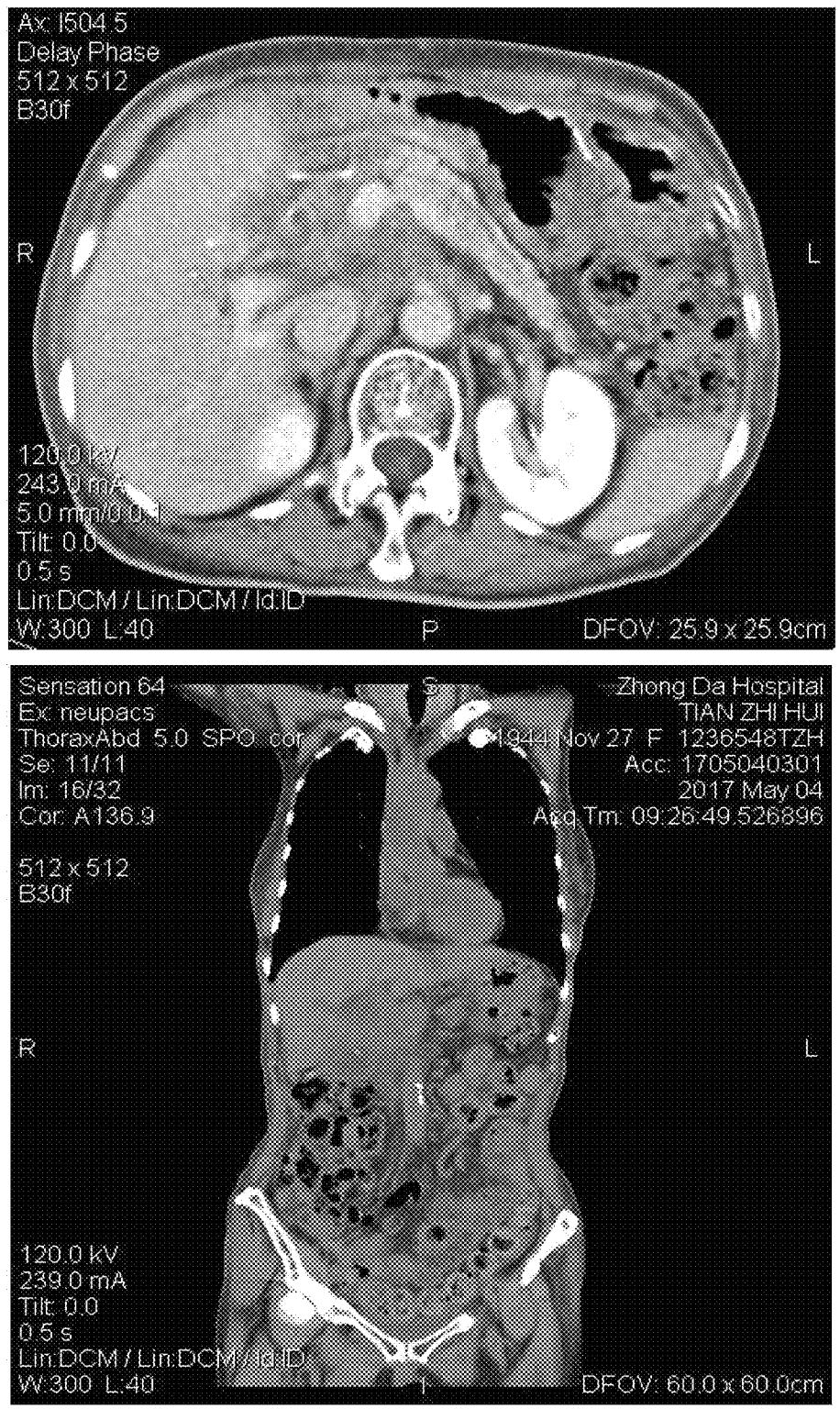
FIG. 24 shows CT images of a patient of esophageal cancer before the procedure in accordance with an exemplary embodiment of the present invention.
Figure 25:
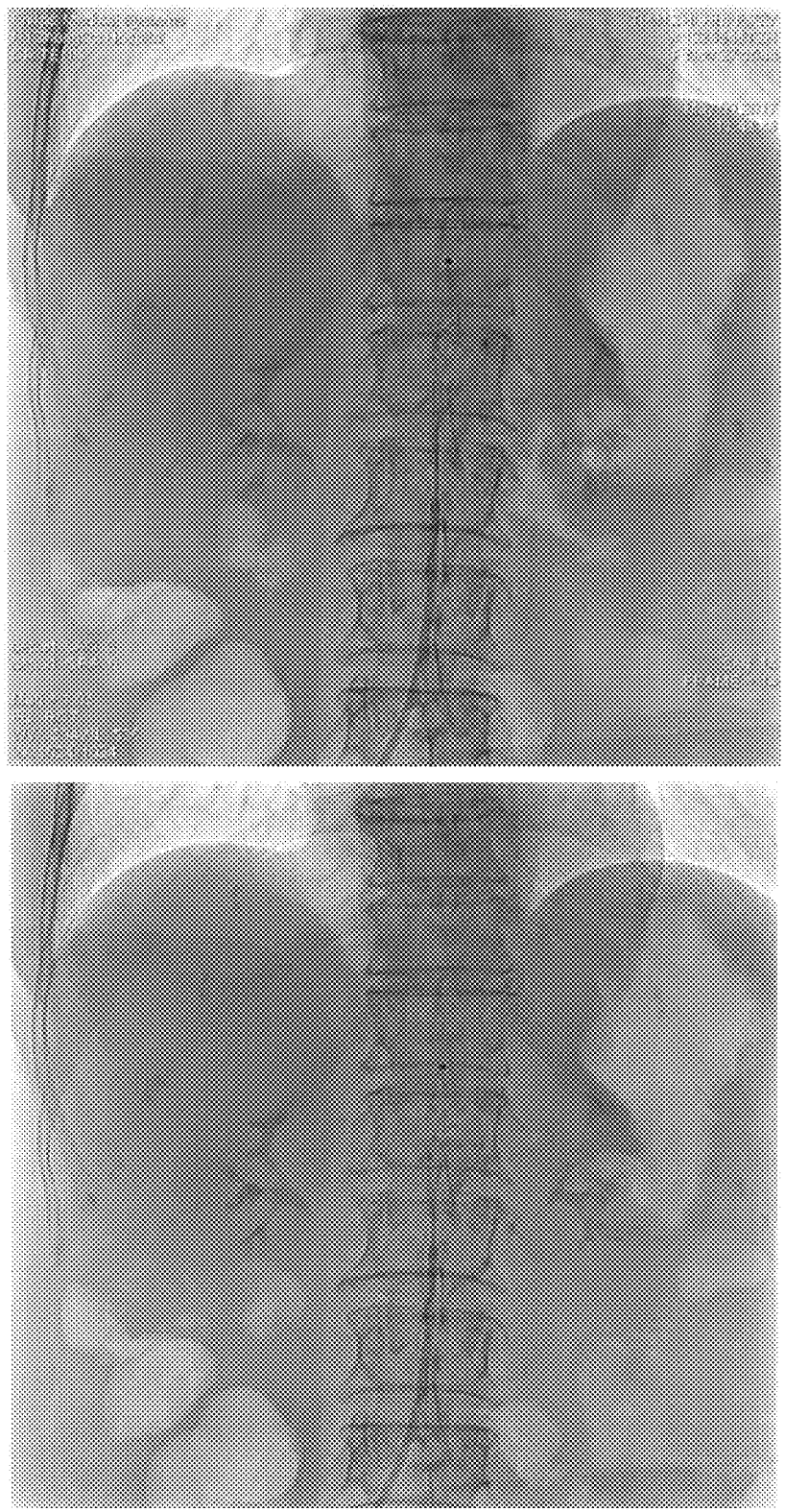
FIG. 25 shows CT images of a patient of esophageal cancer during the procedure in accordance with an exemplary embodiment of the present invention.

Patient #7 (female, 75, esophageal cancer): FIG. 24 shows CT images of the patient before the procedure, and FIG. 25 shows CT images of the patient during the procedure. Similar to patient #1, the entire treatment protocol for patient #7 includes four sessions, as summarized in Table 3.

TABLE 3

Treatment Protocol for Esophageal Cancer

| Session | Electrode | Protocol |
| --- | --- | --- |
| First Session | #2 | Rna/a = 10:50 (seconds): Power increases from 0 to 9 W (t = 0-33) and stays at 9 W (t = 33-60); Temperature increases from BT to 60 C. (t = 0-60) and stays 60 C. for 1 second (t = 60); Impedance decreases from 205 to 180 Ohms (t = 0-60). |
| | #3 | Rna/a = 20:0 (seconds): Power increases from 0 to 8.2 W (t = 0-20) and turned off; Temperature increases from BT to 42 C. (t = 0-20); Impedance decreases from 200 to 190 Ohms (t = 0-20). Off test |
| | #5 | Rna/a = 5:55 (seconds): Power increases from 0 to 3.8 W (t = 0-60); Temperature increases from BT to 59 C. (t = 0-60); Impedance decreases from 200 to 170 Ohms (t = 0-60). |
| | #6 | Rna/a = 8:52 (seconds): Power increases from 0 to 6.6 W (t = 0-39) and stays at 6.6 W (t = 39-60); Temperature increases from BT to 60 C. (t = 0-60) and stays 60 C. for 1 second (t = 60); Impedance decreases from 205 to 198 Ohms (t = 0-60). |
| | #1 & #4 | Off test |
| Second Session | #2 | Rna/a = 9:51 (seconds): Power increases from 0 to 8.2 W (t = 0-49) and stays at 8.2 W (t = 49-60); Temperature increases from BT to 45 C. (t = 0-60); Impedance decreases from 200 to 185 Ohms (t = 0-60). |
| | #3 | Rna/a = 9:51 (seconds): Power increases from 0 to 8 W (t = 0-60); Temperature increases from BT to 52 C. (t = 0-60); Impedance decreases from 200 to 185 Ohms (t = 0-60). |
| | #4 | Rna/a = 8:52 (seconds): Power increases from 0 to 8 W (t = 0-60); Temperature increases from BT to 60 C. (t = 0-60); Impedance decreases from 200 to 180 Ohms (t = 0-60). |
| | #5 | Rna/a = 7:53 (seconds): Power increases from 0 to 5.3 W (t = 0-60); Temperature increases from BT to 53 C. (t = 0-60); Impedance decreases from 200 to 180 Ohms (t = 0-60). |

TABLE 3-continued

Treatment Protocol for Esophageal Cancer

| Session | Electrode | Protocol |
|---|---|---|
| | #6 | Rna/a = 4:56 (seconds): Power increases from 0 to 3.1 W (t = 0-30) and stays at 3.1 W (t = 30-60); Temperature increases from BT to 60 C. (t = 0-30) and stays 60 C. for 30 seconds (t = 30-60); Impedance decreases from 208 to 190 Ohms (t = 0-60). |
| | #1 | Off test |
| Third Session | #1 | Rna/a = 3:57 (seconds): Power increases from 0 to 2.9 W (t = 0-20) and stays at 2.9 W (t = 20-60); Temperature increases from BT to 60 C. (t = 0-20) and stays 60 C. for 40 seconds (t = 20-60); Impedance decreases from 200 to 180 Ohms (t = 0-60). |
| | #2 | Rna/a = 5:55 (seconds): Power increases from 0 to 5 W (t = 0-45) and drops to 4 W (t = 45-60); Temperature increases from BT to 60 C. (t = 0-45) and stays 60 C. for 15 seconds (t = 45-60); Impedance decreases from 200 to 180 Ohms (t = 0-60). |
| | #3 | Rna/a = 3:57 (seconds): Power increases from 0 to 2.5 W (t = 0-15) and stays at 2.5 W (t = 15-60); Temperature increases from BT to 60 C. (t = 0-15) and stays 60 C. for 45 seconds (t = 15-60); Impedance decreases from 200 to 175 Ohms (t = 0-60). |
| | #4 | Rna/a = 3:57 (seconds): Power increases from 0 to 2.4 W (t = 0-18) and stays at 2.4 W (t = 18-60); Temperature increases from BT to 60 C. (t = 0-18) and stays 60 C. for 42 seconds (t = 18-60); Impedance decreases from 200 to 180 Ohms (t = 0-60). |
| | #5 | Rna/a = 4:56 (seconds): Power increases from 0 to 3 W (t = 0-25) and stays at 3 W (t = 25-60); Temperature increases from BT to 60 C. (t = 0-25) and stays 60 C. for 35 seconds (t = 25-60); Impedance decreases from 200 to 170 Ohms (t = 0-60). |
| | #6 | Rna/a = 3:57 (seconds): Power increases from 0 to 2.4 W (t = 0-18) and stays at 2.4 W (t = 18-60); Temperature increases from BT to 60 C. (t = 0-18) and stays 60 C. for 42 seconds (t = 18-60); Impedance decreases from 200 to 190 Ohms (t = 0-60). |
| Fourth Session | #1 | Rna/a = 7:53 (seconds): Power increases from 0 to 4 W (t = 0-60); Temperature increases from BT to 50 C. (t = 0-60); Impedance decreases from 200 to 180 Ohms (t = 0-60). |
| | #2 | Rna/a = 5:55 (seconds): Power increases from 0 to 6 W (t = 0-60); Temperature increases from BT to 60 C. (t = 0-60); Impedance decreases from 200 to 180 Ohms (t = 0-60). |
| | #3 | Rna/a = 3:57 (seconds): Power increases from 0 to 2.1 W (t = 0-19) and stays at 2.1 W (t = 19-60); Temperature increases from BT to 60 C. (t = 0-19) and stays 60 C. for 31 seconds (t = 19-60); Impedance decreases from 200 to 185 Ohms (t = 0-60). |
| | #4 | Rna/a = 3:57 (seconds): Power increases from 0 to 2 W (t = 0-18) and stays at 2 W (t = 18-60); Temperature increases from BT to 60 C. (t = 0-18) and stays 60 C. for 42 seconds (t = 18-60); Impedance decreases from 200 to 183 Ohms (t = 0-60). |
| | #5 | Rna/a = 9:51 (seconds): Power increases from 0 to 7.8 W (t = 0-60); Temperature increases from BT to 55 C. (t = 0-60); Impedance decreases from 200 to 185 Ohms (t = 0-60). |
| | #6 | Rna/a = 3:57 (seconds): Power increases from 0 to 2.3 W (t = 0-22) and stays at 2.3 W (t = 22-60); Temperature increases from BT to 60 C. (t = 0-22) and stays 60 C. for 38 seconds (t = 22-60); Impedance decreases from 200 to 190 Ohms (t = 0-60). |

Figure 26:
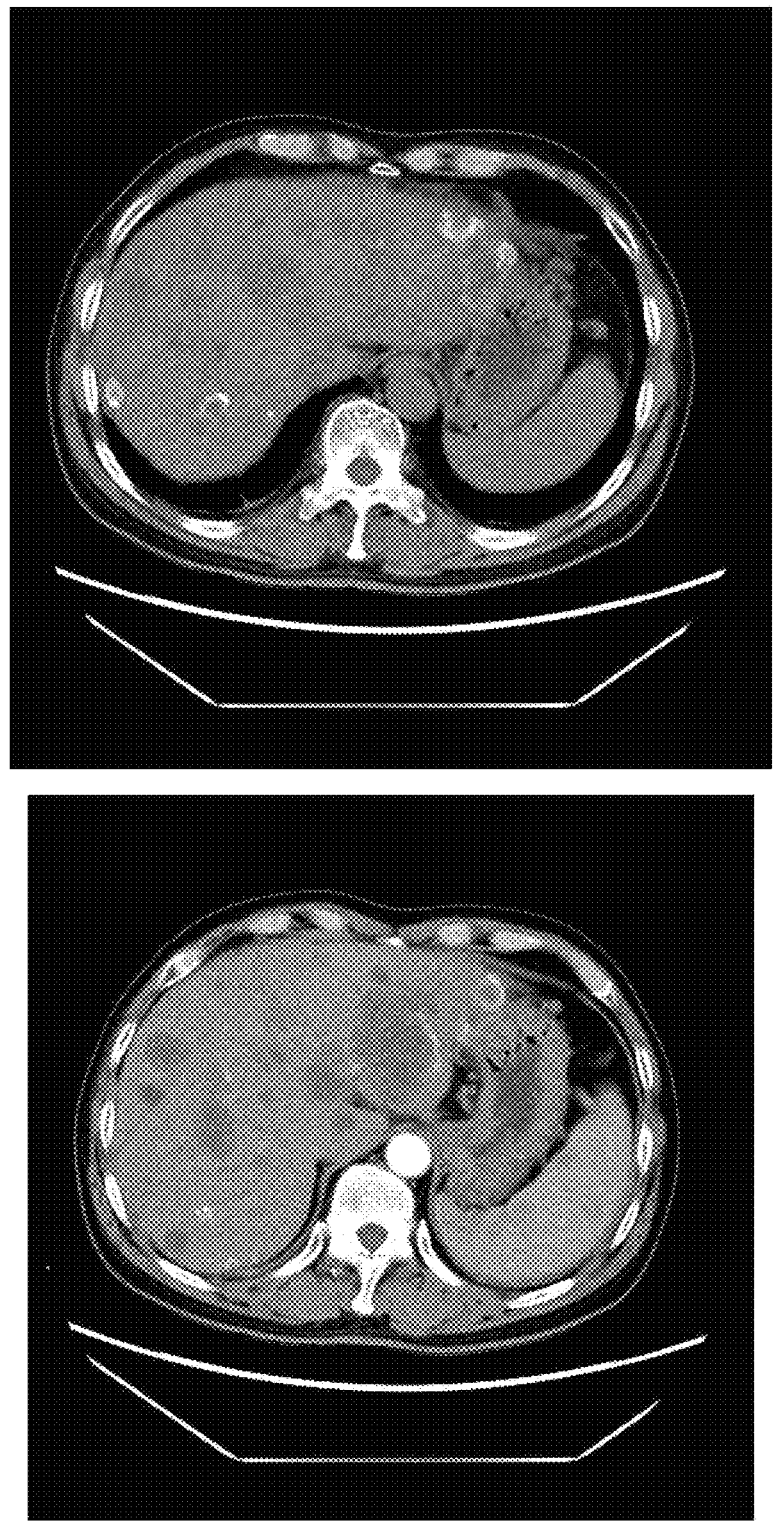
FIG. 26 shows CT images of a patient of pancreatic cancer before the procedure in accordance with an exemplary embodiment of the present invention.
Figure 27:
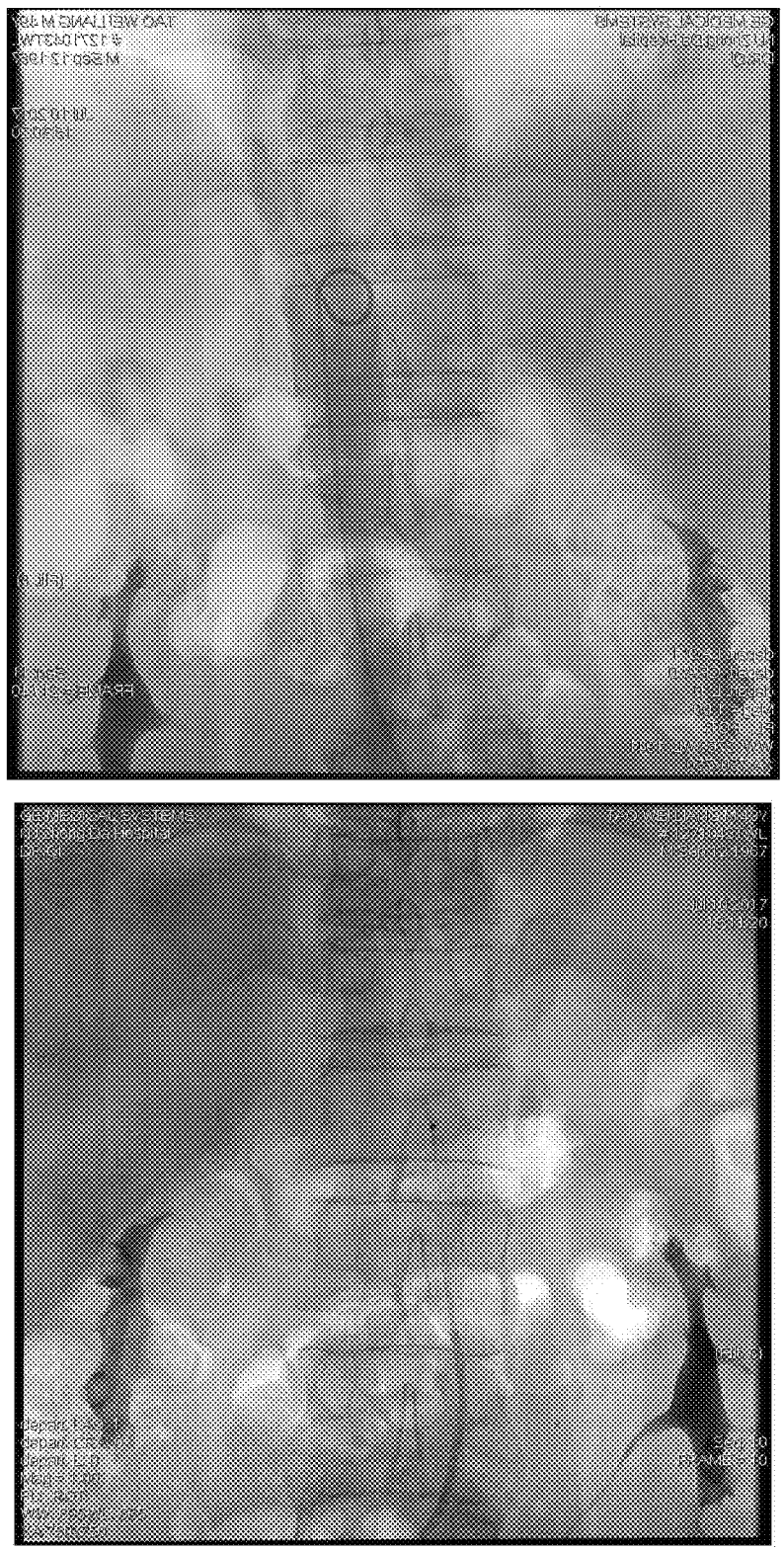
FIG. 27 shows CT images of a patient of pancreatic cancer during the procedure in accordance with an exemplary embodiment of the present invention.

Patient #2 (male, 49, pancreatic cancer): FIG. 26 shows CT images of the patient before the procedure, and FIG. 27 shows CT images of the patient during the procedure. Similar to patient #1, the entire treatment protocol for patient #2 includes two sessions, as summarized in Table 4.

TABLE 4

Treatment Protocol for Pancreatic Cancer

| Session | Electrode | Protocol |
|---|---|---|
| First Session | #1 | Rna/a = 10:110 (seconds): Power increases from 0 to 6.8 W (t = 0-42) and remains 6.8 W (t = 42-120); Temperature increases from BT to 60 C. (t = 0-42) and stays 60 C. for 78 seconds (t = 42-120); Impedance decreases from 190 to 180 Ohms (t = 0-120). |
| | #2 | Rna/a = 10:110 (seconds): Power increases from 0 to 6.1 W (t = 0-50) and decreases to 5.2 W (t = 50-120); Temperature increases from BT to 60 C. (t = 0-50) and stays 60 C. for 70 seconds (t = 50-120); Impedance decreases from 190 to 180 Ohms (t = 0-120). |

TABLE 4-continued

Treatment Protocol for Pancreatic Cancer

| Session | Electrode | Protocol |
|---|---|---|
| | #3 | Rna/a = 6:114 (seconds): Power increases from 0 to 3.2 W (t = 0-50) and remains 3.2 W (t = 50-120); Temperature increases from BT to 60 C. (t = 0-50) and stays 60 C. for 70 seconds (t = 50-120); Impedance decreases from 200 to 185 Ohms (t = 0-120). |
| | #4 | Rna/a = 19:101 (seconds): Power increases from 0 to 8.5 W (t = 0-32) and remains 8.5 W (t = 32-120); Temperature increases from BT to 50 C. (t = 0-32) and stays 50 C. for 88 seconds (t = 32-120); Impedance decreases from 200 to 195 Ohms (t = 0-120). |
| | #5 | Rna/a = 21:99 (seconds): Power increases from 0 to 8.1 W (t = 0-51) and stays at 8.1 W (t = 51-120); Temperature increases from BT to 50 C. (t = 0-51) and stays 50 C. for 69 seconds (t = 51-120); Impedance decreases from 200 to 196 Ohms (t = 0-120). |
| | #6 | Rna/a = 20:100 (seconds): Power increases from 0 to 8.4 W (t = 0-32) and remains 8.4 W (t = 32-120); Temperature increases from BT to 49 C. (t = 0-32) and stays 49 C. for 88 seconds (t = 32-120); Impedance decreases from 200 to 195 Ohms (t = 0-120). |
| Second Session | #1 | Rna/a = 28:92 (seconds): Power increases from 0 to 8.4 W (t = 0-28) and remains 8.4 W (t = 28-120); Temperature increases from BT to 45 C. (t = 0-28) and stays 45 C. for 92 seconds (t = 28-120); Impedance decreases from 200 to 198 Ohms (t = 0-120). |
| | #2 | Rna/a = 25:95 (seconds): Power increases from 0 to 9 W (t = 0-25) and remains 9 W (t = 25-120); Temperature increases from BT to 45 C. (t = 0-25) and stays 45 C. for 95 seconds (t = 25-120); Impedance remains 200 Ohms (t = 0-120). |
| | #3 | Rna/a = 15:105 (seconds): Power increases from 0 to 8.3 W (t = 0-42) and remains 8.3 W (t = 42-120); Temperature increases from BT to 57 C. (t = 0-42) and stays 57 C. for 78 seconds (t = 42-120); Impedance decreases from 200 to 197 Ohms (t = 0-120). |
| | #4 | Rna/a = 20:100 (seconds): Power increases from 0 to 8.5 W (t = 0-35) and remains 8.5 W (t = 35-120); Temperature increases from BT to 52 C. (t = 0-35) and stays 52 C. for 85 seconds (t = 35-120); Impedance decreases from 200 to 199 Ohms (t = 0-120). |
| | #5 | Rna/a = 20:100 (seconds): Power increases from 0 to 8.5 W (t = 0-35) and remains 8.5 W (t = 35-120); Temperature increases from BT to 50 C. (t = 0-35) and stays 50 C. for 85 seconds (t = 35-120); Impedance decreases from 200 to 190 Ohms (t = 0-120). |
| | #6 | Rna/a = 120:0 (seconds): Power increases from 0 to 8.8 W (t = 0-22) and remains 8.8 W (t = 22-120); Temperature increases from BT to 40 C. (t = 0-22) and stays 40 C. for 98 seconds (t = 22-120); Impedance decreases from 200 to 190 Ohms (t = 0-120). |

Figure 28:
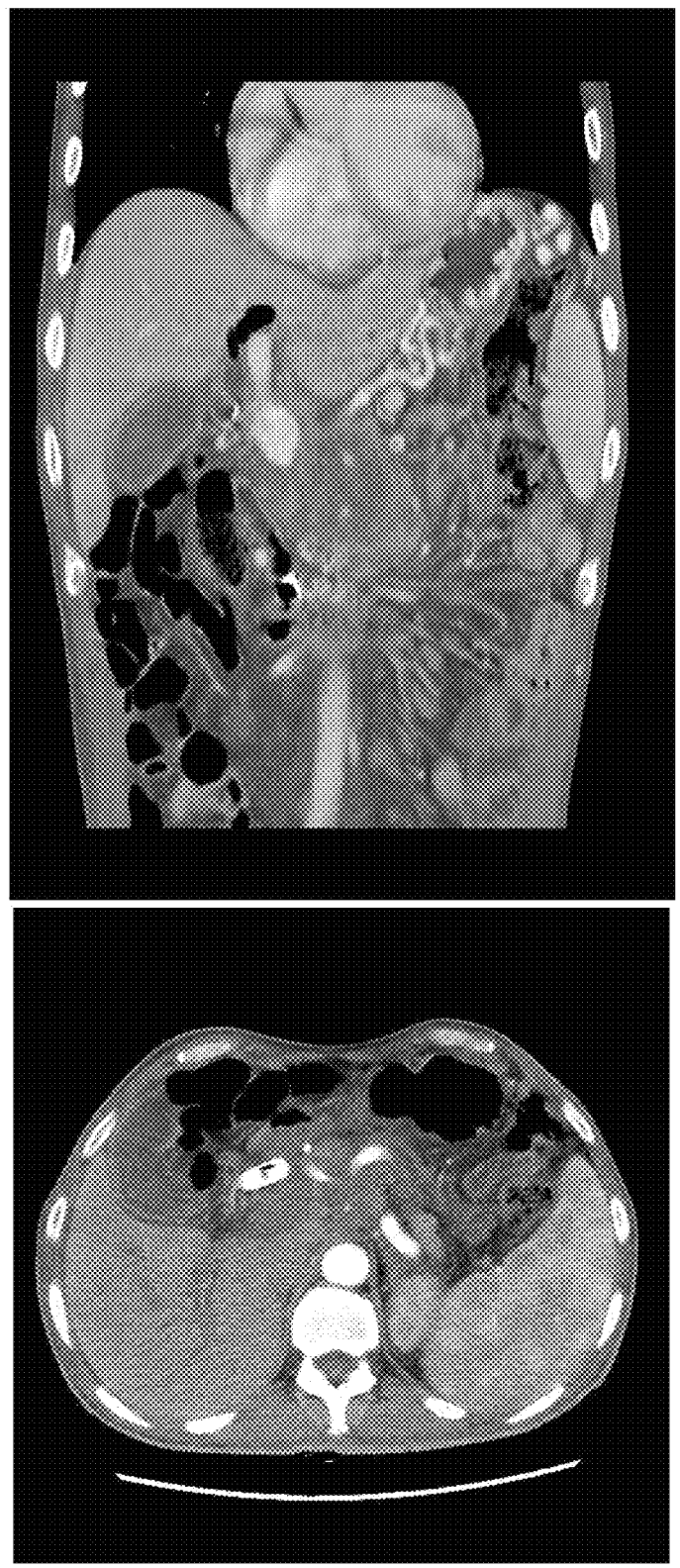
FIG. 28 shows CT images of another patient of pancreatic cancer before the procedure in accordance with an exemplary embodiment of the present invention.
Figure 29:
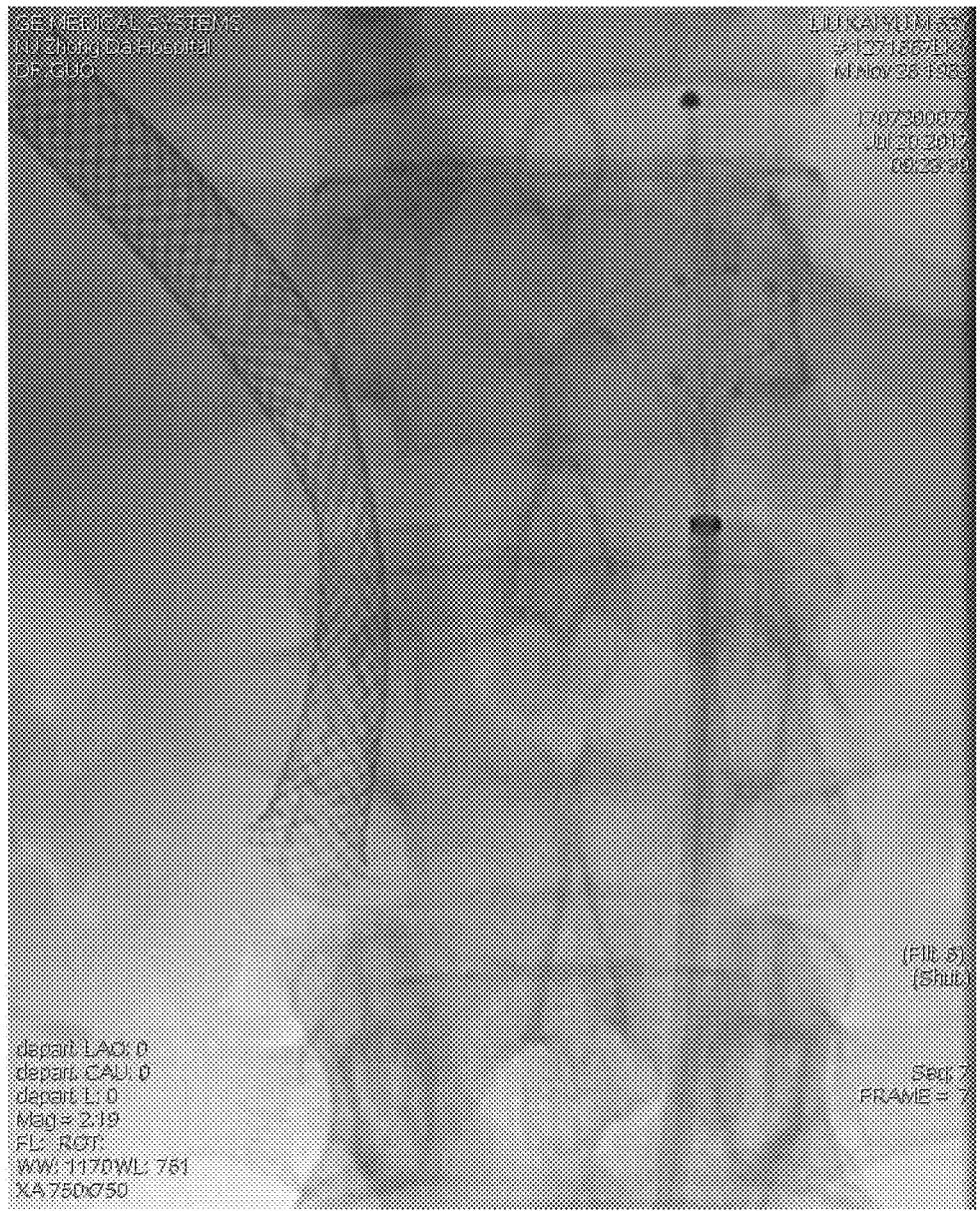
FIG. 29 shows CT images of another patient of pancreatic cancer during the procedure in accordance with an exemplary embodiment of the present invention.

Patient #3 (male, 53, pancreatic cancer): FIG. 28 shows CT images of the patient before the procedure, and FIG. 29 shows a CT image of the patient during the procedure. Similar to patient #1, the entire treatment protocol for patient #3 includes two sessions, as summarized in Table 5.

TABLE 5

Treatment Protocol for Pancreatic Cancer

| Session | Electrode | Protocol |
|---|---|---|
| First Session | #1 | Rna/a = 15:105 (seconds): Power increases from 0 to 8.6 W (t = 0-70) and remains 8.6 W (t = 70-120); Temperature increases from BT to 55 C. (t = 0-70) and increases to 60 C. (t = 70-120); Impedance decreases from 210 to 200 Ohms (t = 0-120). |
| | #2 | Rna/a = 17:103 (seconds): Power increases from 0 to 5.9 W (t = 0-90) and remains 5.9 W (t = 90-120); Temperature increases from BT to 50 C. (t = 0-90) and stays 50 C. for 30 seconds (t = 90-120); Impedance decreases from 205 to 200 Ohms (t = 0-120). |
| | #3 | Rna/a = 5:115 (seconds): Power increases from 0 to 2.8 W (t = 0-85) and remains 2.8 W (t = 85-120); Temperature increases from BT to 54 C. (t = 0-85) and stays 54 C. for 35 seconds (t = 85-120); Impedance decreases from 205 to 200 Ohms (t = 0-120). |
| | #4 | Rna/a = 10:110 (seconds): Power increases from 0 to 5.7 W (t = 0-59) and decreases to 3.8 W (t = 59-120); Temperature increases from BT to 57 C. (t = 0-59) and remains 57 C. for 61 seconds (t = 59-120); Impedance decreases from 205 to 200 Ohms (t = 0-60) and increases to 205 Ohms (t = 60-120). |

TABLE 5-continued

Treatment Protocol for Pancreatic Cancer

| Session | Electrode | Protocol |
|---|---|---|
| | #5 | Rna/a = 10:110 (seconds): Power increases from 0 to 4 W (t = 0-30) and to 6.3 W (t = 30-120); Temperature increases from BT to 50 C. (t = 0-30) and remains 50 C. for 90 seconds (t = 30-120); Impedance decreases from 205 to 200 Ohms (t = 0-120). |
| | #6 | Rna/a = 18:102 (seconds): Power increases from 0 to 5 W (t = 0-55) and remains 5 W (t = 55-120); Temperature increases from BT to 50 C. (t = 0-55) and stays 50 C. for 65 seconds (t = 55-120); Impedance decreases from 203 to 200 Ohms (t = 0-120). |
| Second Session | #1 | Rna/a = 5:55 (seconds): Power increases from 0 to 5.8 W (t = 0-60); Temperature increases from BT to 58 C. (t = 0-60); and Impedance decreases from 210 to 200 Ohms (t = 0-60). |
| | #2 | Rna/a = 10:110 (seconds): Power increases from 0 to 5.3 W (t = 0-120); Temperature increases from BT to 52 C. (t = 0-120); and Impedance decreases from 210 to 200 Ohms (t = 0-120). |
| | #3 | Rna/a = 10:110 (seconds): Power increases from 0 to 6 W (t = 0-120); Temperature increases from BT to 55 C. (t = 0-120); and Impedance decreases from 205 to 200 Ohms (t = 0-120). |
| | #4 | Rna/a = 15:105 (seconds): Power increases from 0 to 4 W (t = 0-50) and remains 4 W (t = 50-120); Temperature increases from BT to 50 C. (t = 0-50) and stays 50 C. for 70 seconds (t = 50-120); Impedance decreases from 205 to 200 Ohms (t = 0-120). |
| | #5 | Rna/a = 10:110 (seconds): Power increases from 0 to 4.4 W (t = 0-50) and remains about 4.4 W (t = 50-120); Temperature increases from BT to 49 C. (t = 0-50) and stays 49 C. for 70 seconds (t = 50-120); Impedance decreases from 205 to 200 Ohms (t = 0-120). |
| | #6 | Rna/a = 12:108 (seconds): Power increases from 0 to 4.7 W (t = 0-40), remains about 4.7 W (t = 40-100), and increases to 6.3 W (t = 100-120); Temperature increases from BT to 48 C. (t = 0-40) and stays 48 C. for 80 seconds (t = 40-120); Impedance decreases from 203 to 199 Ohms (t = 0-120). |

Figure 30:
FIG. 30 shows CT images of still another patient of pancreatic cancer in accordance with an exemplary embodiment of the present invention.

Patient #4 (female, 74, pancreatic cancer): FIG. 30 shows CT images of the patient. Similar to patient #1, the entire treatment protocol for patient #4 includes two sessions, as summarized in Table 6.

TABLE 6

Treatment Protocol for Pancreatic Cancer

| Session | Electrode | Protocol |
|---|---|---|
| First Session | #1 | Rna/a = 18:102 (seconds): Power increases from 0 to 9 W (t = 0-53) and decreases to 7.5 W (t = 53-120); Temperature increases from BT to 60 C. (t = 0-90) and stays 60 C. for 30 seconds (t = 90-120); Impedance decreases from 190 to 170 Ohms (t = 0-120). |
| | #2 | Rna/a = 25:95 (seconds): Power increases from 0 to 9 W (t = 0-35) and remains 9 W (t = 35-120); Temperature increases from BT to 48 C. (t = 0-30) and increases to 51 C. (t = 30-120); Impedance decreases from 190 to 180 Ohms (t = 0-120). |
| | #3 | Rna/a = 18:15 (seconds): Power increases from 0 to 9 W (t = 0-33), off test; Temperature increases from BT to 60 C. (t = 0-33) and off test; Impedance decreases from 190 to 185 Ohms (t = 0-30) and jumps to 400 Ohms (t = 30-33), off test. |
| | #4 | Rna/a = 10:110 (seconds): Power increases from 0 to 6 W (t = 0-80) and remains about 6 W (t = 80-120); Temperature increases from BT to 60 C. (t = 0-80) and stays 60 C. for 40 seconds (t = 80-120); Impedance decreases from 185 to 175 Ohms (t = 0-120). |
| | #5 | Rna/a = 10:110 (seconds): Power increases from 0 to 8.1 W (t = 0-120); Temperature increases from BT to 57 C. (t = 0-120); Impedance decreases from 190 to 175 Ohms (t = 0-120). |
| | #6 | Rna/a = 13:107 (seconds): Power increases from 0 to 8.7 W (t = 0-48) and remains about 8.7 W (t = 48-120); Temperature increases from BT to 58 C. (t = 0-120); Impedance decreases from 185 to 175 Ohms (t = 0-120). |
| Second Session | #1 | Rna/a = 10:110 (seconds): Power increases from 0 to 7 W (t = 0-40), and remains about 7 W (t = 40-120); Temperature increases from BT to 60 C. (t = 0-40) and stays 60 C. for 80 seconds (t = 40-120); Impedance decreases from 195 to 185 Ohms (t = 0-120). |
| | #2 | Rna/a = 10:110 (seconds): Power increases from 0 to 6 W (t = 0-47), and down to 5 W (t = 47-120); Temperature increases from BT to 60 C. (t = 0-47) and stays 60 C. for 73 seconds (t = 47-120); Impedance decreases from 195 to 185 Ohms (t = 0-120). |

TABLE 6-continued

Treatment Protocol for Pancreatic Cancer

| Session | Electrode | Protocol |
|---|---|---|
| | #3 | Rna/a = 8:112 (seconds); Power increases front 0 to 3.5 W (t = 0-45), and remains 3.5 W (t = 45-120); Temperature increases from BT to 60 C. (t = 0-45) and stays 60 C. for 75 seconds (t = 45-120); Impedance decreases from 200 to 185 Ohms (t = 0-120). |
| | #4 | Rna/a = 10:110 (seconds): Power increases from 0 to 5.5 W (t = 0-70), and remains 5.5 W (t = 70-120); Temperature increases from BT to 52 C. (t = 0-70) and stays 52 C. for 50 seconds (t = 70-120); Impedance decreases from 180 to 175 Ohms (t = 0-120). |
| | #5 | Rna/a = 10:110 (seconds): Power increases from 0 to 8 W (t = 0-120); Temperature increases from BT to 59 C. (t = 0-120); Impedance decreases from 185 to 175 Ohms (t = 0-120). |
| | #6 | Rna/a = 9:111 (seconds): Power increases from 0 to 6 W (t = 0-60), and remains ~6 W (t = 60-120); Temperature increases from BT to 53 C. (t = 0-60) and stays 53 C. for 60 Seconds (t = 60-120); Impedance decreases from 180 to 170 Ohms (t = 0-120). |

In the foregoing specification, embodiments of the present invention have been described with reference to numerous specific details that may vary from implementation to implementation. The specification and drawings are, accordingly, to be regarded in an illustrative rather than a restrictive sense. The sole and exclusive indicator of the scope of the invention, and what is intended by the applicant to be the scope of the invention, is the literal and equivalent scope of the set of claims that issue from this application, in the specific form in which such claims issue, including any subsequent correction.

The invention claimed is:

1. A method of relieving or alleviating abdominal cancer pain or improving pain VAS score in a cancer patient comprising (1) placing multiple electrodes within a segment of the abdominal aorta of the patient and against blood vessel wall of the abdominal aorta by percutaneous transluminal intravascular access, wherein said segment is defined as between the origin of celiac artery and the origin of superior mesenteric artery; (2) adhering a surface electrode on an external surface such as skin of the patient; and (3) releasing radiofrequency energy through at least one of the multiple electrodes to nearby tissues, so as to increase the temperature of the nearby tissues and induce a thermal alteration of the nearby tissues.

2. The method according to claim 1, further comprising: adjusting or changing the adhesion position of the surface electrode on the back or butt of the patient to vary the impedance between the surface electrode and a given electrode within the abdominal aorta until the impedance falls within the range of 180-220 such as 200 Ohms, before step (2).

3. The method according to claim 1, wherein the radiofrequency energy is released at a level of no more than 9 W (joule per second) to prevent spasm of the patient.

4. The method according to claim 1, wherein the radiofrequency energy is released with a temperature threshold setting of 60° C. to ensure that collagen does not denature, tissue does not shrink, and cell wall does not break, in the nearby tissue.

5. The method according to claim 1, wherein the radiofrequency energy is released through an alternating current of 460-470 KHz such as 465 KHz between the surface electrode and a given electrode within the abdominal aorta.

6. The method according to claim 1, wherein the cancer is selected from pancreatic cancer, cervical carcinoma, cholangiocarcinoma, and esophageal cancer; wherein an average QOL-100 score increases >25 points for patient after the method is completed, as compared to that before the method is completed; wherein an average visual analog score (VAS) of the patient is reduced by ≥4 points after the method is completed, as compared to that before the method is completed, indicating a significant pain palliation.

7. The method according to claim 1, further comprising administrating a first daily amount of analgesic to the patient before step (1), and administrating a second daily amount of analgesic to the patient after step (3), wherein the second daily amount is less than 50% of the first daily amount.

8. The method according to claim 1, wherein the radiofrequency energy is released for a continuous period of 60-120 seconds for each of the multiple electrodes one by one, which protocol is defined as one session; and wherein step (3) comprises two, three, four, or more such sessions separately carried out.

9. The method according to claim 8, wherein the thermal alteration comprises non-ablative thermal alteration, ablative thermal alteration, or any combination thereof; and wherein the thermal alteration produces a lesion with a depth of 5-8 mm or 5.9-6.9 mm such as about 6.4 mm in the nearby tissues.

10. The method according to claim 9, wherein the time period for non-ablative thermal alteration (<45° C.) is defined as Tna, the time period for ablative thermal alteration (≥45° C.) is defined as Ta, and the ratio between the two is defined as Rna/a; and Rna/a is in the range of from 5:115 to 17:43 (seconds).

11. The method according to claim 10, wherein the cancer is cervical cancer or cervical carcinoma, and wherein Rna/a values are in the range of from 5:115 to 17:43 such as Rna/a values of 10:50, 8:52, 5:55, 5:55, 12:48, and 17:43 (seconds) for a first session; and Rna/a values of 5:55, 12:108, 20:45, 7:113, 5:115, and 6:114 (seconds) for a second session; or wherein the cancer is esophageal cancer with retroperitoneum lymph nodes invasion, and wherein Rna/a values are in the range of from 3:57 to 10:50 such as Rna/a values of 10:50, 5:55, and 8:52 (seconds) for a first session; Rna/a values of 9:51, 9:51, 8:52, 7:53, and 4:56 (seconds) for a second session; Rna/a values of 3:57, 5:55, 3:57, 3:57, 4:56, and 3:57 (seconds) for a third session; and Rna/a values of 7:53, 5:55, 3:57, 3:57, 9:51, and 3:57 (seconds) for a fourth session; or wherein the cancer is pancreatic cancer, and wherein Rna/a values are in the range of from 6:114 to 28:92 such as Rna/a values of 10:110, 10:110, 6:114, 19:10,1

21:99, and 20:100 (seconds) for a first session, and Rna/a values of 28:92, 25:95, 15:105, 20:100, and 20:100 (seconds) for a second session; or wherein the cancer is pancreatic cancer, and wherein Rna/a values are in the range of from 5:115 to 18:102 such as Rna/a values of 15:105, 17:103, 5:115, 10:110, 10:110, and 18:102 (seconds) for a first session, and Rna/a values of 5:55, 10:110, 10:110, 15:105, 10:110, and 12:108 (seconds) for a second session; or wherein the cancer is pancreatic cancer, and wherein Rna/a values are in the range of from 8:112 to 25:95 such as Rna/a values of 18:102, 25:95, 10:110, 10:110, and 13:107 (seconds) for a first session, and Rna/a values of 10:110, 10:110, 8:112, 10:110, 10:110, and 9:111 (seconds) for a second session.

12. The method according to claim 1, wherein the multiple electrodes consist of six electrodes configured to create interrupted spiral but full circumferential lesions on internal wall of said segment of the abdominal aorta of the patient.

13. The method according to claim 12, wherein the six electrodes are a part of a catheter apparatus, which comprises: an elongated shaft having a proximal portion and a distal portion; a carrier carrying six therapeutic assemblies, wherein the carrier is located at, or proximate to, the distal portion of the elongated shaft, and wherein each therapeutic assembly comprises one of the six electrodes for intravascular treatment; wherein the carrier is configured to vary between a delivery configuration and a deployed configuration; wherein the distal portion of the shaft is configured for intravascular delivery of the carrier; wherein the carrier comprises six right-handed wire helixes and six left-handed wire helixes that are plainly or bi-axially woven into a tubular structure; wherein the carrier comprises at least one interstice that is defined by four wire helix segments from two immediately adjacent right-handed wire helixes and two immediately adjacent left-handed wire helixes that are plainly or bi-axially woven into each other; and wherein at least one therapeutic assembly wraps around at least one of said four wire helix segments to stabilize said at least one interstice, to maintain structural integrity of the carrier, and to prevent tangling of wire helixes, when the carrier is being distorted intravascularly.

14. The method according to claim 13, wherein at least one of the six right-handed wire helixes and at least one of the six left-handed wire helixes are made from one single wire having a first portion of right-handed wire helix and a second portion of left-handed wire helix by folding or bending a point of the single wire between the first portion and the second portion at an angle of from about 160 to 180 degree.

15. The method according to claim 14, wherein the catheter apparatus further comprises a multi-lumen bundler, wherein the multi-lumen bundler has a cylinder body, and a number of lumens pass axially through the cylinder body along the longitudinal axis of the cylinder body; and wherein the first portion of right-handed wire helix and the second portion of left-handed wire helix from a same wire are inserted into and pass through two different lumens, and the wire is permanently glued and fixed to the multi-lumen bundler with a liquid adhesive material filled into or dropped into the lumens and solidified thereafter.

16. The method according to claim 13, wherein the therapeutic assembly wraps around only one of said four wire helix segments to stabilize the interstice.

17. The method according to claim 16, wherein the therapeutic assembly includes two terminal bodies and a main body positioned between the two terminal bodies; and wherein cross-sectional area of the main body along a plane perpendicular to the elongation direction of the wire segment being wrapped around is larger than cross-sectional areas of the terminal bodies along a plane perpendicular to the elongation direction of the wire segment being wrapped around, which are larger than a cross-sectional area of the wire segment being wrapped around along a plane perpendicular to the elongation direction of the wire segment.

18. The method according to claim 17, wherein length of the wire segment being wrapped around is maintained to be equal to, or longer than, the main body's length along the elongation direction of the wire segment being wrapped around.

19. The method according to claim 17, wherein length of the wire segment being wrapped around is maintained to be equal to, or longer than, the main body's length combined with length of one of the two terminal bodies, or total length of the two terminal bodies, along the elongation direction of the wire segment being wrapped around.

20. The method according to claim 17, wherein at least one of the two terminal bodies and the main body includes (1) one or more grooves for accommodating or guiding one or more wire helixes that slide(s) over the wire segment around which the therapeutic assembly wraps; and/or (2) one, two or more protrusions, wherein the gap(s) between the protrusion(s) and the wire segment around which the therapeutic assembly wraps, and the gap(s) between said protrusion(s) themselves, is(are) configured for accommodating or guiding one or more wire helixes that slide(s) over the wire segment around which the therapeutic assembly wraps.

\* \* \* \* \*